United States Patent
Mohanty et al.

(10) Patent No.: US 11,180,537 B2
(45) Date of Patent: Nov. 23, 2021

(54) OPTOGENETIC MODULATION BY MULTI-CHARACTERISTIC OPSINS FOR VISION RESTORATION AND OTHER APPLICATIONS

(71) Applicant: Nanoscope Technologies LLC, Bedford, TX (US)

(72) Inventors: Samarendra Kumar Mohanty, Arlington, TX (US); Sulagna Bhattacharya, Arlington, TX (US)

(73) Assignee: Nancoscope Technologies LLC, Bedford, TX (US)

( * ) Notice: Subject to any disclaimer, the term of this patent is extended or adjusted under 35 U.S.C. 154(b) by 0 days.

(21) Appl. No.: 16/347,375

(22) PCT Filed: Nov. 3, 2017

(86) PCT No.: PCT/US2017/059922
§ 371 (c)(1),
(2) Date: May 3, 2019

(87) PCT Pub. No.: WO2018/106369
PCT Pub. Date: Jun. 14, 2018

(65) Prior Publication Data
US 2020/0255484 A1 Aug. 13, 2020

Related U.S. Application Data

(60) Provisional application No. 62/418,196, filed on Nov. 6, 2016.

(51) Int. Cl.
*C07K 14/47* (2006.01)
*A61K 38/00* (2006.01)

(52) U.S. Cl.
CPC .............. *C07K 14/47* (2013.01); *A61K 38/00* (2013.01)

(58) Field of Classification Search
CPC .... C07K 14/47; A61K 38/00; A61K 48/0058; A61K 48/005; A61P 27/02; A01K 2227/105; A01K 2267/0306; C12N 2750/14143; C12N 2830/008
See application file for complete search history.

(56) References Cited

U.S. PATENT DOCUMENTS

2014/0324134 A1  10/2014 Klapoetke et al.
2016/0361439 A1* 12/2016 Agbandje-McKenna ................... A61P 27/02

FOREIGN PATENT DOCUMENTS

| JP | 2013544494 A | 12/2013 |
|----|--------------|---------|
| WO | 2010011404 A2 | 1/2010 |
| WO | 2013038666 A1 | 3/2013 |
| WO | 2015157761 A1 | 10/2015 |

OTHER PUBLICATIONS

Bamann, Christian. et al.; Spectral Characteristics of the Photocycle of Channelrhodopsin-2 and its Implication for Channel Function; J. Mol. Biol., 2008, vol. 375, pp. 684-694.
Gauvain, Gregory, et al.; Optogenetic visual restoration using ChrimsonR: Photoactivation below safety radiation limit in retinal ganglion cell populations from non-human primates; Investigative Ophthalmology & Visual Science Sep. 2016. vol. 57, 598.
Klapoetke, Nathan, et. al.; Independent optical excitation of distinct neural populations: Nature Methods, 2014, vol. 11, No. 3, pp. 338-346.
Schild, Lisa, et. al.; Dual Color Neural Activation and Behavior Control with Chrimson and CoChR in Caenorhabditis elegans; Genetics. Aug. 2015, vol. 200. pp. 1029-1034.
Bamann, C. et al., "Spectral Characteristics of the Photocycle of Channelrhodopsin-2 and Its Implication for Channel Function", Journal of Molecular Biology, 2008, vol. 375, pp. 686-694; available online Nov. 1, 2007.
Klapoetke, N. C. et al., "Independent optical excitation of distinct neural populations", Nature Methods, 2014, vol. 11, No. 3, pp. 338-346; published online Feb. 9, 2014.
PCT/US2017/059922 International Search Report dated Jun. 13, 2018.
PCT/US2017/059922 Written Opinion of the International Search Authority dated Jun. 13, 2018.
Australian Office Action, app. No. 2017372351.
Lin, John Y.; "A User's Guide to Channelrhodopsin Variants: Features, Limitations and Future Developments," Exp. Physiol. Jan. 2011; 96(1): 19-25.
Bamann, Christian, et. al.; "Spectral Characteristics of the Photocycle of Channelrhodopsin-2 and its Implication for Channel Function," J. Mol. Biol. (2008) 375, 686-694, Nov. 1, 2007.
Office Action and translation from Japanese, dated Oct. 8, 2019.
Schild, Lisa, et. al.; "Dual Color Neural Activation and Behavior Control with Chrimson and CoChR in Caenorhabditis elegans"; Genetics, vol. 200, 1029-1034; May 28, 2015.
EESR Mar. 6, 2020; EP17878191.
Wright, Weldon, et. al.; "Restoring vision in mice with retinal degeneration using multicharacteristic opsin," Neurophotonics 4(4), 041505 (Aug. 18, 2017).

* cited by examiner

*Primary Examiner* — Sudhakar Katakam
(74) *Attorney, Agent, or Firm* — Sand IP

(57) ABSTRACT

This invention, in one aspect, relates generally to compositions and methods for modulating cellular activities by synthetic opsins. Further, the invention provides method for the use of synthetic opsins for vision restoration and other applications, wherein the amino acid sequence of the synthetic opsin is modified to provide enhanced light sensitivity, kinetics and ion-selectivity.

6 Claims, 24 Drawing Sheets
Specification includes a Sequence Listing.

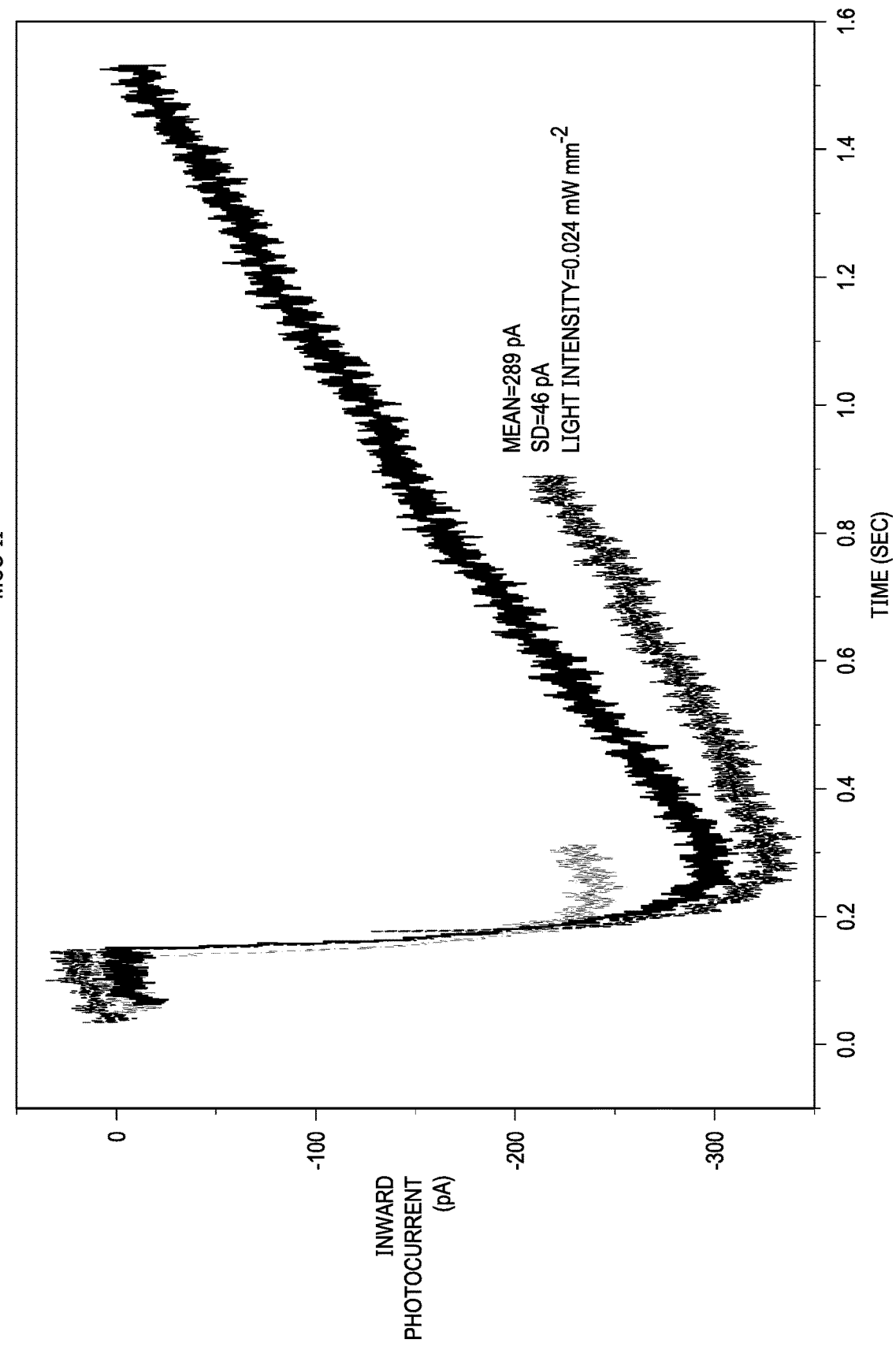

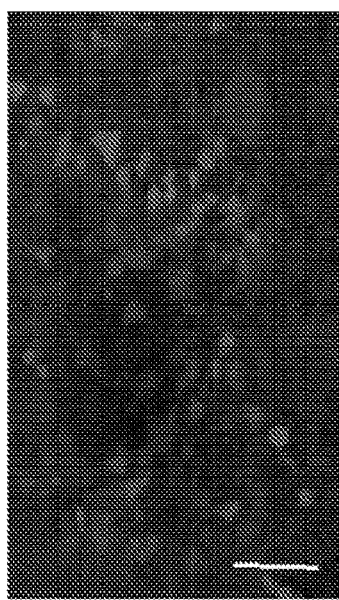 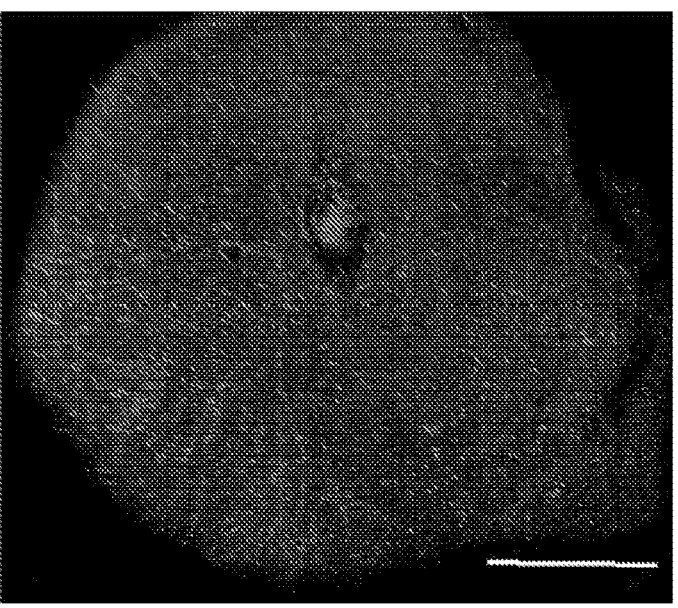
FIG. 7A  FIG. 7B
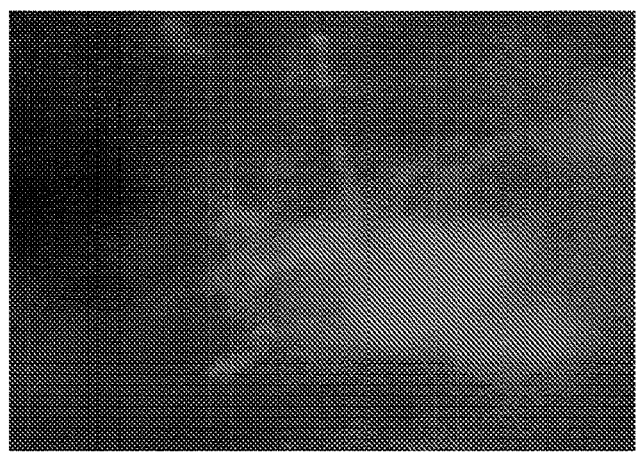
FIG. 8A
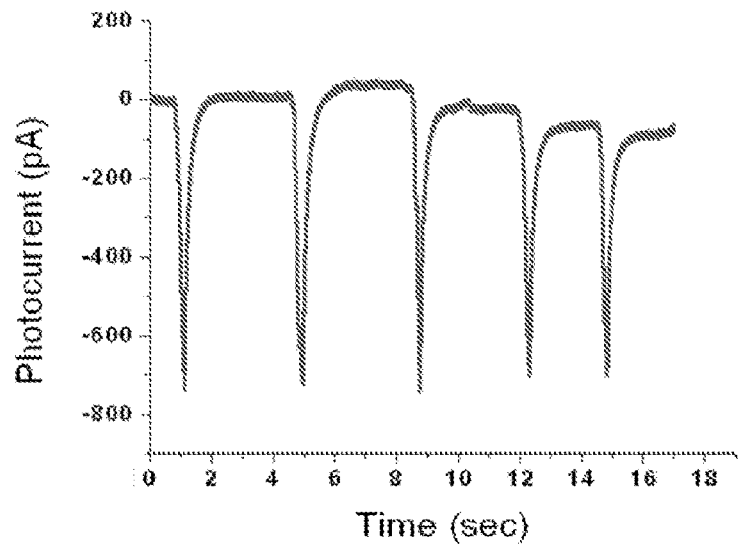
FIG. 8B

FIG. 10A
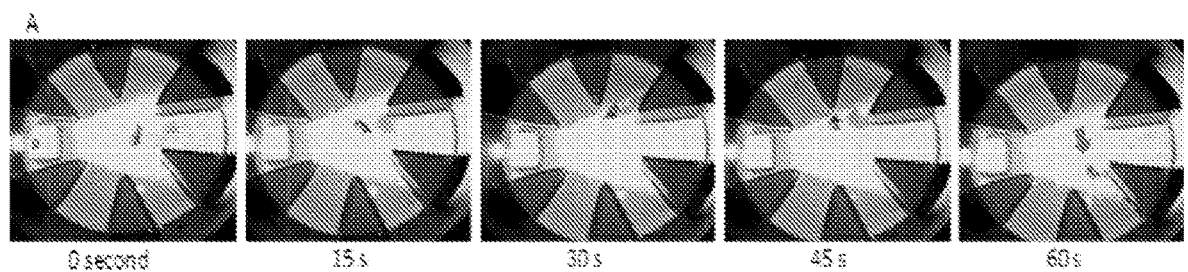
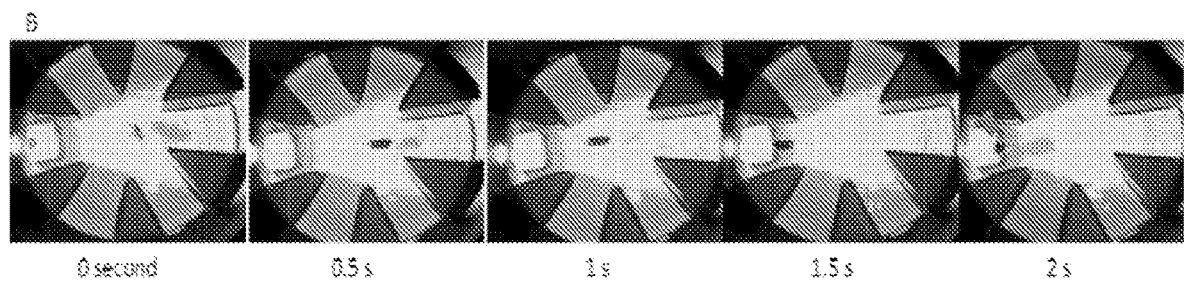
FIG. 10B

OPTOGENETIC MODULATION BY MULTI-CHARACTERISTIC OPSINS FOR VISION RESTORATION AND OTHER APPLICATIONS

FIELD OF THE INVENTION

This invention relates generally to compositions and methods for modulating cellular activities by synthetic opsins. More specifically, the invention provides enhanced light sensitivity to neurons for vision restoration and other therapeutic applications.

DESCRIPTION OF THE TEXT FILE SUBMITTED ELECTRONICALLY

The contents of the text field submitted electronically herewith are incorporated herein by reference in their entirety: A computer readable format copy of the Sequence Listing (file name: NATE2000WO_SL.rtf, date recorded: 11/03/17, file size 48 kilobytes).

BACKGROUND OF THE INVENTION

In retinal degenerative diseases such as dry age-related macular degeneration (AMD) and Retinitis Pigmentosa (RP), the photoreceptors (e.g., rods and cones) that are responsible for conversion of light into electro-chemical signals, are degenerated. This prevents the generation of photo-induced signals in retina, breaking the vision-sensory related cascade of events within the visual system. Loss of photoreceptor cells and/or loss of photoreceptor cell function are the primary causes of reduced light sensitivity and blindness.

SUMMARY OF THE INVENTION

In order to meet the challenges in vision loss, principles of the present disclosure provide several light-sensitive ion-channel molecules and methods of their preparation and different uses including vision restoration. The invention also includes isolated nucleic acid sequences that encode light-sensitive ion-channels of the invention, and constructs that comprise such nucleic acid sequences.

In one aspect, the disclosure provides light-sensitive ion-channels (Multi-Characteristics Opsins) synthetically: (i) having high photosensitivity at multiple visible wavelengths, (ii) with plasmid size that could be packaged into safe virus.

In addition, the disclosure in some aspects provides expression of Multi-Characteristics Opsins (MCOs) in cells in-vitro or in-vivo as well as methods for modulating cellular activities by these synthetic opsins.

In one aspect, the Multi-Characteristics Opsins are highly sensitive to visible light and ambient-light activatable. In some aspect, expression of a specific MCO in cell produces a long-lasting inward current in response to white light similar to characteristic photoreceptor-rod signal.

In another aspect, the disclosure provides a synthetic, ambient-light activatable, fast, enhanced Multi-Characteristics Opsin (eMCO1) which has stabilizer-biomarker that play an active role in stabilizing the whole protein molecule (eMCO1) expression on membrane with higher percentage of beta sheets and lower percentage of disordered structure (i.e. less prone to cleavage) and also enhancing the photo-induced current in the cells expressing eMCO1.

In another aspect, the disclosure provides a synthetic, ambient-light activatable, fast, enhanced Multi-Characteristics Opsin (eMCO1) which has stabilizer-biomarker to confirm the gene expression in targeted cells.

According to another aspect of the invention, the light emitted from the stabilizer-biomarker present in the enhanced Multi-Characteristics Opsin (eMCO1) enhances the photo-induced current in the cells expressing eMCO1 by light emitted/re-emitted from the stabilizer-biomarker molecule.

According to another aspect of the invention, the disclosed invention provides method for the use of synthetic opsins for vision restoration and other applications, wherein the amino acid sequence of the synthetic opsin is modified to provide enhanced light sensitivity, kinetics and ion-selectivity.

The present disclosure provides a method of delivering MCO to degenerated retinas in order to restore light sensitivity. The results presented herein show efficient and stable in-vivo expression of MCO-reporter protein in mice retina after intravitreal injection of Adeno-Associated Virus carrying MCO. The results also demonstrated that the expression of MCO in retina of mouse model of retinal degeneration enables behavioral restoration of vision. The number of error arms and time to reach platform in a radial-arm water maze significantly reduced after delivery of MCO to the mice having degenerated retina. Notably, the improvement in visually guided behavior was observed even at light intensity levels orders of magnitude lower than that required for Channelrhodopsin-2 opsin.

According to yet another aspect, the present disclosure provides a method of efficient restoration of vision in human. The method include use of MCO which when expressed in retinal cells produces a slower depolarizing phase after initial response to white light similar to characteristic photoreceptor-rod signal, and delivery of the opsin to retinal cells in-vivo by Adeno-Associated Virus (AAV) carrying promoter-MCO-gene in eye, and/or in combination with Pronase E or Alpha-Aminoadipic Acid (AAA) for enhancing delivery efficiency to targeted retinal layer crossing the thick inner limiting membrane in humans.

Biodistribution study using qPCR analysis showed negligible quantities of MCO-gene in different tissues of the mice intravitreally injected with rAAV carrying MCO genes. Safe virus-mediated MCO-delivery has potential for effective gene therapy of diverse retinal degenerations in patients.

In another aspect, the present disclosure provides the use of opsin that produces a slower depolarizing phase after initial response to white light similar to characteristic photoreceptor-rod signal, thus restoration of vision in blind individuals in contrast to existing use of opsins, which do not produce slower depolarizing phase after initial response to light.

The disclosure provides nucleic acid molecules that encode for any of the polypeptides described herein. Moreover, the nucleic acid molecule(s) may further include a pharmaceutically acceptable carrier.

The disclosure provides a method, wherein cells have been contacted with or comprises an isolated nucleic acid molecule that encodes for an isolated polypeptide molecule of the invention. Preferably, the cells are rod bipolar cells, ON-type retinal ganglion cells, or ON-type bipolar cells.

In a broader aspect, the disclosure provides methods for using the opsins to modulate the cell and tissue function, and for use in diagnosis and treatment of disorders.

In one embodiment, the present invention includes a recombinant, ambient-light activatable, fast Multi-Characteristics Opsin (MCO1) protein comprising: an MCO1 protein comprising 14 trans-membrane domains mutated to modulate at least one of ion selectivity, light sensitivity, or kinetics of the MCO1 protein. The protein of claim 1, wherein the MCO1 protein has SEQ ID NO: 1, 3, 5, 7, or 11. In one aspect, one or more of the following single or combinations of mutations modulate ion selectivity, light sensitivity, or kinetics, wherein the mutation is selected from at least one of: S to C substitution at an amino acid residue corresponding to amino acid 132 of the MCO1 sequence; E to A substitution at an amino acid residue corresponding to amino acid 123 of the MCO1 sequence; D to A substitution at an amino acid residue corresponding to amino acid 253 of the MCO1 sequence; R to A substitution at an amino acid residue corresponding to amino acid 120 of the MCO1 sequence; Q to A, substitution at an amino acid residue corresponding to amino acid 56 of the MCO1 sequence; K to A substitution at an amino acid residue corresponding to amino acid 93 of the MCO1 sequence; E to A substitution at an amino acid residue corresponding to amino acid 90 of the MCO1 sequence; E to Q substitution at an amino acid residue corresponding to amino acid 90 of the MCO1 sequence; E to A substitution at an amino acid residue corresponding to amino acid 97 of the MCO1 sequence; E to A substitution at an amino acid residue corresponding to amino acid 101 of the MCO1 sequence; N to D substitution at an amino acid residue corresponding to amino acid 258 of the MCO1 sequence; E to T substitution at an amino acid residue corresponding to amino acid 83 of the MCO1 sequence; E to T substitution at an amino acid residue corresponding to amino acid 123 of the MCO1 sequence; or S to D substitution at an amino acid residue corresponding to amino acid 63 of the MCO1 sequence.

In another embodiment, the present invention includes a recombinant, ambient-light activatable, slow Multi-Characteristics Opsin (MCO2) protein comprising: 14 trans-membrane domains; wherein 7 amino acid residues (VNKGTGK) from 309 to 315 are deleted in the molecule of claim 1 to improve the gene expression on membrane; wherein S132L mutation is carried out in the trans-membrane domain 2 of SEQ ID NO: 1 to cause increased binding affinity towards retinal and increased light sensitivity; wherein the opsin is encoded in 658 amino acids; and wherein the MCO2-sensitized cell generates a slowly decaying inward current after initial fast current response to a pulse of white light. In one aspect, a single or a combination of mutations is selected from E473A, D603A, R469A of SEQ ID NO:1 that further modulate at least one of the ion selectivity, light sensitivity, or kinetics of the molecule. In another aspect, a trans-membrane sequence (TPARWVWISLYYAAFYVVMTGLFALCIYVLMQTI) is inserted after amino acid residue 315 in MCO1 (SEQ ID NOS:1 or 2) or 308 amino acid residues in MCO2 (SEQ ID NOS:3 or 4).

In another embodiment, the present invention includes a recombinant, ambient-light activatable, fast, enhanced Multi-Characteristics Opsin (eMCO1) comprising MCO1 sequence (SEQ ID NO: 1) and a stabilizer-biomarker sequence. In one aspect, the recombinant eMCO1 further comprises at least one of: the stabilizer-biomarker is 900 amino acids of SEQ ID NO: 11; the stabilizer-biomarker is connected downstream with the 14-transmembrane domain by a linking sequence; a light emitted from the stabilizer-biomarker stabilizes eMCO1 expression in a membrane with higher percentage of beta sheets and lower percentage of disordered structure and is less prone to cleavage that a non-modified MCO1; the stabilizer-biomarker molecule enhances a photo-induced current in cells expressing eMCO1 by better orientation-stabilization of eMCO1 across a membrane; the stabilizer-biomarker molecule enhances a photo-induced current in cells expressing eMCO1 by light emitted/re-emitted from the stabilizer-biomarker molecule; a promoter is used upstream to eMCO1 to target specific cells; the promoter-eMCO1 gene is packaged in a viral vector; cells can be transfected with the promoter-eMCO1 gene using chemical, viral, or physical transfection; an examination of eMCO1 containing stabilizer-biomarker expression in retina (by fundoscopy) is an indicator for determining efficacy of gene delivery to targeted tissue(s); a light emitted/re-emitted by the stabilizer-biomarker is monitored used to determine presence of eMCO1 expression; or a loss of expression requires re-delivery of the promoter-eMCO1 gene to re-photosensitize/functionalize target cells. In another aspect, the recombinant cMOC1 further comprises a reporter-gene is downstream from the MCO1 gene to detect cellular expression/activation, wherein the promoter-MCO1-reporter gene is packaged in a viral vector; and wherein cells can be transfected by the promoter-MCO1-reporter gene using either chemical, viral or physical method. In another aspect, MCO-sensitized cells are highly sensitive to light and can be activated at low intensity (~0.02 mW/mm$^2$) ambient light. In another aspect, the MCO-sensitized retinal neurons (e.g. retinal ganglion cells, bipolar cells) produces a slower depolarizing phase after initial response to white light similar to a wild-type photoreceptor-rod signal. In another aspect, the opsin is sensitive to any wavelength of light in a visible and a near-infrared range. In another aspect, the opsin is activated by a single-photon including direct, and indirect (e.g., fluorescence, phosphorescence, up/down conversion) illumination light in a visible and a near-infrared range.

In another embodiment, the present invention includes methods and uses of the MCO1, MCO2 or eMCO1, or mutants thereof for restoration of lost vision. In one aspect, the vision loss is due to any degenerative retinal disease; wherein delivery of a recombinant MCO-gene to targeted cells is carried out by an intravitreal/sub-retinal injection of a virus carrying promoter-MCO-gene in an eye, in combination with Pronase E or alpha-aminoadipic acid (AAA) for enhancing delivery efficiency, or both; wherein delivery of the MCO-gene is carried out by intravitreal/sub-retinal injection of promotor-MCO-gene plasmids in eye, followed by either chemical, or physical transduction method or a combination thereof; wherein the MCO-gene delivery into eye does not cause either undesired expression in non-targeted cells and organs, or any adverse reaction or cytotoxicity in the treated eye; wherein significant visually guided behavioral improvement is observed after delivery of MCO-gene; or wherein reinjection and transfection of the MCO-gene is carried out in case of deficiency in MCO-gene expression.

In another embodiment, the present invention includes methods and uses of the MCO1, MCO2 or eMCO1 for preventing or slowing down the vision loss, wherein delivery of the MCO-gene is carried out to retinal cells during progressive photoreceptor loss; wherein light stimulation of the MCO-sensitized retinal cells is carried out to prevent or slow down the photoreceptor loss; and wherein the light stimulation dose is optimized for maximal efficacy.

In another embodiment, the present invention includes methods and uses of the MCO1, MCO2 or eMCO1 for restoration of vision by regenerating the damaged RGC axons: wherein delivery of the MCO-gene is carried out to retinal ganglion cells during or after axonal degeneration;

wherein light stimulation of the MCO-sensitized RGCs is carried out to slow down the rate of degeneration and/or to regenerate the axons; and wherein the light stimulation dose is optimized for minimizing the degeneration and/or maximizing the axonal regeneration.

In another embodiment, the present invention includes methods and uses of the MCO1, MCO2 or eMCO1 for stimulation of different types of excitable cells including neurons, cardiac cells: wherein the use comprises delivery of the MCO-gene by either chemical, viral or physical transduction method; wherein activation of MCO is achieved upon illumination of light; and wherein the effect is measured by electro/opto-physiology.

In another embodiment, the present invention includes methods and uses of the MCO1, MCO2 or eMCO1 for treatment of disorders: wherein the use comprises delivery of the MCO-gene to different organs by either chemical, viral or physical transduction method; wherein activation of MCO is achieved upon illumination of light; and wherein an effect is measured by an electrophysiology or other functional and behavioral analysis.

In another embodiment, the present invention includes a polypeptide comprising a sequence comprising at least 75%, 85%, 95% or 100% identity to SEQ ID NO: 1, 3, 5, 7 or 11, wherein said polypeptide exhibits the photosensitivity characteristics of the protein of at least one of SEQ ID NO: 1, 3, 5, 7, or 11.

In another embodiment, the present invention includes a recombinant nucleic acid encoding a polypeptide having at least 75%, 85%, 95% or 100% identity to SEQ ID NO: 1, 3, 5, 7 or 11, wherein said polypeptide exhibits the photosensitivity characteristics of the protein of at least one of SEQ ID NO: 1, 3, 5, 7 or 11. In one aspect, the nucleic acid has at least one of 75%, 85%, 95% or 100% identity to SEQ ID NO: 2, 4, 6, or 8. In another embodiment, the invention includes a vector comprising the nucleic acid having 75%, 85%, 95% or 100% identity to at least one of SEQ ID NO: 1, 3, 5, 7 or 11. In one aspect, the vector is selected from an adenovirus, adeno-associated virus or lentivirus vector.

In another embodiment, the present invention includes a method of treating blindness comprising administering to a patient in need thereof a vector comprising the nucleic acid having 75%, 85%, 95% or 100% identity to at least one of SEQ ID NO: 1, 3, 5, 7 or 11.

Details associated with the embodiments described above and others are described below.

BRIEF DESCRIPTION OF THE DRAWINGS

The following drawings illustrate by way of example and not limitation. For the sake of brevity and clarity, every feature of a given structure is not always labeled in every figure in which that structure appears.

Tables 1-4 show Amino acid sequences of Multi-Characteristics Opsins (MCOs): MCO1, MCO2, MCO1T, MCO2T. MCO2 contains mutation (S 132 L) of MCO1 and deletion of 7 amino acid residues (VNKGTGK (SEQ ID NO: 13)) after 308. MCO1T and MCO2T contain additional transmembrane sequence (TPARWVWISLYYAAFYVVMTGL-FALCIYVLMQTI (SEQ ID NO: 14)) after 315 and 308 amino acid residues respectively.

Table-05 shows the DNA sequences of promoter (mGluR6) used upstream of MCO-sequences for targeting specific cells as an example; and Table-06 shows the DNA sequences of reporter (mCherry) used downstream of MCO-sequences for confirming expression in specific cells as an example.

Table-06 shows DNA sequences of reporter-stabilizer (mCherry) used downstream of MCO-sequences for confirming expression in specific cells as an example.

Table-07 shows Amino acid and DNA sequences of Enhanced Multi-Characteristics Opsin-1 (eMCO1). It contains MCO1 sequence (Table-01) and biomarker-stabilizer sequence (Table-06)

Table-08 shows the comparison of stability of the MCO1 and eMCO1 based on secondary structure and folding using theoretical modeling by RaptorX.

Figure 1A:
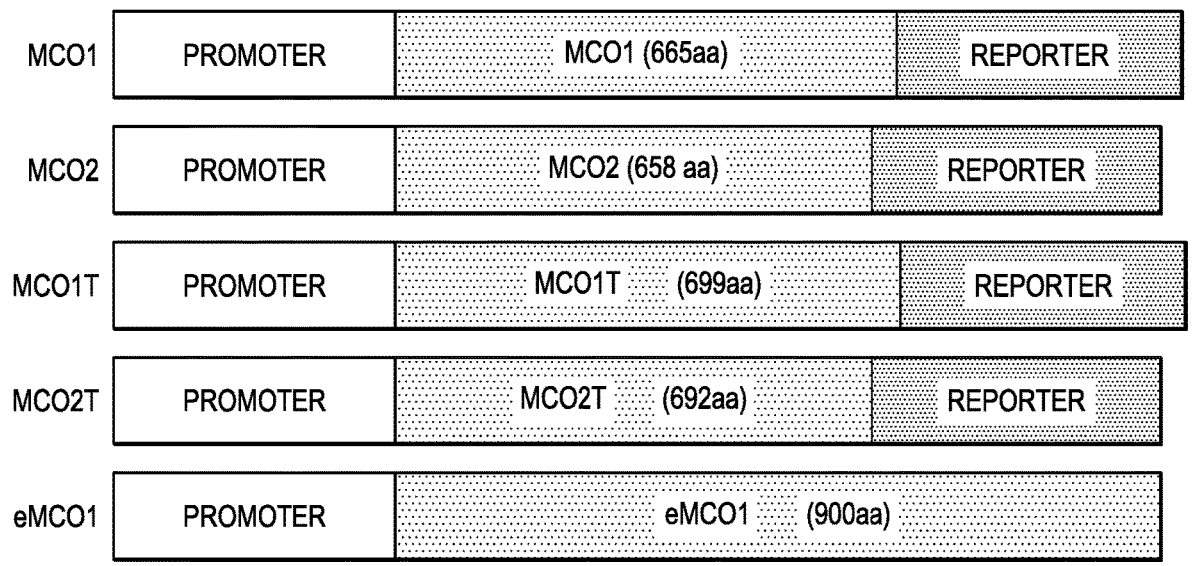

FIG. 1A illustrates domain architecture of Multi-Characteristics Opsins (MCOs) with reporter protein, which includes eMCO1.

Figure 1B:
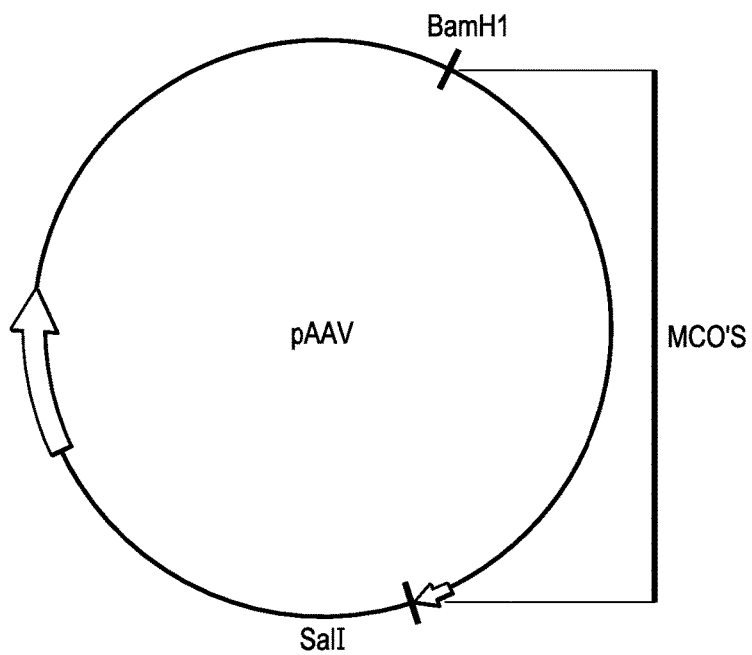

FIG. 1B shows typical circular map showing the insertion of MCO gene cloned at the restriction sites (BamH I and Sal I).

Figure 2A:
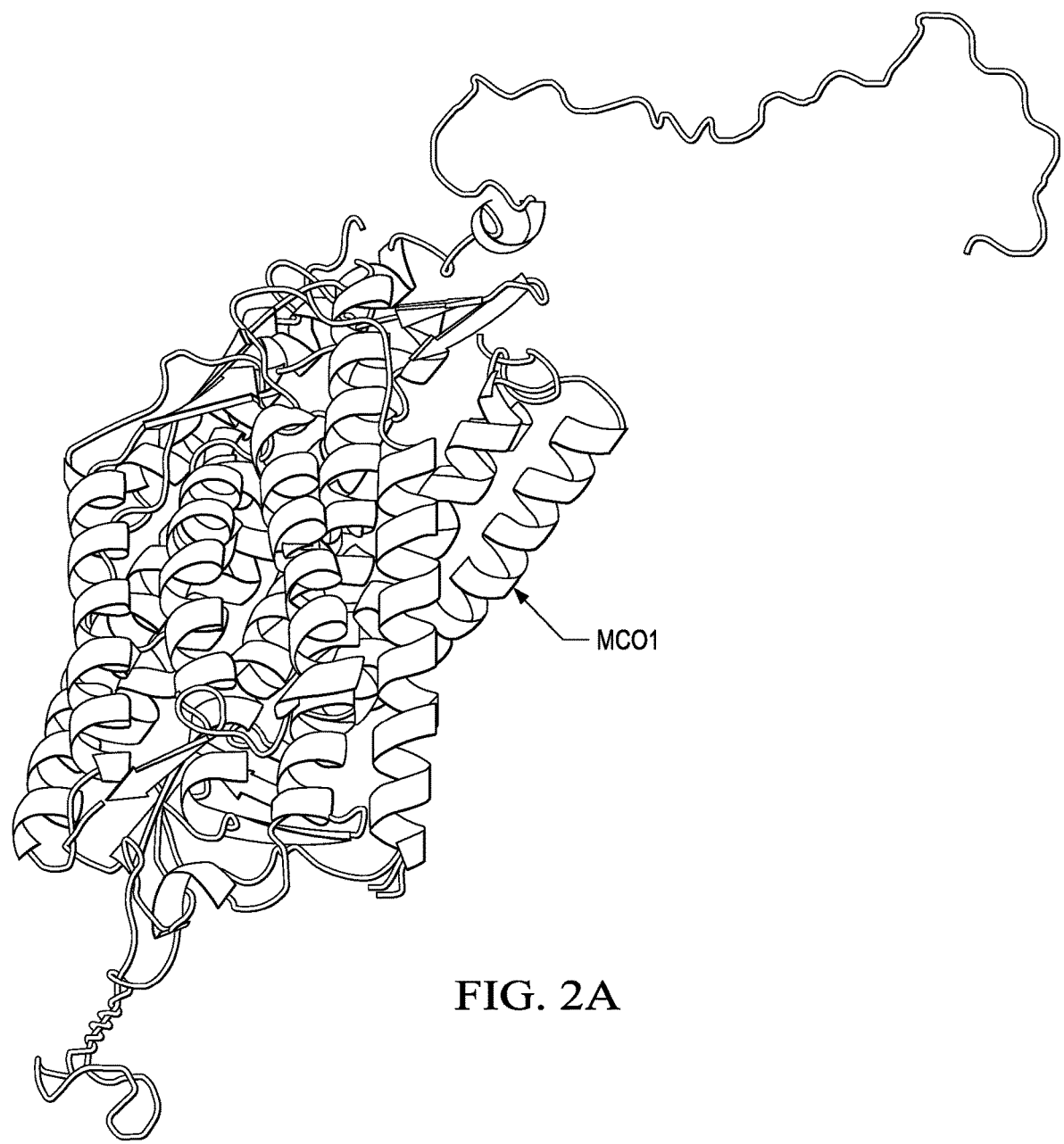
Figure 2B:
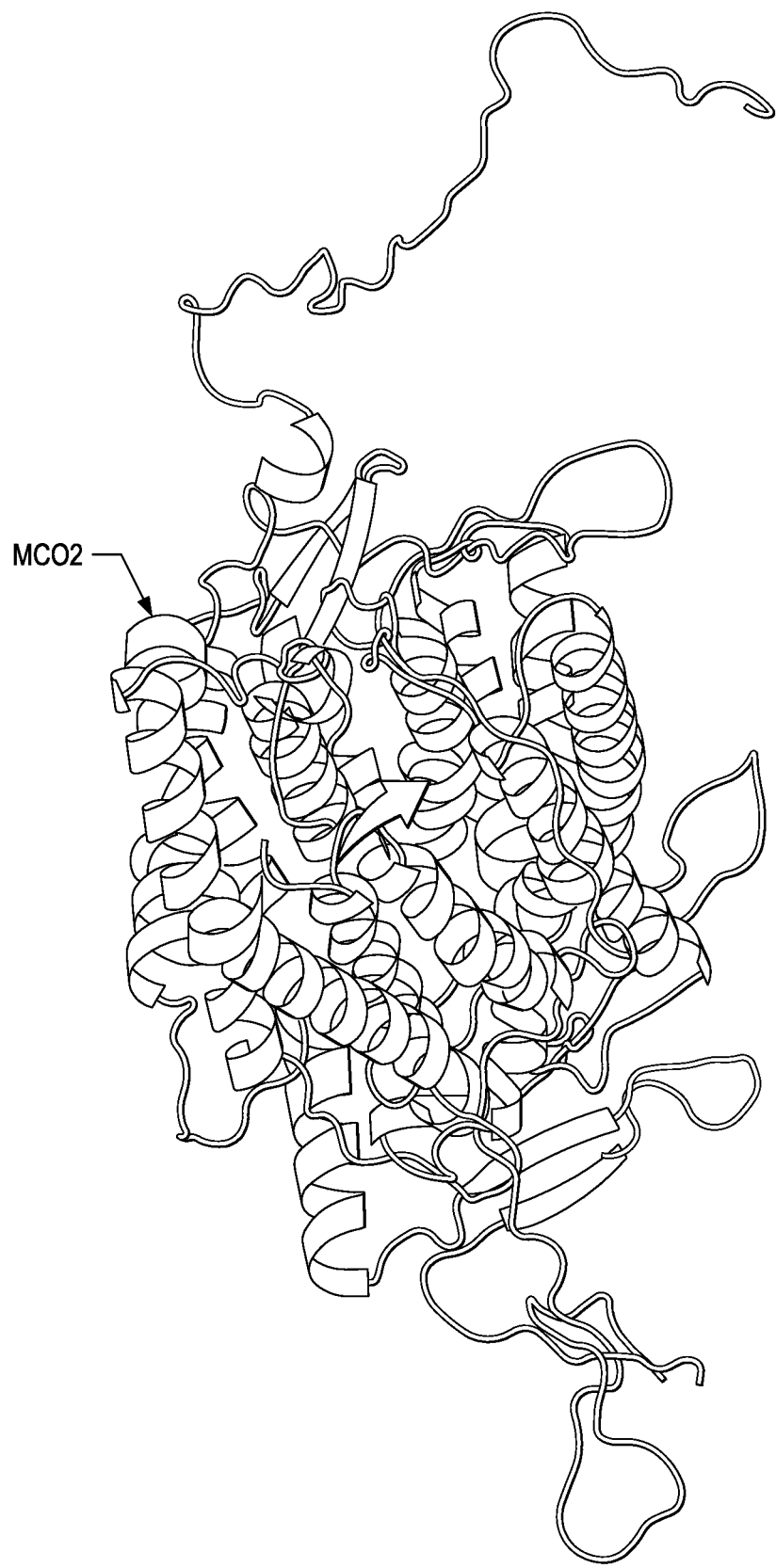
Figure 2C:
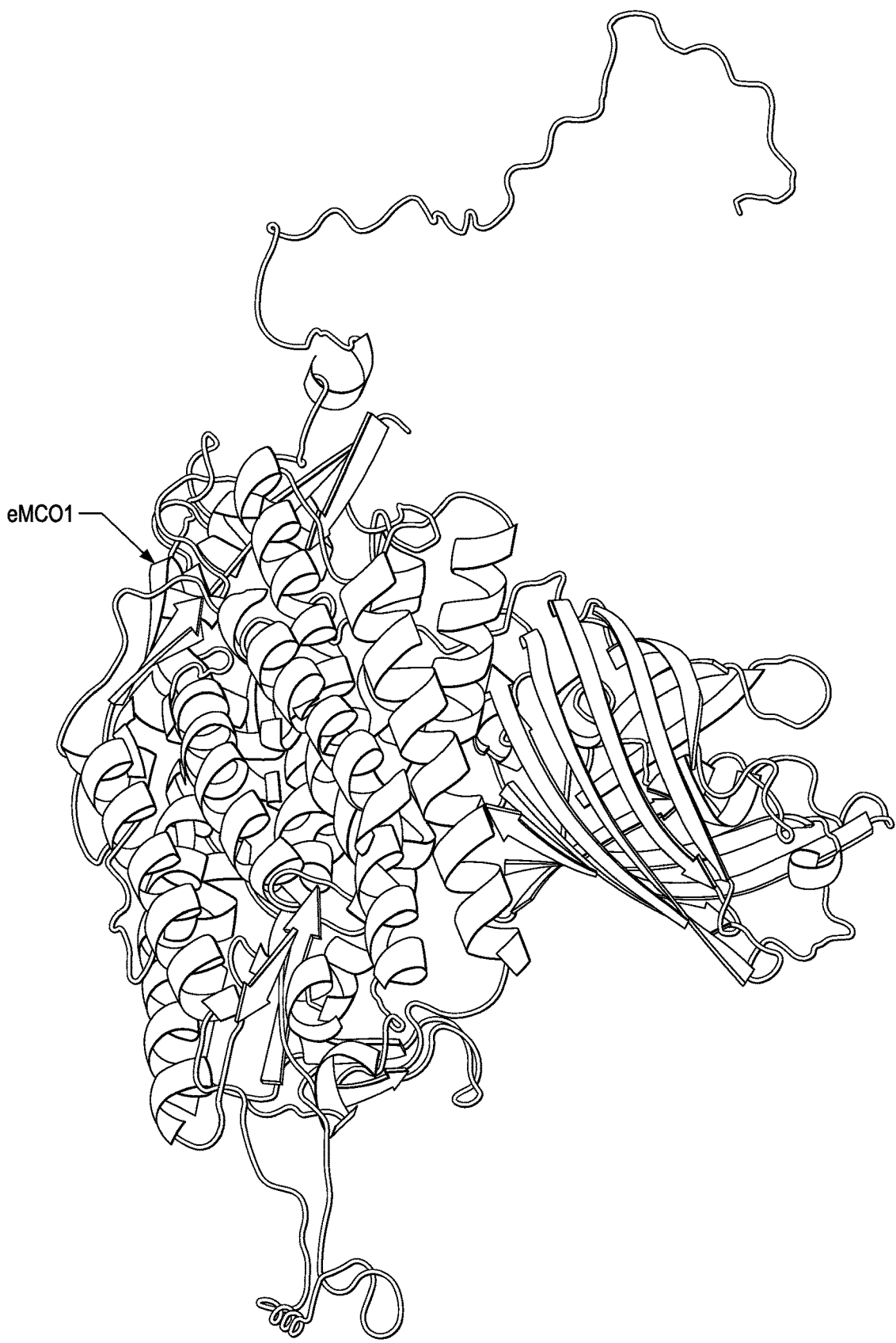

FIGS. 2A and 2B show Theoretical modeling of the three-dimensional arrangement of amino acid chains of Multi-Characteristics Opsins. FIG. 2A_shows the theoretical modeling of the three-dimensional arrangement of amino acid chains of Multi-Characteristics Opsin, MCO1. FIG. 2B depicts the theoretical modeling of the three-dimensional arrangement of amino acid chains of Multi-Characteristics Opsin, MCO2. FIG. 2C shows the theoretical modeling of the three-dimensional arrangement of amino acid chains of Multi-Characteristics Opsin, eMCO1.

Figure 3A:
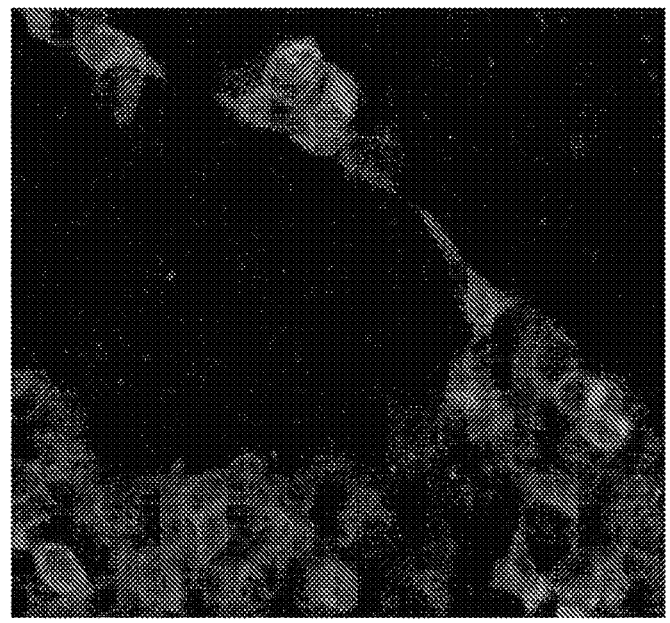
Figure 3B:
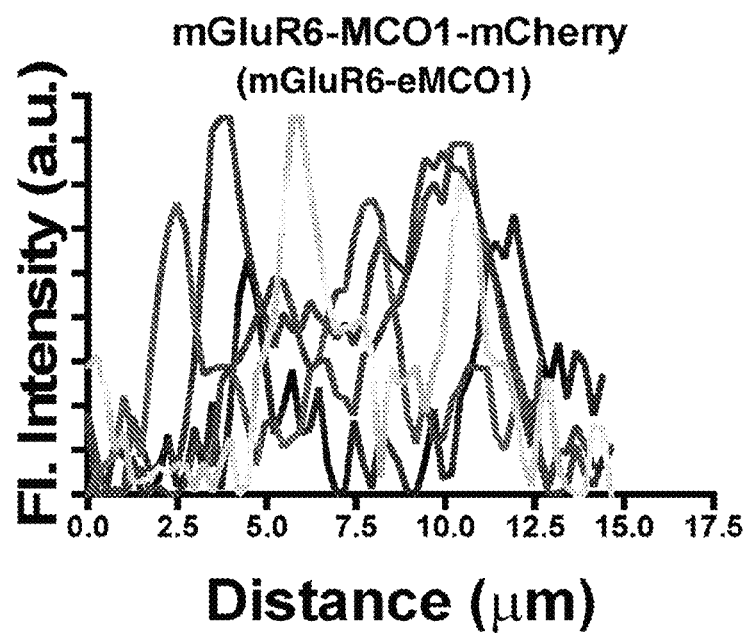

FIGS. 3A and 3B show expression of eMCO1 in model HEK 293 cells. FIG. 3A Expression of eMCO1 is localized in plasma membrane. Confocal fluorescence images of HEK293 cells transfected with mGluR6-MCO1-mCherry (mGluR6-eMCO1), FIG. 3B Intensity of eMCO1 reporter fluorescence along line across representative cells.

Figure 4A:
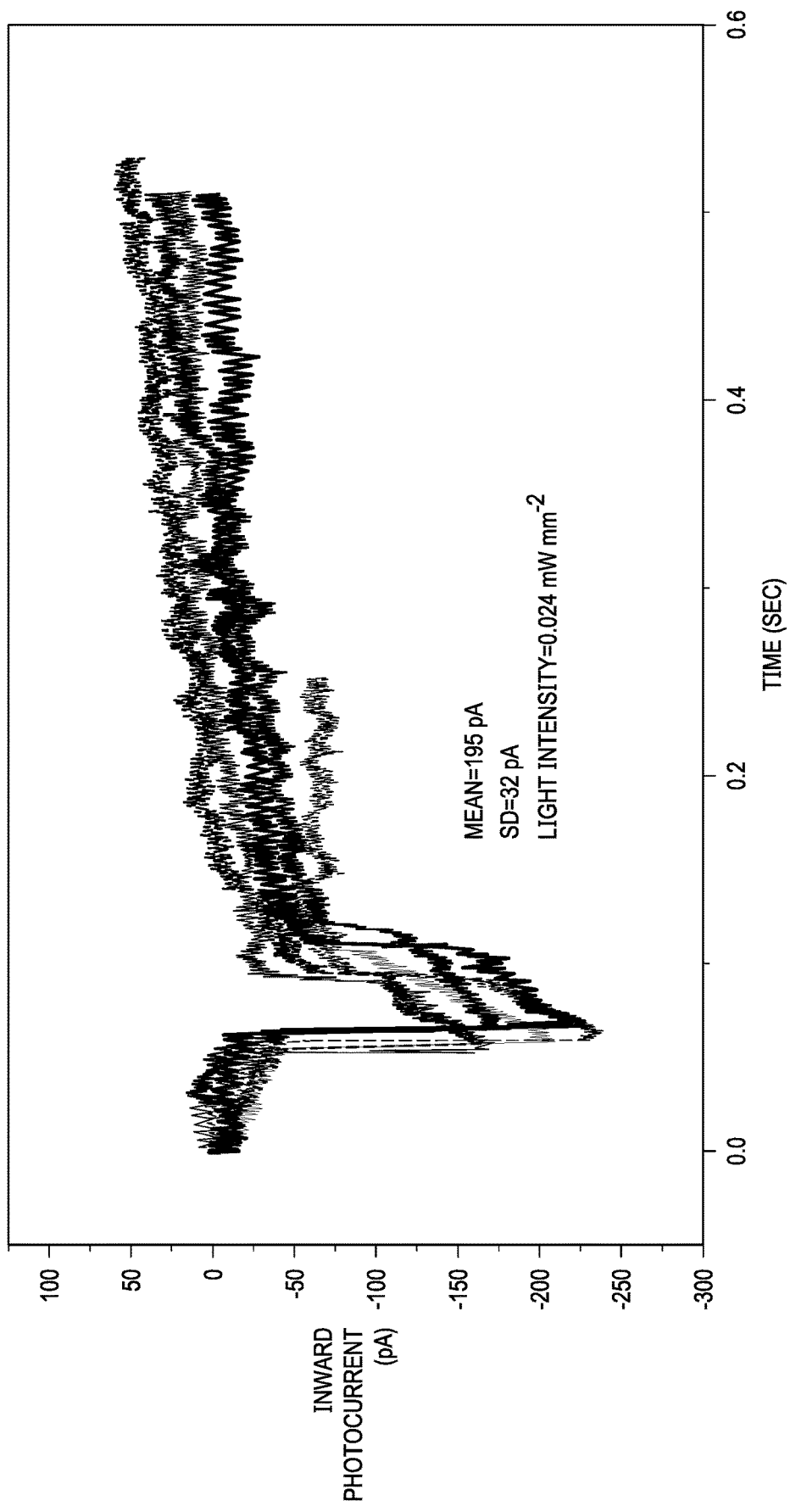
Figure 4B:
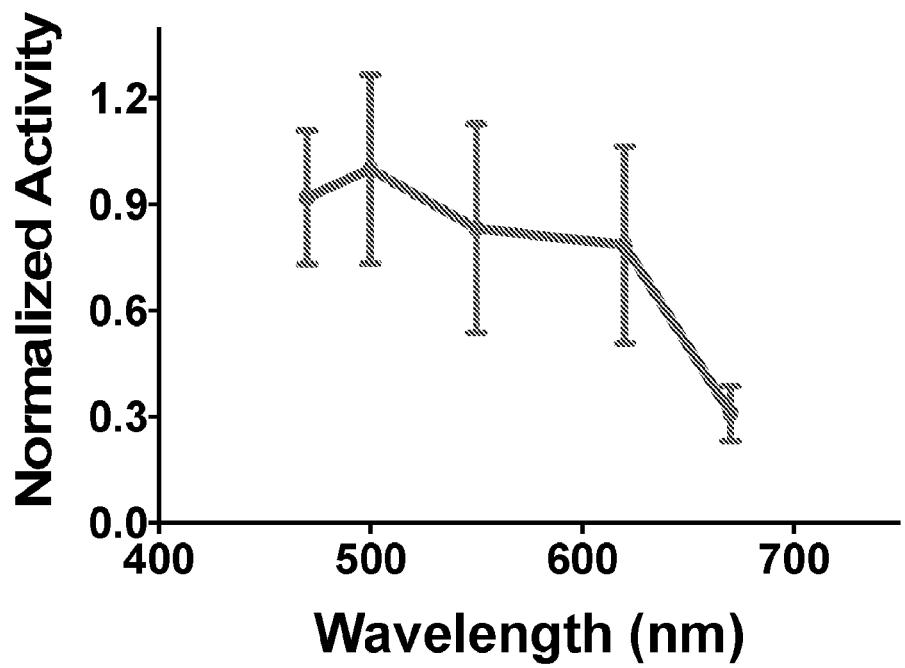

FIGS. 4A and 4B illustrates functioning of Multi-Characteristics Opsin (eMCO1). FIG. 4A shows inward current profiles in eMCO1-expressing cells in response to light (average intensity: 0.024 mW/mm$^2$). FIG. 4B Activation spectrum of eMCO1. Average ±SEM.

Figure 5A:
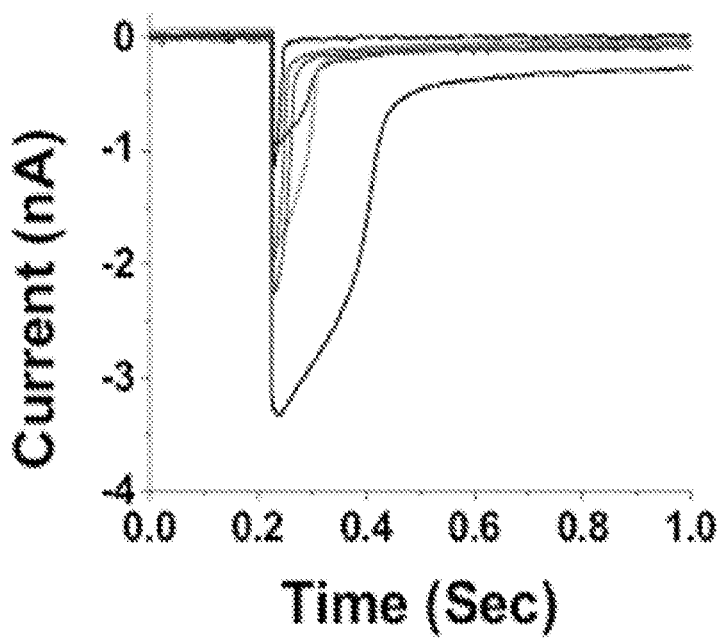
Figure 5B:
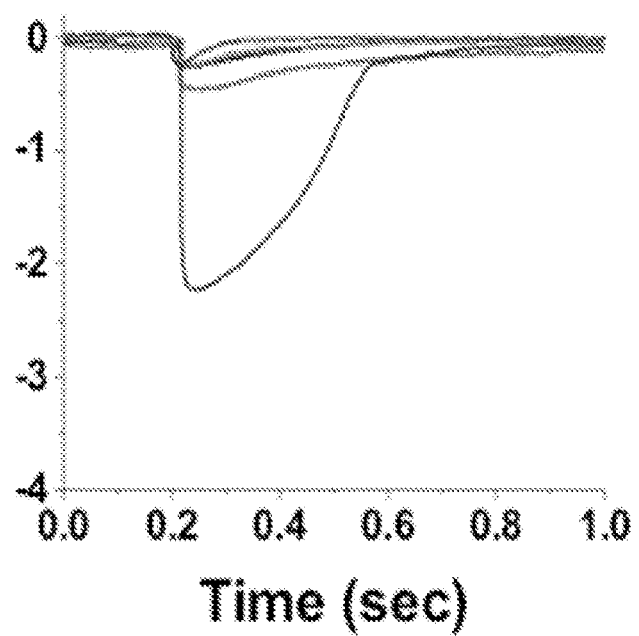

FIGS. 5A and 5B show the effect of eMCO1 (i.e., presence of mCherry on MCO1 function measured by cellular activity. Inward current profiles in HEK cells measured by Port-a-Patch automated Patch clamp electrophysiology. FIG. 5A shows photocurrent measured at white light intensity of 0.02 mW/mm$^2$ in cell transfected with mGluR6-eMCO1 (mGluR6-MCO1-mCherry).

FIG. 5B depicts photocurrent measured at white light intensity of 0.02 mW/mm$^2$ in cell transfected with mGluR6-MCO1.

Figure 6A:
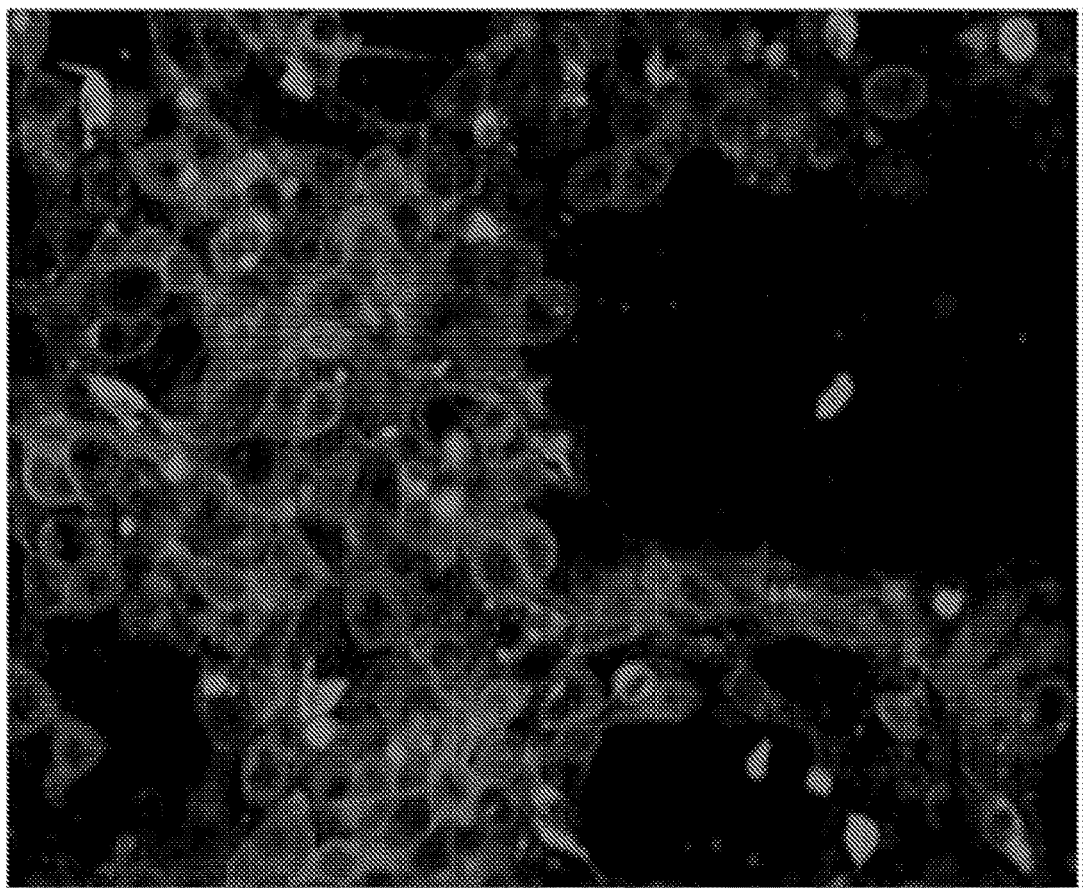

FIGS. 6A and 6B illustrate functioning of Multi-Characteristics Opsin (MCO2). FIG. 6A shows Fluorescence upon lipofection of MCO2-mCherry into HEK293 cells. FIG. 6B shows Inward current in MCO2-expressing cells in response to light (average intensity: 0.024 mW/mm2) measured by Patch-clamp electrophysiology.

FIGS. 7A and 7B illustrate vmGluR6eMCO1 transfection of cells. FIG. 7A depicts Three-dimensional reconstruction of vMCO1-mCherry (vmGluR6eMCO1) expression in HEK 293 cells, scale bar: 30 FIG. 7B shows Three-dimensional reconstruction of vMCO1-mCherry (vmGluR6eMCO1) expression in Whole retinal cup, scale bar: 0.8 mm.

FIGS. 8A and 8B show the patch-clamp recording of eMCO1 transfected retina. FIG. 8A shows eMCO1 expression in the cells of mice retina explant. FIG. 8B shows Inward photocurrent induced by light pulse (100 ms) train.

Figure 9A:
Figure 9B:
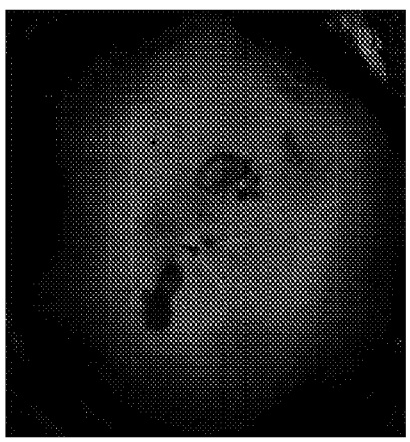
Figure 9C:
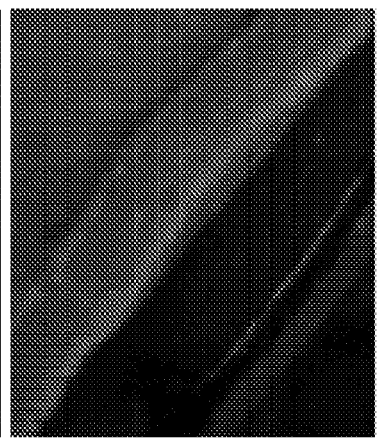
Figure 9D:
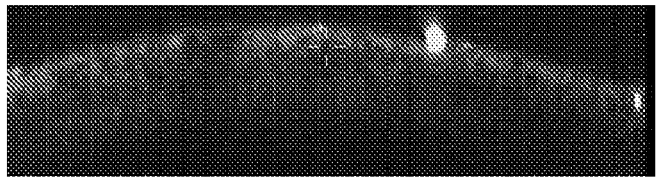
Figure 9E:
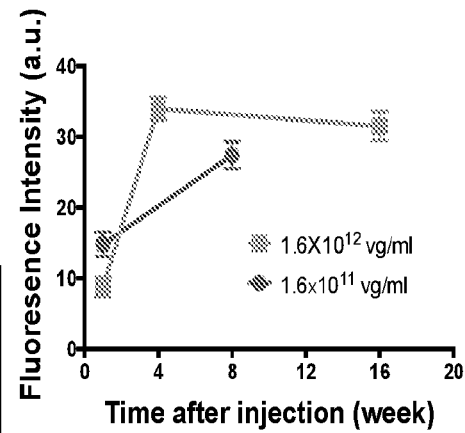
Figure 9F:
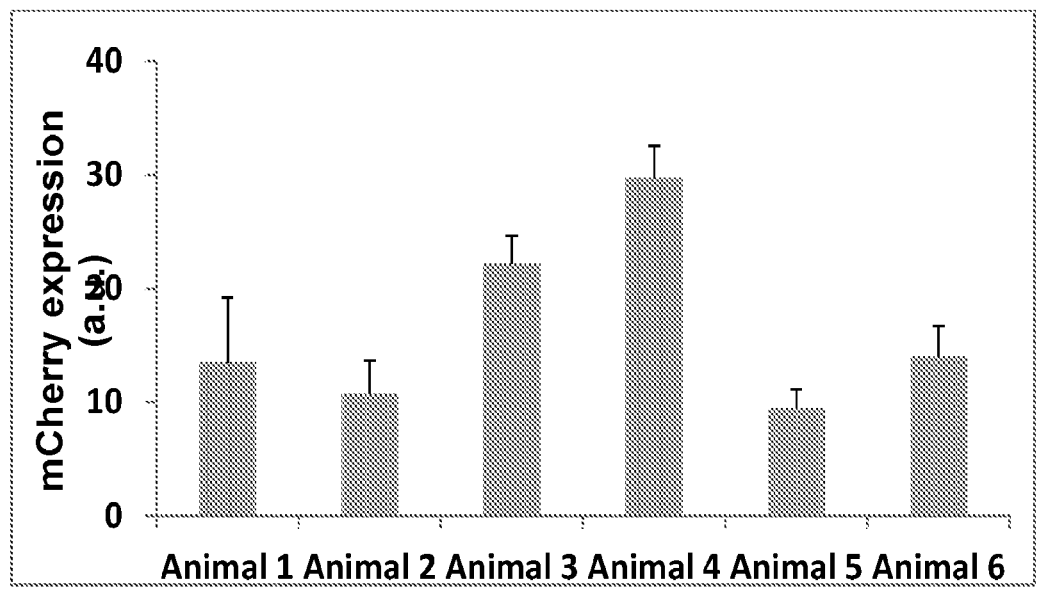

FIGS. 9A-9F show dose and time dependent layer-specific expression of eMCO1 in rd10 mice after vmGluR6eMCO1 injection. FIG. 9A shows Fluorescence confocal image of rd10 mouse retina cup after 1 week of intravitreal vmGluR6eMCO1 injection of FIG. 9B shows Fluorescence confocal image of rd10 mouse retina cup 8 weeks after intravitreal injection of vmGluR6eMCO1. Scale bar: 200 FIG. 9C shows Confocal fluorescence image of folded-edge of retinal cup transfected with vmGluR6eMCO1 at dose of $1.6 \times 10^{11}$ VG/ml. Scale bar: 100 FIG. 9D shows Cross-sectional view of vmGluR6eMCO1 expression in retina 16 weeks after intravitreal injection at dose of $1.6 \times 10^{12}$ VG/ml. Scale bar: 50 FIG. 9E shows Kinetics of eMCO1 expression in rd10 mice retina at two different doses of vmGluR6eMCO1. Average±SD. FIG. 9F shows Inter-animal variation of MCO1-mCherry (eMCO1) expression (after background subtraction) in retina of rd10 mice 16 weeks after transfection at dose of $1.6 \times 10^{12}$ VG/ml. Average+SD. * p<0.01 vmGluR6eMCO1 injected vs. non-injected.

Figure 10C:
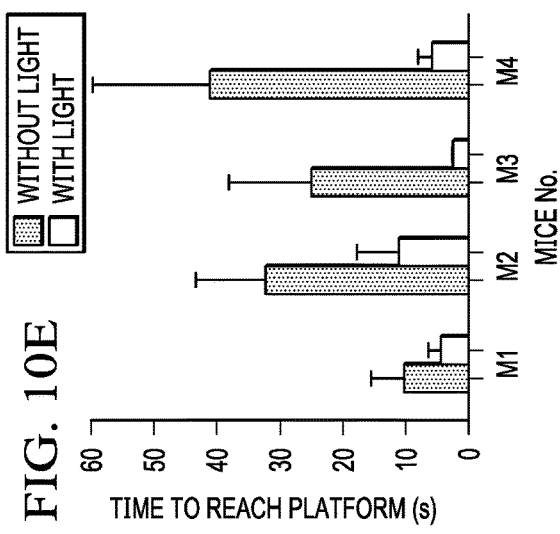
Figure 10E:
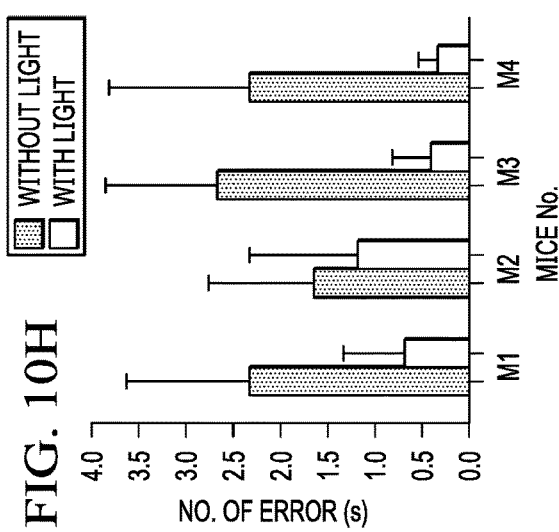
Figure 10D:
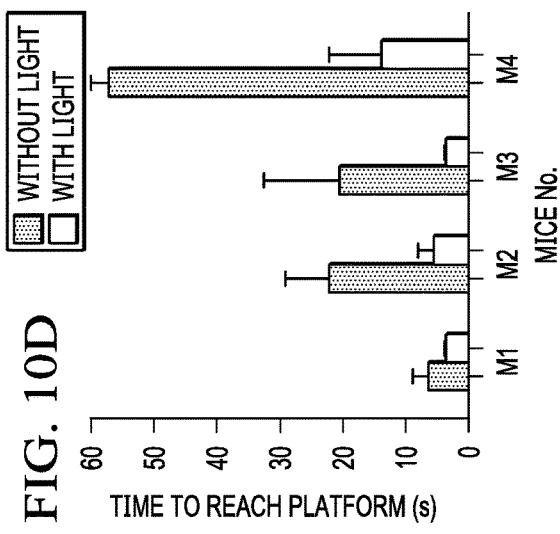
Figure 10G:
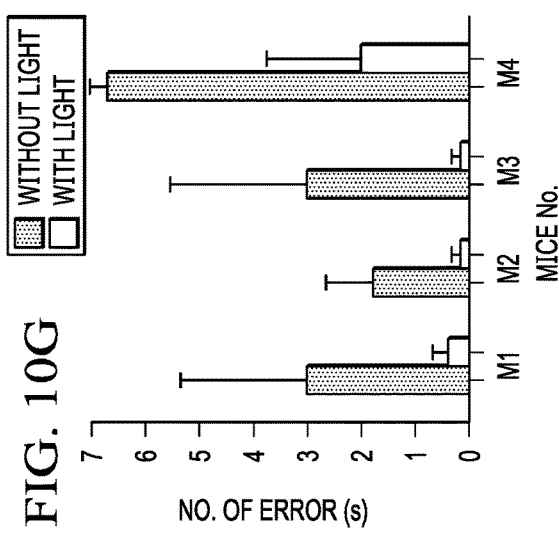
Figure 10F:
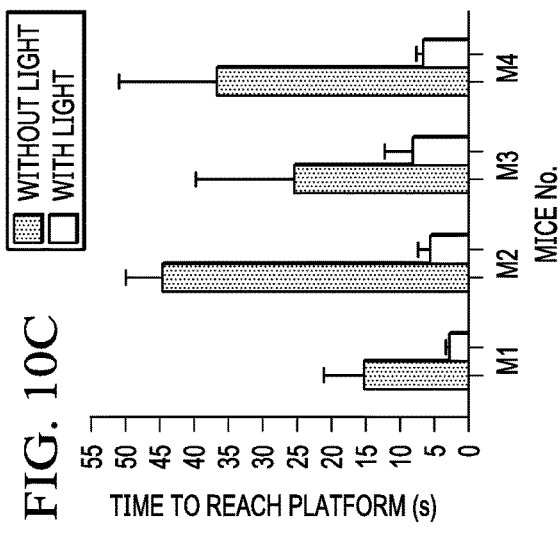
Figure 10H:
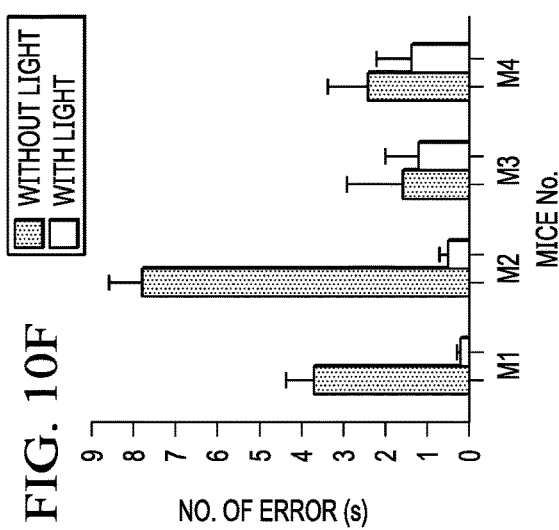

FIGS. 10A-10H show visually guided improvement in rd10 mice behavior in radial water maze. FIG. 10A shows Time-lapse images of visually guided rd10 mice behavior in radial water maze with white LED light before intravitreal vmGluR6eMCO1 injection. FIG. 10B shows Behavior of rd10 mouse with LED light ON six weeks after vmGluR6eMCO1 injection. FIG. 10C shows Latency to find the platform by the vmGluR6eMCO1 treated rd10 mouse, with and without light, dropped at center of the maze. Average ±SEM. N=5 for each mouse. FIG. 10D depicts Latency to find the platform by the vmGluR6eMCO1 treated rd10 mouse, with and without light, dropped at side arms-2 & 4 of the maze. Average ±SEM. N=5 for each mouse. FIG. 10E depicts Latency to find the platform by the vmGluR6eMCO1 treated rd10 mouse, with and without light, dropped at edge arm-3 of the maze. Average ±SEM. N=5 for each mouse. FIG. 10F shows Number of error arms traversed by the vmGluR6eMCO1 treated rd10 mouse dropped at center before finding the platform in presence and absence of light. Average ±SEM. N=5 for each mouse. FIG. 10G shows Number of error arms traversed by the vmGluR6eMCO1 treated rd10 mouse dropped at side arm before finding the platform in presence and absence of light. Average ±SEM. N=5 for each mouse. FIG. 10H shows Number of error arms traversed by the vmGluR6eMCO1 treated rd10 mouse dropped at edge before finding the platform in presence and absence of light. Average ±SEM. N=5 for each mouse.

Figure 11A:
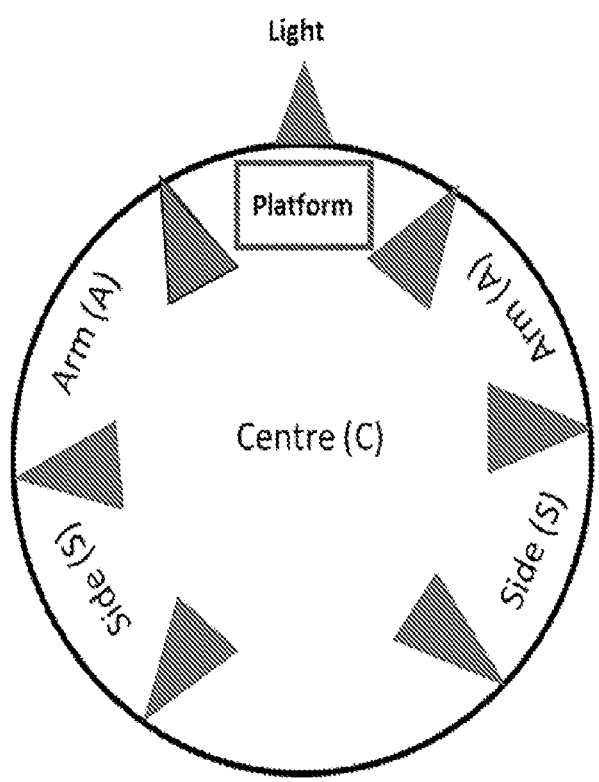
Figure 11B:
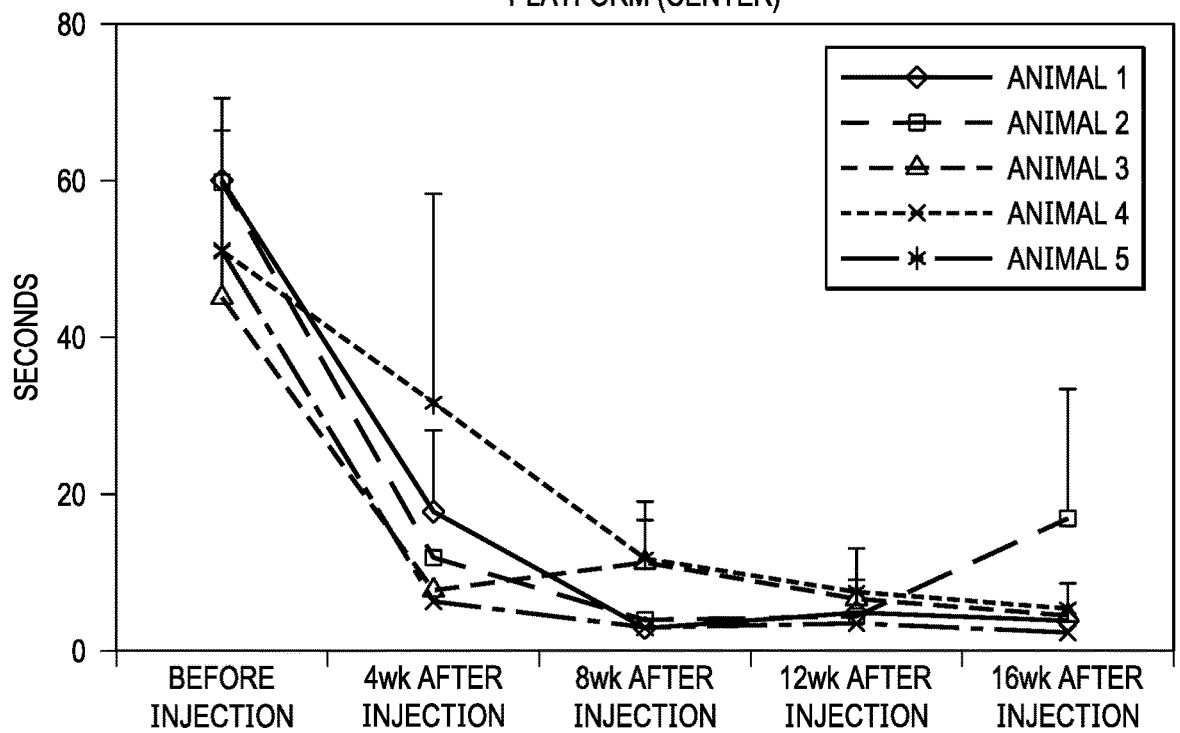
Figure 11C:
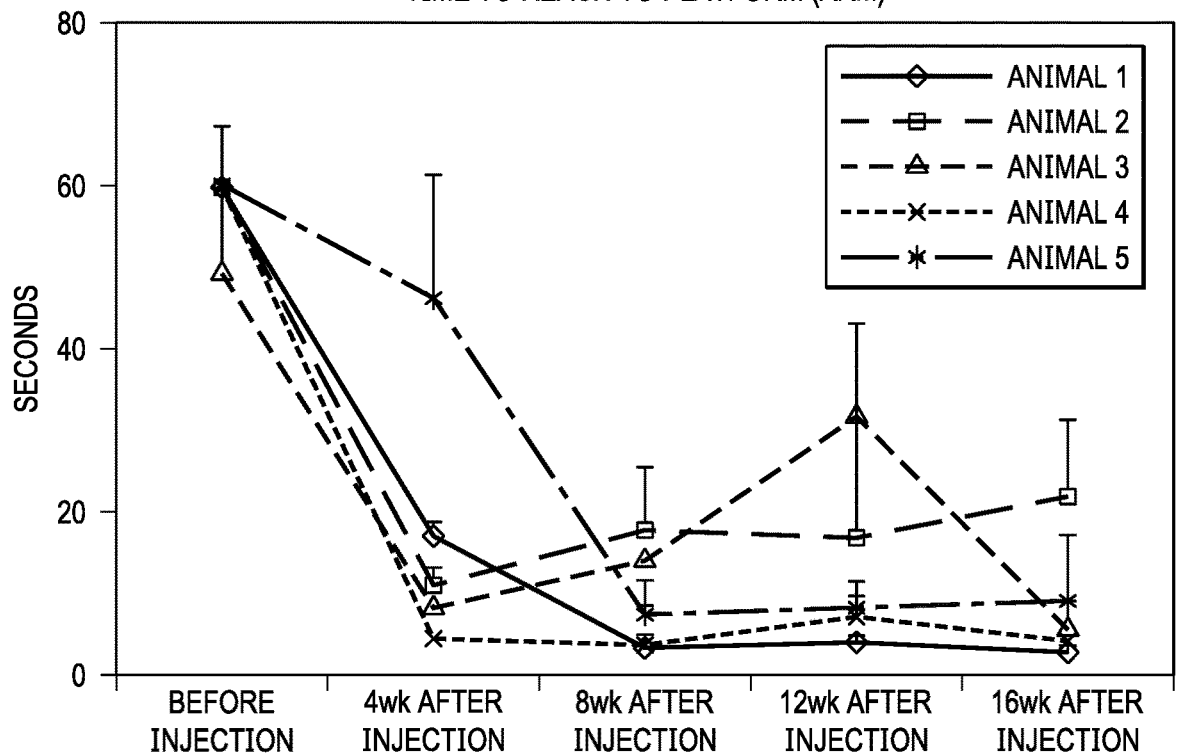
Figure 11D:
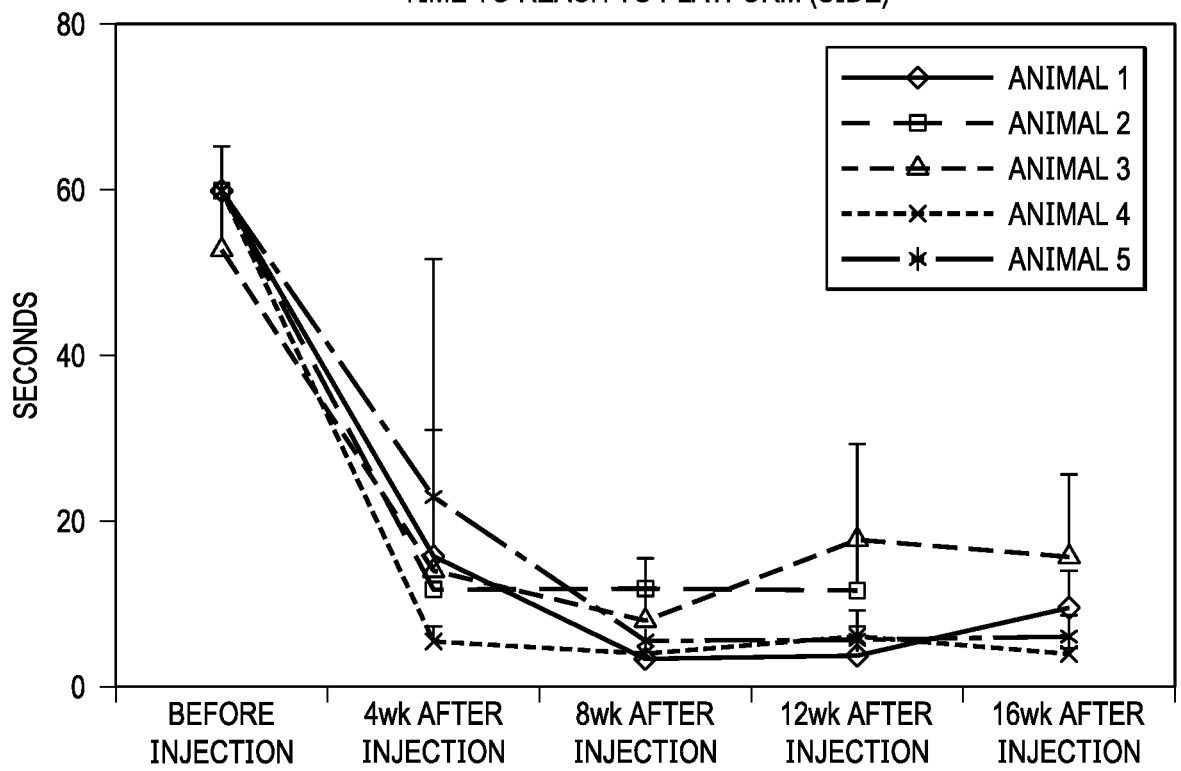

FIGS. 11A and 11B show longitudinal study of visually guided improvement in rd10 mice behavior in radial water maze. FIG. 11A depicts Schematic of the radial-arm water maze used to test improvement in visually-guided behavior of vmGluR6eMCO1 injected rd10 mice. FIG. 11B shows the Time to reach platform by the rd10 mice from center of the maze (light intensity: 0.007 mW/mm2) before vmGluR6eMCO1 injection and as a function of post-injection period. N=5; Average ±S.D. *P<0.05. FIG. 11C shows the Time to reach platform by the rd10 mice from near arm of the maze (light intensity: 0.014 mW/mm$^2$) before vmGluR6eMCO1 injection and as a function of post-injection period. N=5; Average ±S.D. *P<0.05. FIG. 11D plots the Time to reach platform by the rd10 mice from side arm (light intensity: 0.004 mW/mm$^2$) before vmGluR6eMCO1 injection and as a function of post-injection period. N=5; Average ±S.D. *P<0.05.

Figure 12:
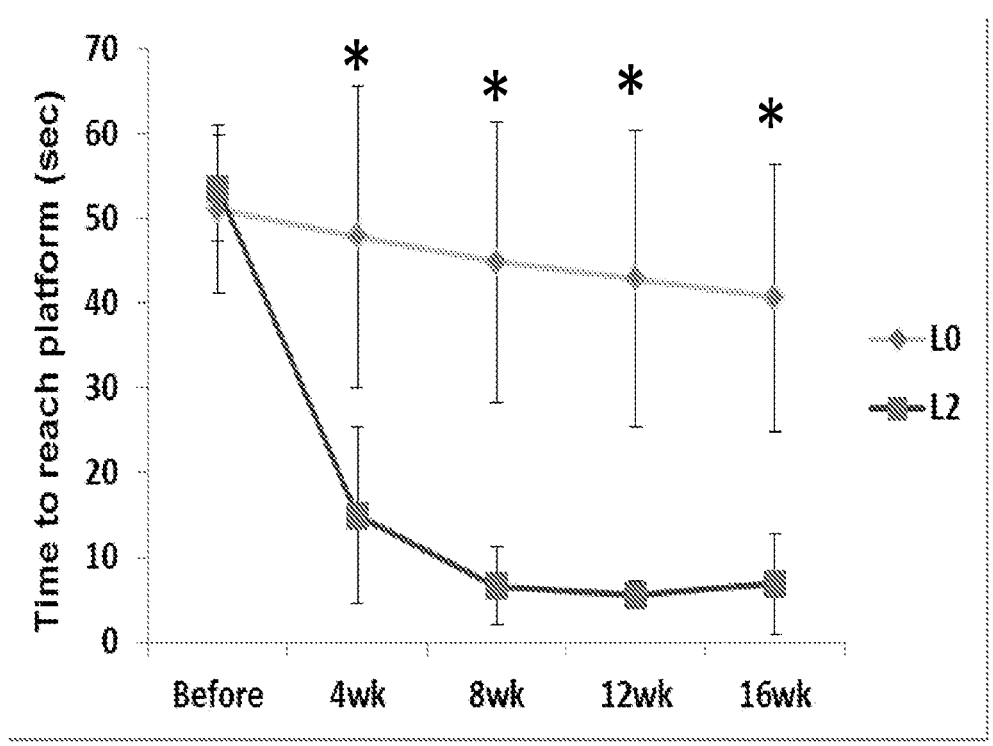

FIG. 12 shows the Light-intensity dependence of improvement in rd10 mice behavior in radial water maze. Comparison of time to reach platform from center of the maze between two different light intensities as a function of post-injection period. Average ±S.D. *P<0.01. L0=0.0005 mW/mm$^2$; L2=0.007 mW/mm$^2$. Bright ambient level is 0.01 mW/mm$^2$.

Figure 13A:
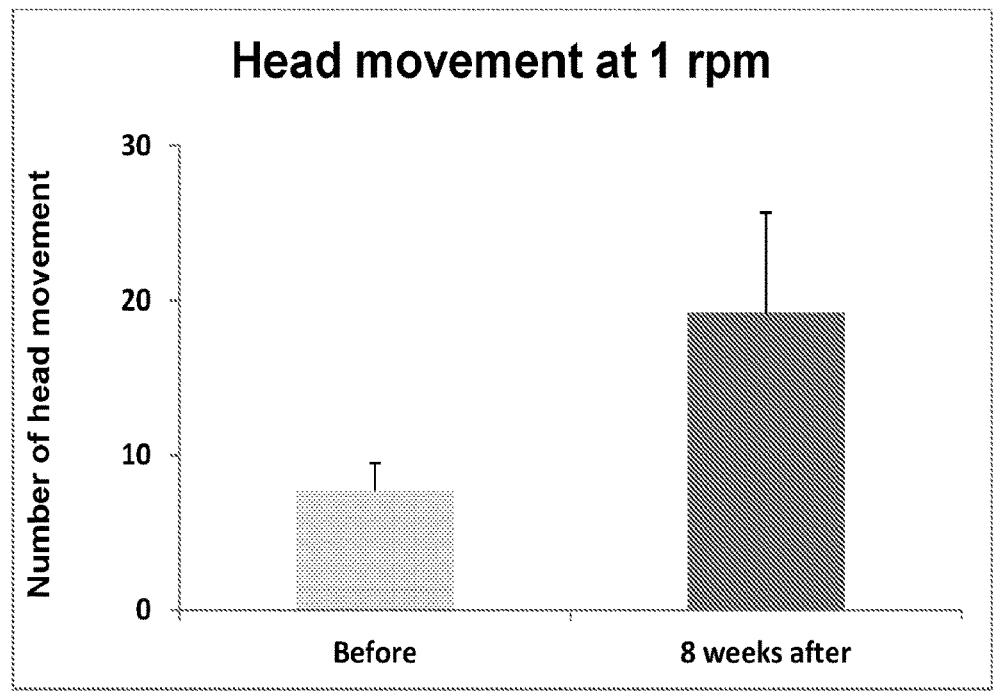
Figure 13B:
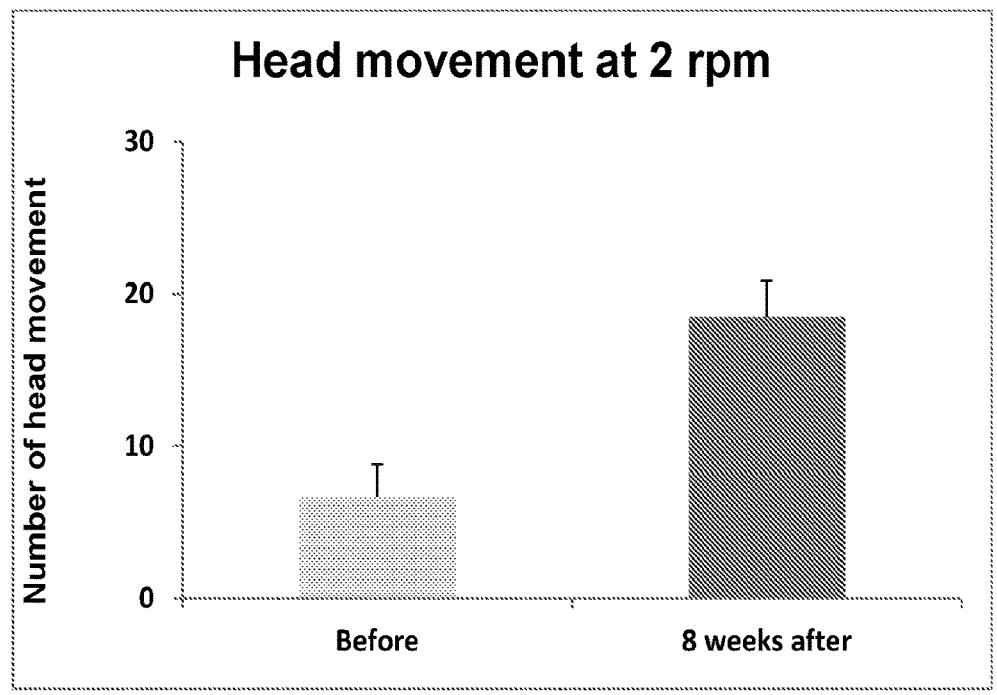

FIGS. 13A and 13B show optokinetic assessment of rd10 and MCO-sensitized rd10 mice. FIG. 13A shows Quantitative comparison of number of head movement of rd10 mice before and 8 weeks after vmGluR6eMCO1 injection at speed of rotation of the vertical stripes at 1 rpm. N=4 mice. Average+SD. *p<0.05. The light intensity at the center of the chamber is 0.001 mW/mm$^2$. FIG. 13B shows Quantitative comparison of number of head movement of rd10 mice before and 8 weeks after vmGluR6eMCO1 injection at speed of rotation of the vertical stripes at 2 rpm. N=4 mice. Average+SD. *p<0.05. The light intensity at the center of the chamber is 0.001 mW/mm$^2$.

FIG. 14 shows viability of eMCO1 sensitized retinal cells after chronic light exposure. FIG. 14A shows that Similar to the wild-type (non-blind) mice, vmGluR6eMCO1-treated rd10 mice avoid bright light by staying away and blocking light (via creating a heap out of bedding material, as shown in the arrow). FIG. 14B shows Fluorescence image of retina stained with Caspase-3 (green) for vmGluR6eMCO1-treated rd10 mouse 4 weeks after 8-hr/day illumination of white light (intensity: 0.1 mW/mm$^2$). FIG. 14C shows Fluorescence image of retina stained with Caspase-3 (green) for wild-type mouse 4 weeks after 8-hr/day illumination of white light (intensity: 0.1 mW/mm$^2$). FIG. 14D shows Quantitative comparison of % apoptotic retinal cells between wild type and vmGluR6eMCO1 treated rd10 mice. 0% apoptotic cells in inner nuclear layer of vmGluR6eMCO1 treated rd10 mice.

Figure 15A:
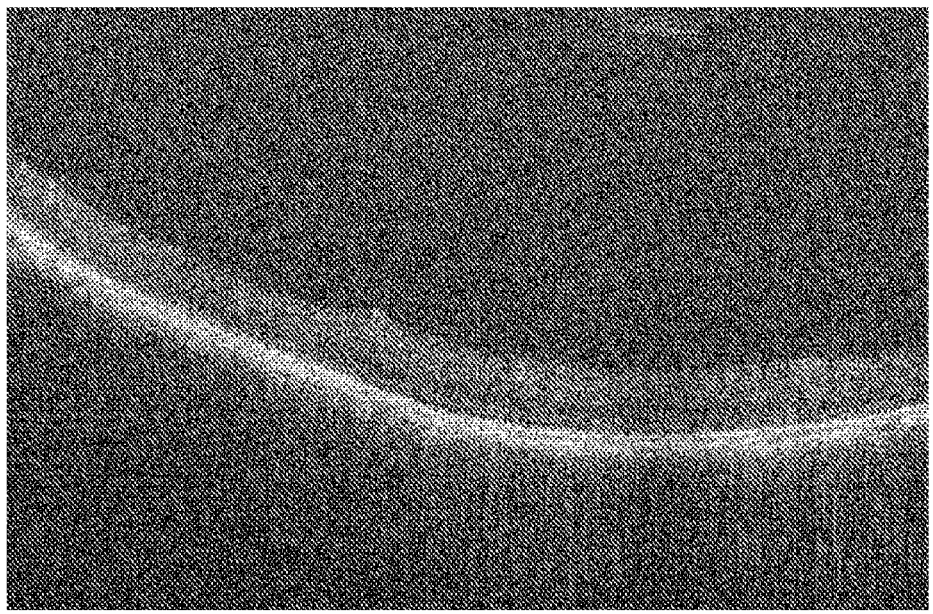
Figure 15B:
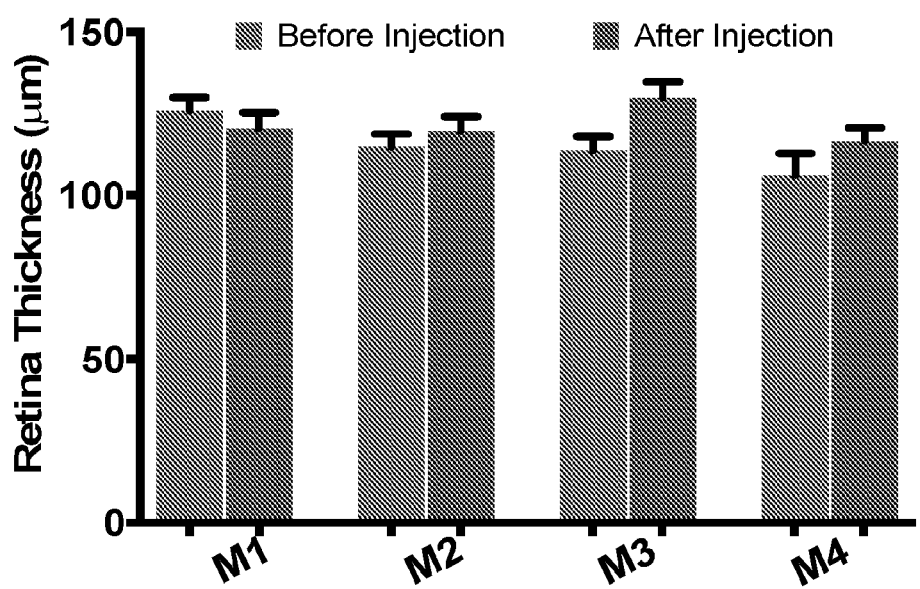

FIGS. 15A and 15B show results of evaluation of structural integrity of retina after vmGluR6eMCO1 injection in rd10 mice. FIG. 15A shows an OCT image of rd10 mice retina after vmGluR6eMCO1 injection. FIG. 15B shows the Comparison of retinal thickness of 4 different rd10 mice before and 1 week after injection. N=10 B-scans/mice. Average+SD.

Figure 16A:
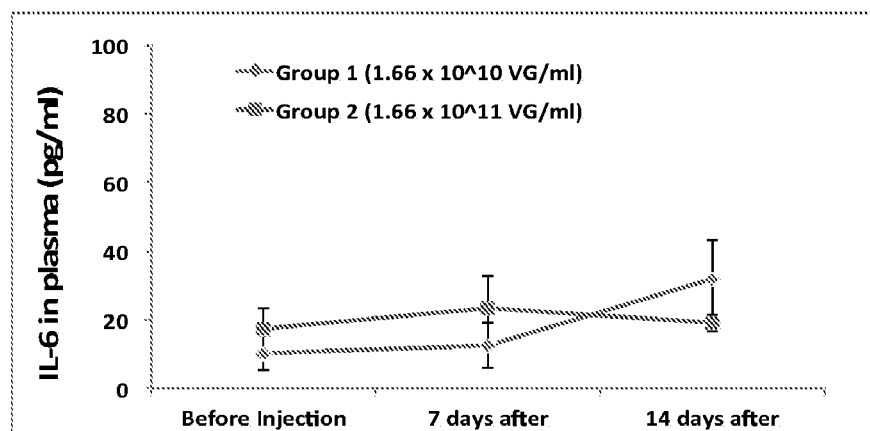
Figure 16B:
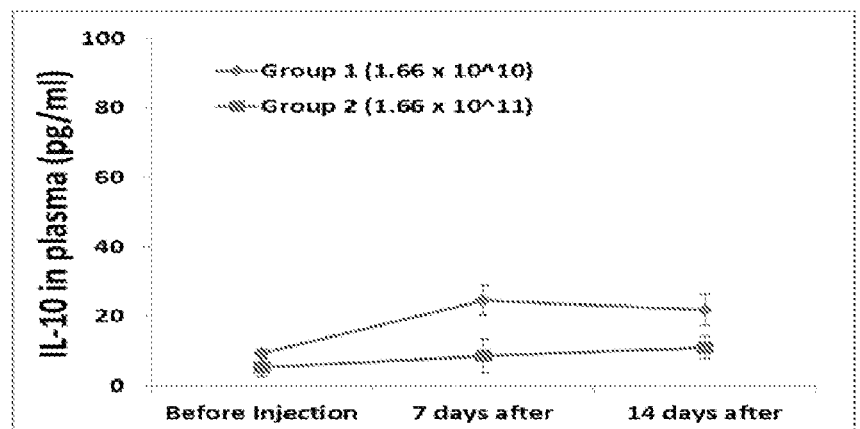
Figure 16C:
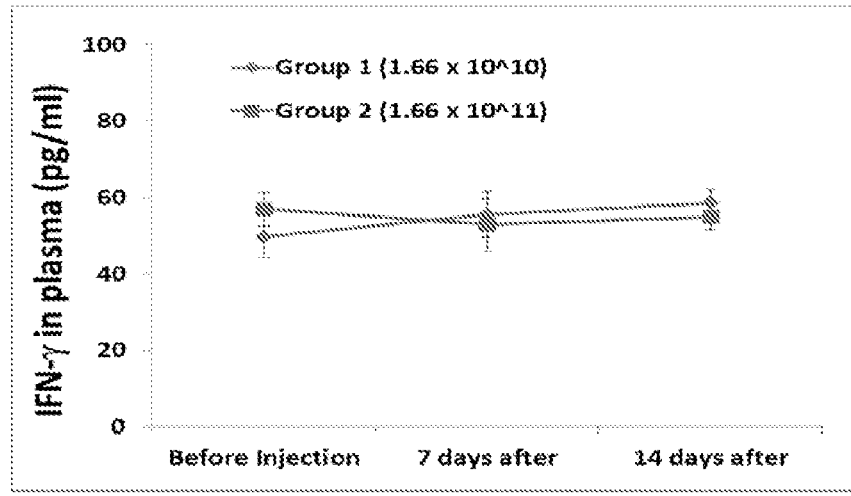

FIGS. 16A-16C show results of immune-toxicity in vmGluR6eMCO1 injected rd10 mice. FIG. 16A shows Quantitative comparison of IL-6 (pro-inflammatory marker) in plasma between group-1 ($1.6 \times 10^{10}$ VG/ml) and group-2 ($1.6 \times 10^{11}$ VG/ml) before and after 7 and 14 days of vmGluR6eMCO1 injection. N=5 mice/group. Average ±SD. FIG. 16B shows Quantitative comparison of IL-10 (anti-inflammatory marker) in plasma between group-1 ($1.6 \times 10^{10}$ VG/ml) and group-2 ($1.6 \times 10^{11}$ VG/ml) before and after 7 and 14 days of vmGluR6eMCO1 injection. N=5 mice/group. Average ±SD. FIG. 16C shows Quantitative comparison of IFN-Y (pro-inflammatory marker) in plasma between group-1 ($1.6 \times 10^{10}$ VG/ml) and group-2 ($1.6 \times 10^{11}$ VG/ml) before and after 7 and 14 days of vmGluR6eMCO1 injection. N=5 mice/group. Average ±SD.

Figure 17:
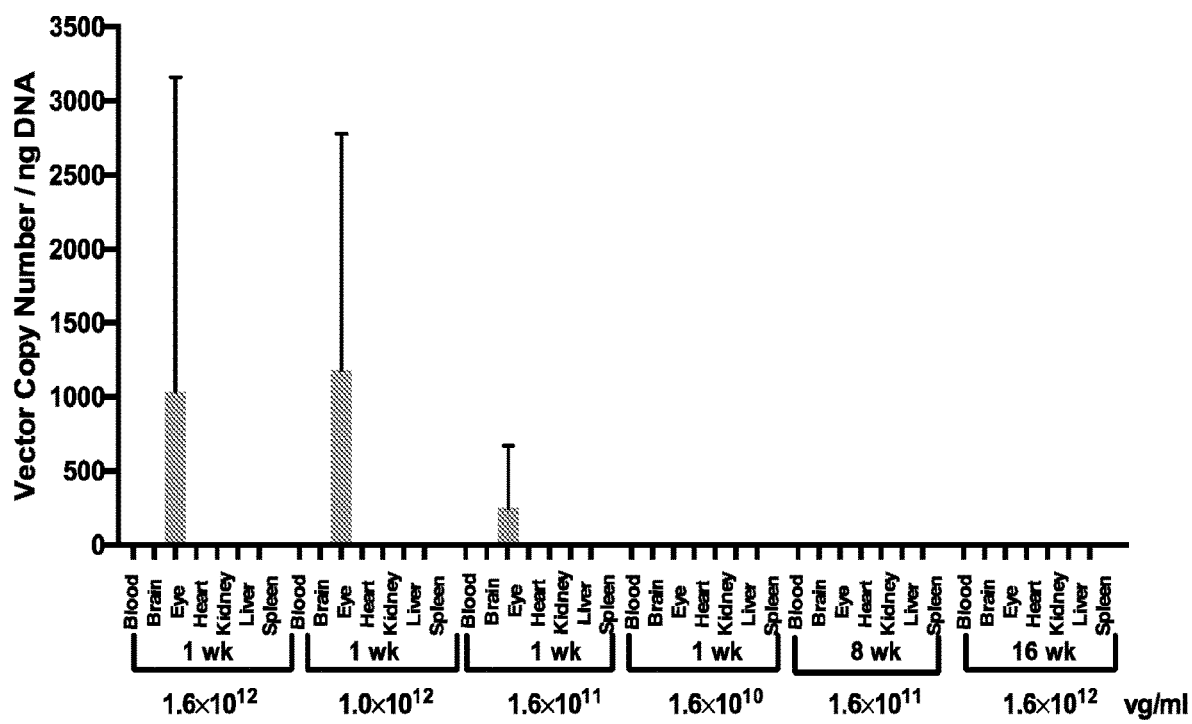
Figure 18A:
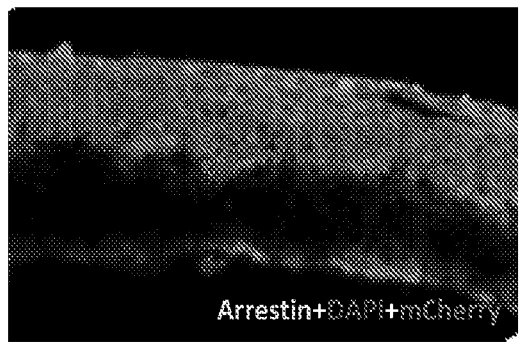
Figure 18D:
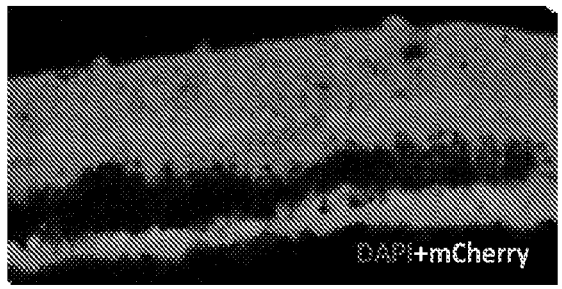
Figure 18B:
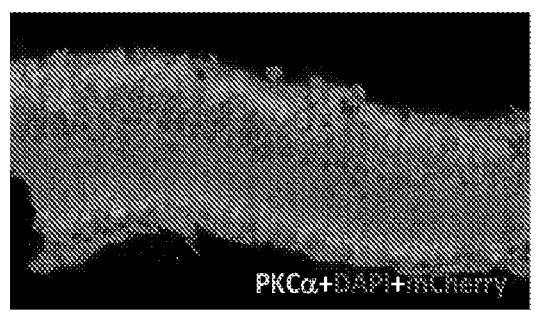
Figure 18E:
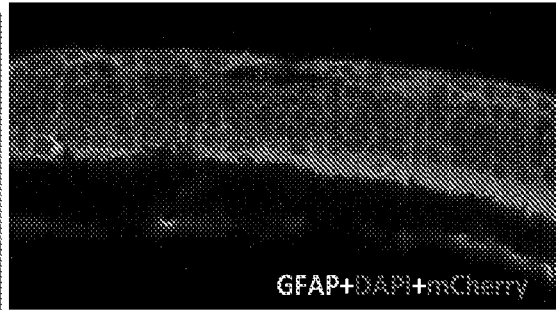
Figure 18C:
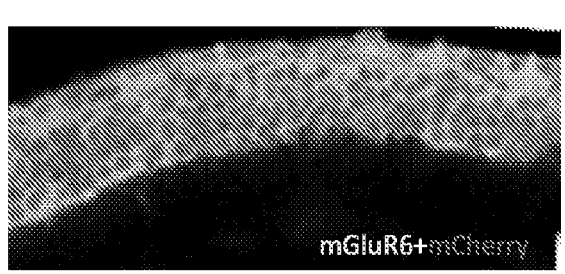
Figure 18F:
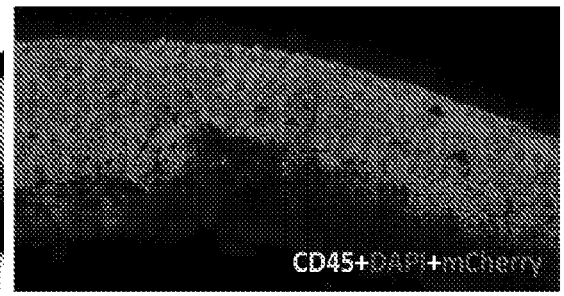

FIG. 17 shows biodistribution of AAV2 packaged Multi-Characteristics Opsin (vmGluR6eMCO1). QPCR detection of vector sequences in rd10 mice at different doses and post-injection period very small or non-detectable quantities of vector DNA in tissues outside of the treated eyes. N=5 mice/dose/time-point, FIGS. 18A-18F show immunohistochemistry of vmGluR6eMCO1 injected rd10 mice eye. FIG. 18A shows that MCO1-mCherry (eMCO1) (red) is selectively targeted and expressed in INL of rd10 mice 8 wks after intravitreal injection of vmGluR6eMCO1. The absence of arrestin (green) suggests a complete loss of photoreceptors. FIG. 18B shows PKCα stain (green) in rod bipolar cells expressing mCherry (red, intrinsic) in rd10 mice 8 wks after intravitreal injection of vmGluR6eMCO1. FIG. 18C shows mGluR6 stain (green) in ON bipolar cells expressing mCherry (red) in rd10 mice 8 wks after intravitreal injection of vmGluR6eMCO1. FIG. 18D shows mCherry (green-immunostained) expression in rd10 retina 8 wks following intravitreal delivery of vmGluR6eMCO1 to rd10 mice. FIG. 18E shows that GFAP (green) in rd10 mice 18 wks after intravitreal injection of vmGluR6eMCO1 as reported in photoreceptor degenerated retina. FIG. 18F shows no CD45 (green) expression suggesting no immune cells in rd10 mice 8 wks after intravitreal injection of vmGluR6eMCO1.

DETAILED DESCRIPTION OF THE INVENTION

Modulation of cellular activities by electrical and other means has enabled quantitative evaluation of cellular characteristics and changes associated with disease progression. Opsins (light-sensitive ion-channel proteins) in combination with light have been used for modulation of cellular activity. This has led to better understanding of cellular or network function and has potential for therapeutic applications including vision restoration, as well as for drug screening.

Since higher order neurons are still intact in degenerated retina, several stimulation methods target the higher order neurons, e.g. Bipolar cells and retinal Ganglion cells, which carry the visual information to the visual cortex. While direct electrical stimulation approaches require mechanical contact of electrodes the retinal cells, indirect stimulation approaches such as optogenetic stimulation does not necessitate such physical contact. Thus, the indirect methods provide clear advantage of being non-intrusive. In addition, cellular specificity and high (single cell) resolution can be achieved while using optogenetic stimulation.

In order to achieve optogenetic stimulation of retinal neurons, the cells are generally transfected by a virus to express opsin (light-sensitive molecular ion-channel), which gets activated, thus depolarizing the opsin-expressing cells when illuminated by light of specific visible wavelength, characteristics of the opsin. For example, retinal cells expressing Channelrhodopsin-2 (ChR2) are sensitive to blue light. Various light-activated ion channels (opsins) have been developed to either enhance photosensitivity of cells, or to be activated by different wavelengths of visible light. In order to be activated by broadband visible light, complex of three opsins (ChR2 for blue, C1V1 for green, and ReaChR for red photosensitivity) has been delivered to cells by chemical or physical method. However, such large complex cannot be packaged into safe viral vectors (i.e. Adeno-Associated Virus). Further, use of chemical or physical method for delivery is less efficient and/or compromises cell viability, thus limiting their ready usefulness.

The opsins developed and utilized so far for vision restoration, when stimulated by light do not produce characteristic photoreceptor-rod signal, i.e., the voltage signal do not have slower depolarizing phase after initial fast response. Therefore, effective optogenetic vision restoration at low light level has not been shown until the present invention.

Since the opsins employed so far for vision restoration require light intensity above ambient light level to stimulate the opsin-sensitized cells, external active stimulation devices has been designed (2) to stimulate opsin-sensitized retinal neurons in vivo.

Vision restoration by optogenetics or other gene therapy methods has been proposed in humans by delivery of opsin or other genes via viral means (e.g. recombinant adeno-associated virus, rAAV) in to vitreous of the eye. However, due to thick inner limiting membrane (ILM) that exists in humans (3), successful delivery of therapeutic gene by rAAV alone is questionable.

Advantages of the present approach include the fact that it produces characteristic photoreceptor-rod signal, and does not require external active stimulation devices, thus avoiding many obstacles that are or will be encountered by existing opsin-based approaches; thus the present invention is applicable for the restoration of vision lost due to retinal degenerative diseases. Further advantage of the present invention is that the method of delivering opsin/other therapeutic gene include a combination of rAAV and chemical agent that can transiently permeablize the inner limiting membrane of the human eye.

Currently, use of optogenetic sensitization of retinal cells combined with activation/inhibition has allowed the possibility of replacing the retinal implants, eliminating the requirement of placing electrodes near every single neuron for high resolution (4). Optogenetic stimulation provides high temporal precision (5-10) by introducing light-activatable molecular channels (e g channelrhodopsin-2, ChR2; halorhodopsin, NpHR) into cells by genetic targeting. In addition to higher temporal and spatial resolution, optogenetics has several advantages over electrical stimulation such as cellular specificity (e.g. spared cones, ganglion or bipolar cells) and minimal invasiveness (11). Light-induced activation of ChR2, a non-selective cation channel, results in depolarization of only those cells that express ChR2. Selective activation of neurons by ms-pulsed blue light has been demonstrated in culture (9), brain slices, as well as in small animals (12-15). This optogenetic activation method is very promising for controlling cellular activities in-vitro as well as in-vivo as it only requires light of moderate intensity (~0.1 mW/mm$^2$) that can be delivered from a light emitting diode (LED) or laser (5, 6).

The present disclosure provides several light-sensitive ion-channel molecules (Multi-Characteristics Opsins) made by synthetic means: (i) having high photosensitivity at multiple visible wavelengths, (ii) with plasmid size small enough to be packaged into safe Adeno Associated Virus. The invention also includes isolated nucleic acid sequences that encode light-sensitive ion-channels of the invention, and constructs that comprise such nucleic acid sequences. In some embodiments MCOs that find use the methods disclosed herein comprise amino acids as shown in Tables 1-4, 7 and as represented by SEQ ID NOS: 1, 3, 5, 7, or 11. In some embodiments the MCO has at least around 70, or 75, or 80, or 85 or 90 or 95, or 96 or 97, or 98 or 99% identity with a sequence as shown in SEQ ID NOS: 1, 3, 5, 7, or 11, wherein said MCO has the photosensitivity characteristics of SEQ ID NOS: 1, 3, 5, 7, or 11. In some embodiments, the MCO is encoded by a nucleic acid as shown in Tables 1-4, 7 and as represented by SEQ ID NOS: 2, 4, 6, 8, or 12. In some embodiments the nucleic acids encoding the MCO have at least around 70, or 75, or 80, or 85, or 90, or 95, or 96, or 97, or 98 or 99% identity with a sequence as shown in SEQ ID NOS: 2, 4, 6, 8, or 12, wherein said encoded MCO has the photosensitivity characteristics of SEQ ID NOS: 1, 3, 5, 7, or 11.

The nucleic acids encoding the MCO find use when incorporated into vectors for delivery to a patient in need thereof. In some embodiments the vectors are plasmids with appropriate promoters as is known in the art. In some embodiments the vectors are viral vectors. Viral vectors that find use in the methods disclosed herein include adenovirus vectors, adeno-associated virus vectors, and the like.

The invention in some aspects includes expression of Multi-Characteristics Opsins (MCOs) in cells in-vitro or in-vivo as well as methods for modulating cellular activities by these synthetic opsins.

One of the examples where MCO is used for treatment of disease is blindness caused by retinal degenerative diseases. Retinitis Pigmentosa (RP) and age-related macular degeneration (AMD) refer to disorders characterized by degeneration of photoreceptors in the eye, which hinders visual ability by non-functional neuronal activation and transmission of signals to the visual cortex (16-20). While AMD is the leading cause of new vision loss in ~15 million persons older than 65 years of age (21), the prevalence of RP is at least one million individuals world-wide (22, 23). RP is most often inherited as an autosomal recessive trait with large number of cases having this form of inheritance (18, 22, 24). Further, the degree of visual loss increases with ageing (25) and this is a major concern for our demographic changes towards elderly population.

Most of the current clinical treatments are primarily focused on slowing down the progression of the disease (26), as there is neither a cure that can stop the degeneration (27) nor a therapy, other than retinal prostheses, that can restore vision lost due to the degeneration (28). Partial restoration of vision involves invasive surgical procedure for retinal implants (29). Two different types of retinal implants are being developed: subretinal and epiretinal implants (30). The subretinal implants are positioned in the area of the retina where the photoreceptor cells reside, between the pigmented epithelium and the bipolar cells (31). These retinal prostheses have been successful in generating visual perception in blind subjects (32-34). The disadvantages of using such subretinal implants include (i) chronic damage of the implanted electrodes, and (ii) insufficient current produced by microphotodiode from the ambient light to stimulate adjacent neurons (35, 36). The epiretinal implants are placed in the area of the retinal ganglion cells (RGCs) and the device functions by stimulating the RGCs in response to input obtained from a camera that is placed outside of the eye or within an intraocular lens (36, 37). The disadvantages of epiretinal implants include (i) cellular outgrowth due to surgical implantation, and (ii) disordered stimulation pattern resulting from the electrical stimulation of both the axons and cell bodies of the RGCs (36). Besides being invasive in nature, these methods for restoration of vision in blind patients are based on non-specific cellular activation and have low spatial resolution due to low number of electrodes (higher number or density of electrodes requires more power, leading to damage of neural tissue by heat), and hence able to improve vision with low spatial resolution.

Optogenetic method has been employed for vision restoration in blind mice model either by non-specific stimulation of retina (38) or in a promoter-specific manner including Thy1 for RGCs (39-43), mGluR6 targeting ON bipolar cells (44, 45). Attempts have also been made for stimulation of RGCs by use of melanopsin (46) or photochemical genetics (47). Further, use of active light stimulation of chloride-channel opsin (Halorhodopsin) expressing in longer-persisting cone photoreceptors (48) has shown new promise for therapeutic intervention for restoration of vision (49). The re-sensitized photoreceptors have shown to drive retinal circuitry functions, activate cortical circuits, and mediate visually guided behaviors.

The earlier approaches for restoration of vision by optogenetic stimulation of retinal cells use opsins such as ChR2 (38) and others, which requires light intensities order of magnitude higher than ambient lighting conditions. Therefore, clinical success of such opsin molecules in ambient environment for vision restoration is not yet achieved. Further, use of external light source or device (e.g. LED array (50)) to activate such opsins can substantially damage the retinal cells in long-term usage. In addition, these opsins (used for vision restoration) have fast (millisecond) ON and OFF response to light pulses. i.e., when stimulated by light the opsin-sensitized cells do not produce characteristic photoreceptor-rod signal, i.e., the voltage signal do not have slower depolarizing phase after initial fast response to light pulse. Therefore, effective optogenetic vision restoration at ambient light level has not been shown until the present invention.

The disclosed invention includes methods of preparation of extremely-light sensitive ion-channels and different uses including vision restoration. In some aspect, expression of a specific MCO in cell produces a long-lasting inward current in response to white light similar to characteristic photoreceptor-rod signal. According to another aspect of the invention, the disclosed invention provides method for the use of synthetic opsins for vision restoration and other applications, wherein the amino acid sequence of the synthetic opsin is modified to provide enhanced light sensitivity, kinetics and ion-selectivity.

The results presented in this invention show efficient and stable in-vivo expression of MCO-reporter protein in mice retina after intravitreal injection of Adeno-Associated Virus carrying MCO. The results also demonstrated that the expression of MCO in retina of mouse model of retinal degeneration enables behavioral restoration of vision. The number of error arms and time to reach platform in a radial-arm water maze significantly reduced after delivery of MCO to the mice having degenerated retina. Notably, the improvement in visually guided behavior was observed even at light intensity levels orders of magnitude lower than that required for Channelrhodopsin-2 opsin (1).

According to yet another aspect of the invention, method of efficient restoration of vision in human is provided. The method include use of MCO which when expressed in retinal cells produces a slower depolarizing phase after initial response to white light similar to characteristic photoreceptor-rod signal, and delivery of the opsin to retinal cells in-vivo by Adeno-Associated Virus (AAV) carrying promoter-MCO-gene in eye, and/or in combination with pronaseE or Alpha-Aminoadipic Acid (AAA) for enhancing delivery efficiency to targeted retinal layer crossing the thick inner limiting membrane in humans.

The present disclosure will now be described more fully hereinafter with reference to the accompanying drawings, in which some exemplary embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art.

EXAMPLES

Example 1

FIG. 1A illustrates domain architecture of Multi-Characteristics Opsins (MCOs) with reporter protein. These MCOs were synthesized using A typical circular map with insertion of MCO gene cloned at the restriction sites is shown in FIG. 1B. The MCO genes were synthesized using DNA synthesizer and sequence was verified. Gel electrophoresis was carried out on amplified MCO1 gene (digested by restriction enzymes BamH I and Sal I with restriction fragments) using 0.8% agarose. Western blot was performed to confirm that the MCO is expressed in retinal cells. Retinas of mice were transfected using lipofectamine and expressed protein was extracted for western blot. Western blot was developed using primary (anti-mCherry polyclonal) antibody and secondary (Goat anti-Rabbit IgG) antibody with 1-step NBT/BCIP substrate.

Example 2

FIG. 2 shows Theoretical modeling of the three-dimensional arrangement of amino acid chains of Multi-Characteristics Opsins using web-based protocol (RaptorX). The RaptorX uses a conditional neural fields (CNF), a variant of conditional random fields and multiple template treating procedure to develop the following predicted structure of MCO. FIG. 2A shows the theoretical modeling of the three-dimensional arrangement of amino acid chains of Multi-Characteristics Opsin, MCO 1. FIG. 2B depicts the theoretical modeling of the three-dimensional arrangement of amino acid chains of Multi-Characteristics Opsin, MCO 2. FIG. 2C shows the theoretical modeling of the three-dimensional arrangement of amino acid chains of Multi-Characteristics Opsin, eMCO1. The expression of the gene and functioning of the MCO1 and eMCO1 was investigated. The eMCO1 was found to fold/express in membrane better, and therefore, function effectively as compared to MCO1. In the eMCO1 design, a special element between MCO1 and mCherry was placed, thus increasing the interaction between the MCO1 gene and mCherry, which makes mCherry play an active role in stabilizing the whole therapeutic molecule (eMCO1) in the membrane. Table-08 shows higher percentage of beta sheets and lower percentage of disordered structure (i.e. less prone to cleavage) in eMCO1 as compared to MCO1. Further, the presence of mCherry in eMCO1 serves as an indicator for determining efficacy of gene delivery to targeted tissue(s), and to determine presence of the opsin at different time points. In case of loss of opsin expression, re-injection of the opsin-gene for re-photosensitization of targeted cells can thus be carried out. For example, if visual ability is reduced or lost with time after initial improvement (by vMCO-1 injection), examination of mCherry expression in retina (by fundoscopy) will serve as a biomarker to determine if the vMCO-1 expression is lost (requiring reinjection). If the mCherry expression is intact (but the improvement in vision is lost/degraded), it will imply that the targeted retinal cells have lost connection with retinal ganglion cells, which carry visual information to visual cortex.

Example 3

For evaluating membrane trafficking of MCOs, the expression of MCOs in cell membrane (vs. cytoplasm) of transfected HEK293 cells was quantified using fluorescence intensity of reporter protein (mCherry). HEK293 cells were transfected with MCO constructs using lipofectamine 3000 (Life Technologies). After transfection, the HEK293 cells were maintained in DMEM/F-12 with 10% fetal bovine serum, 0.2 mg/mL Gentamycin in Petri dishes. The cultures were maintained at 37° C. in a 5% $CO_2$ humidified atmosphere. Cells were incubated for 48 hours after transfection to allow MCO expression. Visualization of the reporter (mCherry) fluorescence was carried out under epifluorescence microscope. The fluorescence images of HEK293 cells expressing eMCO1 (MCO1-mCherry) and MCO2-mCherry are shown in FIG. 3A and FIG. 6A respectively. Further, to quantify the relative expression of the eMCO1 in cell membrane and intracellular components, intensity profiles are plotted. FIG. 3B shows the Intensity of MCO1 reporter fluorescence along line across representative HEK293 cells transfected with mGluR6-eMCO1 (mGluR6-MCO1-mCherry). No significant intracellular (cytoplasmic) aggregation was observed implying effective trafficking of MCOs to the plasma membrane.

Example 4

To determine the light dependent inward photocurrent, the MCOs-expressing cells were exposed to pulses of light with intensity of 0.024 $mW/mm^2$. A single mode optical fiber coupled to a supercontinuum laser source (NKT Photonics) delivered the broadband light to the sample for optogenetic stimulation. A power meter (818-SL, Newport) was used to quantify the light intensity at the sample plane. The light pulse width was synchronized with the electrophysiology recording system, controlled by Axon Instruments Digidata system (Molecular Devices). Cells, transfected with MCOs were incubated with all-trans retinal (ATR, 1 µM) for 4 hours before conducting the patch clamp experiments.

The patch-clamp recording setup includes an inverted Nikon fluorescence microscope (TS 100) platform using an amplifier system (Axon Multiclamp 700B, Molecular Devices). Micropipettes were pulled using a two-stage pipette puller (Narshinghe) to attain resistance of 3 to 5 $\Omega S2$ when filled with a solution containing (in mM) 130 K-Gluconate, 7 KCl, 2 NaCl, 1 MgCl2, 0.4 EGTA, 10 HEPES, 2 ATP-Mg, 0.3 GTP-Tris and 20 sucrose. The micropipette-electrode was mounted on a micromanipulator. The extracellular solution contained (in mM): 150 NaCl, 10 Glucose, 5 KCl, 2 CaCl2, 1 MgCl2 was buffered with 10 mM HEPES (pH 7.3). Photocurrents were measured while holding cells in voltage clamp at −70 mV. The electrophysiological signals from the amplifier were digitized using Digidata 1440 (Molecular devices), interfaced with patch-clamp software (Clampex, Molecular Devices). For activation of MCO expressing cells, the light stimulation beam was delivered by the optical fiber. pClamp 10 software was used for data analysis. FIG. 4A shows representative inward current in MCO1-expressing cells in response to light (average intensity: 0.024 $mW/mm^2$) measured by Patch-clamp electrophysiology. The inward photocurrent was found to be order of magnitude higher in eMCO1 sensitized cells than that in the ChR2 expressing cells. Inward photocurrent (195 +32 pA) in eMCO1-sensitized cells at ambient light level (0.02 $mW/mm^2$) is above threshold for action potential (AP) unlike that in cells sensitized with ChR2 and White-Opsin (51). It may be noted that for a good fidelity of the light-evoked spiking of opsin-sensitized cells, faster response time is required. The on response time of ambient-light activatable eMCO1 (FIG. 4A) is measured to be 2.94+0.70 ms, which is similar to that measured for other fast-opsins (52). However, the on response time depends on the intensity of activation light and is known to increase as the light intensity decreases (53).

To obtain the activation spectrum of eMCO1, the inward photocurrent was measured using stimulation light at different wavelengths (with bandwidth: 30 nm). In FIG. 4B, we show the normalized activation spectrum of eMCO1. In addition to acting as stabilizer-biomarker, mCherry enhances the photo-induced current in the cells expressing eMCO1 by (i) better orientation-stabilization of eMCO1 across the membrane; and (ii) light emitted/re-emitted from the stabilizer-biomarker molecule enhance the activation of eMCO1. FIG. 5 shows Inward current profiles in HEK cells measured by Nanion Port-a-Patch automated Patch clamp electrophysiology. FIG. 5A shows photocurrent measured at white light intensity of 0.02 mW/mm$^2$ in cell transfected with mGluR6-eMCO1 (mGluR6-MCO1-mCherry). FIG. 5B depicts photocurrent measured at white light intensity of 0.02 mW/mm$^2$ in cell transfected with mGluR6-MCO1. The effect of presence of mCherry on enhanced MCO1 eMCO1 function is clearly demonstrated here. eMCO1 was found to have broad activation spectrum matching to the white ambient light.

The inward photocurrent in MCO2-expressing cells in response to light at the same average intensity (0.024 mW/mm$^2$) is shown in FIG. 6B. The peak photocurrent generated in eMCO1-cells at light intensity of 0.024 mW/mm$^2$ was −160 pA as compared to −320 pA in MCO2 expressing cells. While the on-rate of induced photocurrent in eMCO1 and MCO2 expressing cells in response to light did not differ significantly, the off-response (decay of current in absence of light) of MCO2 was found to be significantly slower than eMCO1 (FIG. 6B vs. FIG. 4A). In MCO2 expressing HEK293 cells, the threshold peak current for generating action potential (54) could be achieved at light intensity of 0.02 mW/mm$^2$, which is at the ambient light level. Therefore, ambient light is expected to generate sufficient photocurrent (for action potential) in MCO expressing retinal cells. FIG. 8 shows the patch-clamp recording of MCO1 transfected rd mouse retina. FIG. 8A shows eMCO-1 expression in the cells of mice retina explant. FIG. 8B shows Inward photocurrent induced by light pulse (100 ms) train. The spectral and intensity sensitivity combined with the fast kinetics and small size (allowing packaging by AAV) of eMCO1 makes it uniquely suitable for photosensitizing higher-order retinal neurons in subjects with retinal degeneration to enable vision restoration in ambient light environment.

Example 5

MCO1 and MCO2 plasmids were packaged in Adeno-associated virus (serotype 2) with mGluR6 promoter and mCherry reporter. The synthesized plasmids were cloned into pAAV MCS vector via its BamHI and Sail sites. AAV physical titers were obtained by quantitative PCR using primers designed to selectively bind AAV inverted terminal repeats. TCID50 assay was conducted according to ATCC protocol. Verification of purity of purified virus was confirmed by SDS/PAGE. FIG. 7A illustrates fluorescence image of HEK293 cells expressing mCherry, 2 days after transfection with AAV2-mGluR6-MCO1-mCherry (vmGluR6eMCO1). Robust expression was observed with no detectable change in morphology, confirm that transfected cells are healthy. For in-vivo transfection of rd10 mice, intravitreal injection of 1µl of AAV2-mGluR6-MCO1-mCherry (vmGluR6eMCO1), was carried out for targeted expression in ON bipolar cells. Uniformity of MCO expression was confirmed by the 3D reconstruction from the confocal mCherry-expression in z-slices of the whole retinal cup of rd10 mice injected with vMCO1 intravitreally (FIG. 7B).

Example 6

The rd10 mice (retinal degeneration 10, spontaneous missense point mutation in Pde6b) have a later onset and progressive retinal degeneration, closer to the human retinal degeneration phenotype. After anesthetization of the rd10 mice, AAV2-mGluR6-MCO1-mCherry (vmGluR6eMCO1) (1µl) solution (1.6×10$^{12}$ GC/ml) was injected by a sterilized needle of a Hamilton syringe inserted through the sclera into the vitreous cavity. The AAV2-mGluR6-MCO I-mCherry (vmGluR6eMCO1) solution was injected to both the eyes. The cornea was kept moist with a balanced salt solution during the entire surgical procedure. In-vivo transfection of vmGluR6eMCO1 in rd10 mouse retina was carried out for four different final doses of vmGluR6eMCO1. At different time points after vmGluR6eMCO1 injection, the mice in each group were euthanized and retina tissues harvested. Confocal fluorescence microscopy was carried out for analysis of eMCO1 expression in retina. To evaluate retention of the vmGluR6eMCO1, the reporter fluorescence expression level (fluorescence intensity) of transfected retina was evaluated using confocal microscope. At different time points after vmGluR6eMCO1 injection, the mice were sacrificed and retina was extracted and imaged by confocal microscopy. The vmGluR6eMCO1-transfected rd10 mice retina showed distinct expression of reporter (mCherry) on cell membrane in targeted cell layer. In contrast to significant expression in vmGluR6eMCO1-injected eyes, no characteristic mCherry expression (only background autofluorescence) was observed in PBS injected eyes monitored up to 16 weeks. Further, no significant increase in mCherry expression (only background autofluorescence) was observed 1 wk after injection for three different vmGluR6eMCO1 doses. eMCO1 expression was significantly higher at 4-8 wk after intravitreal injection of vMCO1 (FIG. 9B). In-vivo viral transfection was conducted for delivery of the eMCO1 to the bipolar cells in the retina of the rd10 mouse model. eMCO1 expression was found to be localized in targeted retinal cells (FIG. 9C).

FIG. 9D shows cross-sectional view of eMCO1 expression in retina 16 weeks after intravitreal injection at dose of 1.6×10$^{12}$ VG/ml. Furthermore, expression level was significant even after 4 months of injection. FIG. 9E shows kinetics of eMCO1 expression in rd10 mice retina at two different doses of vmGluR6eMCO1. FIG. 9F shows the inter-animal variation of MCO1-mCherry (eMCO1) expression (after background subtraction) in retina of rd10 mice 16 weeks after transfection of vmGluR6eMCO1 at dose of 1.6×10$^{12}$ VG/ml.

Example 7

For testing spatial memory and learning capabilities of vmGluR6eMCO1 treated rd10 mice towards light, a visual radial arm water maze was used (55). Briefly, mice are placed into the center of the maze and a platform is placed just below the water's surface at the end of one of the arms. The mice rapidly learn to determine the location of the platform by utilizing visual cues (LEDs emitting light with visible spectrum). The platform (in one of the arms) provided a reward to them where they can rest instead of having to swim. The time to reach platform and number of error(s) made before finding the platform was quantified for both light on and off conditions. Data (video) recording was stopped once the mice find the platform or before 60 sec of dropping the mice in water in order to prevent the mice from getting tired of swimming. The selection of dropping site (center, side, edge) was random for each mice and each trial. The exclusion criterion consists of mouse that does not swim (and floats). Visual acuity in this test was determined by measuring the latency to reach the platform, and the number of errors the mouse makes before reaching the platform as the quality of the visual stimulus (cue) degrades. At ~10 wks after birth, the rd10 mice were intravitreally injected with vmGluR6eMCO1 targeting the bipolar cells. The platform provides a reward where mice can rest instead of having to swim. Intravitreal injection of virus carrying mGluR6eMCO1 led to significant improvement in visually guided behavior of rd10 mice as assessed by radial-arm water maze assay. At ~8 weeks after birth, the rd10 mice, were intravitreally injected with AAV carrying mGluR6eMCO1 targeted to bipolar cells in retina. FIG. 10 shows visually guided improvement in rd10 mice behavior in radial water maze. FIG. 10A shows Time-lapse images of visually guided rd10 mice behavior in radial water maze with white LED light before intravitreal vmGluR6eMCO1 injection. FIG. 10B shows Behavior of rd10 mouse with LED light ON six weeks after vmGluR6eMCO1 injection. The distances and time traveled by the vmGluR6eMCO1-transfected rd10 mice before arriving at the platform were much shorter than the rd10 mice. FIG. 10C shows Latency to find the platform by the vmGluR6eMCO1 treated rd10 mouse, with and without light, dropped at center of the maze. Average ±SEM. N=5 for each mouse. FIG. 10D depicts Latency to find the platform by the vmGluR6eMCO1 treated rd10 mouse, with and without light, dropped at side arms-2 & 4 of the maze.

FIG. 10E depicts the latency to find the platform by the vmGluR6eMCO1 treated rd10 mouse, with and without light, dropped at edge arm-3 of the maze. In consistence with the latency to find the platform, the number of errors made by the vmGluR6eMCO1-transfected rd10 mice before they reached the platform is significantly smaller (<1) than that of the mice without transfection (>2) (56). FIG. 10F shows the number of error arms traversed by the vmGluR6eMCO1 treated rd10 mouse dropped at center before finding the platform in presence and absence of light. FIG. 10G shows Number of error arms traversed by the vmGluR6eMCO1 treated rd10 mouse dropped at side arm before finding the platform in presence and absence of light. Average ±SEM. N=5 for each mouse. FIG. 10H shows Number of error arms traversed by the vmGluR6eMCO1 treated rd10 mouse dropped at edge before finding the platform in presence and absence of light. Average ±SEM. N=5 for each mouse.

FIG. 11 shows longitudinal study of visually guided improvement in rd10 mice behavior in radial water maze. We collected data to determine visual acuity at baseline (pre viral transfection) and over time (every 4 wks for 4 months). FIG. 11A depicts Schematic of the radial-arm water maze used to test improvement in visually-guided behavior of vmGluR6eMCO1 injected rd10 mice. 4 wks after injection, all mice significantly restored their visually guided behavior that lasted through the 16 wks trial. The number of errors made by the vmGluR6eMCO1-transfected rd10 mice before they reached the platform is significantly smaller (<1) than that of the mice without transfection (>2) (56). In consistence with the number of error arms, the distances and time traveled by the vmGluR6eMCO1-transfected mice before arriving at the platform were much shorter than the rd10 mice (n=5 for both groups). FIG. 11B shows the Time to reach platform by the rd10 mice from center of the maze (light intensity: 0.007 mW/mm$^2$) before vmGluR6eMCO1 injection and as a function of post-injection period. N=5; Average ±S.D. *P<0.05. FIG. 11C shows the Time to reach platform by the rd10 mice from near arm of the maze (light intensity: 0.014 mW/mm$^2$) before vmGluR6eMCO1 injection and as a function of post-injection period. N=5; Average ±S.D. *P<0.05. FIG. 11D plots the Time to reach platform by the rd10 mice from side arm (light intensity: 0.004 mW/mm$^2$) before vmGluR6eMCO1 injection and as a function of post-injection period. N=5; Average ±S.D. *P<0.05.

Most importantly, the vmGluR6eMCO1-treated rd10 mice, when randomly placed in five different arms of the radial water maze in a single sequence, they could find the platform (in 6$^{th}$ arm) from all the other arms without a single error. Furthermore, the vmGluR6eMCO1-treated rd10 mice performed better in visually guided tasks even at low light intensities (0.005-0.01 mW/mm$^2$), comparable to ambient light levels. To determine the light intensity-dependence of improvement of behavior for the vmGluR6eMCO1-treated mice, the intensity of the diverging LED light was varied from 0.0005 to 0.03 mW/mm$^2$. The mean time taken by vmGluR6eMCO1-treated rd10 mice to reach the platform was <20 sec, at ambient light intensity level of 0.007 mW/mm$^2$. The behavioral scores were correlated with the light intensities and threshold for improvement in visually guided behavior was determined to be 0.004 mW/mm$^2$. FIG. 12 shows the Light-intensity dependence of improvement in rd10 mice behavior in radial water maze. Comparison of time to reach platform from center of the maze between two different light intensities as a function of post-injection period. This is the first time opsin-treated mice could perform significantly better at such low light levels. Earlier behavioral studies using ChR2-treated mice have utilized much higher light intensities, not suitable for practical application of optogenetics in vision restoration without use of active illumination sources.

Example 8

Because measurement of the optomotor response is commonly used to determine thresholds of the visual system in humans and animals (57, 58), we utilized this tool for evaluating improvement in visual performance of rd10 mice with vmGluR6eMCO1 sensitized retinas. The advantage of this method is that it does not require any previous training of the animal. Briefly, rd10 mouse was placed on a platform (in the center of a drum) surrounded by rotating stripes (FIG. 10). The optokinetic stimulation with varying speed was applied and average optomotor response and the score of the mice was measured. FIG. 13 shows optokinetic assessment of rd10 and vmGluR6eMCO1-sensitized rd10 mice. FIG. 13A shows Quantitative comparison of number of head movement of rd10 mice before and 8 weeks after vmGluR6eMCO1 injection at speed of rotation of the vertical stripes (0.07 cpd) at 1 rpm. The light intensity at the center of the chamber is 0.001 mW/mm$^2$. FIG. 13B shows Quantitative comparison of number of head movement of rd10 mice before and 8 weeks after vmGluR6eMCO1 injection at speed of rotation of the vertical stripes at 2 rpm. The light intensity at the center of the chamber is 0.001 mW/mm$^2$. Even at this low light intensity, the vmGluR6eMCO1-treated mice rotated its head in response to rotating stripes implying improved spatial visual acuity.

Example 9

Similar to the wild-type (non-blind) mice, vmGluR6eMCO1-treated rd10 mice were observed to avoid bright light by staying away and blocking light (FIG. 14).

Example 10

Figure 14A:
Figure 14B:
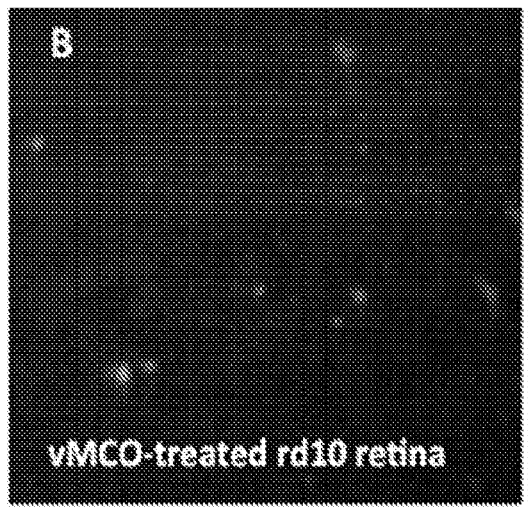
Figure 14C:
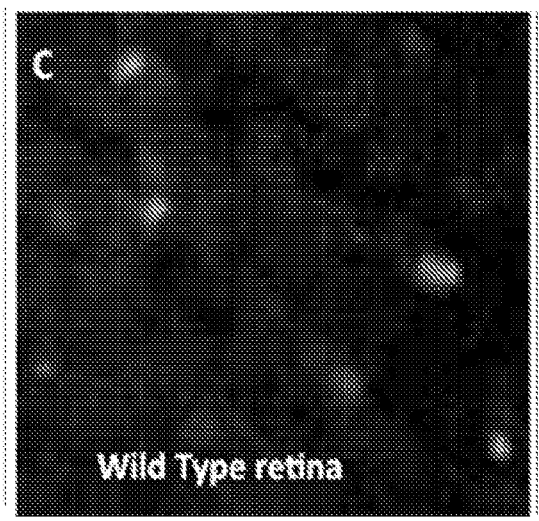
Figure 14D:
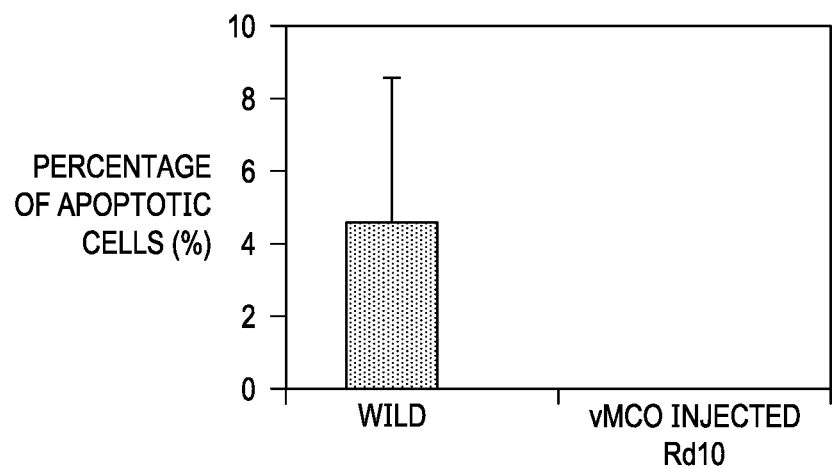

Chronic exposure of opsin transfected retinal cells to light may raise concern about their viability. Therefore, to evaluate any detrimental effect of light exposure on retinal cell viability, wild type and vmGluR6eMCO1-injected rd10 mice were exposed to white light with intensity (i.e. 0.1 mW/mm$^2$)~10 times higher than that of ambient light level (~0.01 mW/mm$^2$) for 4 weeks (8 hr/day). 4 weeks after light exposure, the vmGluR6eMCO1-transfected rd10 as well as wild-type (control) mice were sacrificed, and the retina tissue was harvested for immuno-histochemical analysis. The retina was immunostained with apoptotic markers and imaged using confocal microscopy. FIG. 14 shows viability of eMCO1 sensitized retinal cells after chronic light exposure. FIG. 14A shows that Similar to the wild-type (non-blind) mice, vmGluR6eMCO1 treated rd10 mice avoid bright light by staying away and blocking light (via creating a heap out of bedding material, as shown in the arrow). FIG. 14B shows Fluorescence image of retina stained with Caspase-3 (green) for vmGluR6eMCO1-treated rd10 mouse 4 weeks after 8-hr/day illumination of white light (intensity: 0.1 mW/mm$^2$). FIG. 14C shows Fluorescence image of retina stained with Caspase-3 (green) for wild-type mouse 4 weeks after 8-hr/day illumination of white light (intensity: 0.1 mW/mm$^2$). Quantitative comparison (FIG. 14D) shows that there is no significant cell death in either of the wild type or vmGluR6eMCO1-injected rd10 mice, indicating no compromise of cell viability under chronic light exposure. 0% apoptotic cells in inner nuclear layer of vmGluR6eMCO1-treated rd10 mice. Furthermore, since light-sensitivity of vmGluR6eMCO1-expressing cells significantly reduces the required light intensity for generating action potential, use of vmGluR6eMCO1 will minimize light-induced chronic damage to the retinal cells.

Example 11

Optical sectioning/imaging using SDOCT was carried out to monitor any changes in ocular structure due to intravitreal injection of vmGluR6eMCO1. SDOCT images of cornea, lens, and retina 1 wk after intravitreal vmGluR6eMCO1-injection in rd10 mice were compared to the images before injection. FIG. 15 shows results of evaluation of structural integrity of retina after vmGluR6eMCO1 injection in rd10 mice. FIG. 15A shows an OCT image of rd10 mice retina after vmGluR6eMCO1 injection. FIG. 15B shows the Comparison of retinal thickness of 4 different rd10 mice before and 1 week after injection. No detectable alteration to cornea, lens or retina (e.g. detachment) was observed after intravitreal injection of vmGluR6eMCO1. Image) was used to analyze the SDOCT images. Quantitative comparison of retinal thickness before and 1 wk after vmGluR6eMCO1 injection (FIG. 15D) shows no change in retinal thickness.

Example 12

Though gene therapy has been controversial for the last decade due to undesired side effects (59, 60), opsins (e.g. ChR2) are reported to be non-toxic, not generate immune response, and maintain stable cell membrane properties. Therefore, the health of the mice was monitored to confirm the safety of our approach. For immunotoxicity studies, blood was drawn from mice (N=5/dose) before and after intravitreal injection of two different doses (Group 1: 1.66× 10$^{10}$, Group 2: 1.66×10$^{11}$ GC/ml) of vmGluR6eMCO1 at 7 and 14 days. After anesthetization, blood (-0.2 ml) is drawn from facial vein (using sterile animal lancet) 1 week before intravitreal injection. After vmGluR6eMCO1 injection, blood was drawn (Table 6.1) for analysis. After the completion of the study period, the mouse was euthanized. For collecting the blood from the facial vein of the mice, the hairless freckle on the side of the jaw was located and pricked with a lancet. The pro-inflammatory (IL-6 and IFN-γ) and anti-inflammatory (IL-10) cytokines in plasma were quantified using ELISA kits. FIG. 16 summarizes the results of the ELISA quantification of inflammatory cytokines showing that the intravitreal dose of vmGluR6eMCO1 is within safe limit. FIG. 16A shows quantitative comparison of IL-6 (pro-inflammatory marker) in plasma between group-1 and group-2 before and after 7 and 14 days of vmGluR6eMCO1 injection. FIG. 16B shows the quantitative comparison of IL-10 (anti-inflammatory marker) in plasma between the two groups. FIG. 16C shows the quantitative comparison of IFN-Y (pro-inflammatory marker) in plasma between the two groups before and after 7 and 14 days of vmGluR6eMCO1-injection.

Example 13

After monitoring behavioral restoration of vision by intravitreal injection of vmGluR6eMCO1, the mice were sacrificed and different organs were collected for analyzing the spread of vmGluR6eMCO1 expression in non-targeted tissues samples (eye, heart, liver, muscle, skin, etc). The organs were stored in the 1.8 ml cryovials and stored at −80° C. Each vial was properly labeled with study number, animal identification number, date of extraction, and name of organ. qPCR detection of vector sequences in rd10 mice at different time points post-injection shows very small quantities of vmGluR6eMCO1 DNA in tissues outside of the treated eyes, confirming safety of our molecule and treatment method. Intravitreal administration of vmGluR6eMCO1 in eye led to locally-restricted distribution, minimizing off-target effects. FIG. 17 shows biodistribution of AAV2 packaged Multi-Characteristics Opsin (vmGluR6eMCO1). At a fixed time point after injection (1 week), the measured vector copy number in eye was found to decrease with decrease in injected dose. Further, 4-8 week after injection, very small or non-detectable quantities of vector DNA in the injected eyes was found. The Biodistribution studies showed minimal or non-detectable levels of the vector in non-targeted organs of intravitreally-injected rd10 mice. qPCR detection of vector sequences in rd10 mice at different doses and post-injection period very small or non-detectable quantities of vector DNA in tissues outside of the treated eyes. The biodistribution profile and the kinetics of transgene expression following administration of vmGluR6eMCO1 via the intravitreal administration at multiple time points coincide with the onset of detection, peak vector/transgene levels, and decline/plateau of these levels.

Example 14

To further evaluate the safety, specificity and efficacy of our opsins, immunohistochemistry of vmGluR6eMCO1 injected rd10 retina was conducted. .FIG. 18 shows immunohistochemistry of retinal sections of vmGluR6eMCO1 injected rd10 mice eye. FIG. 18A shows that MCO-mCherry (red) is selectively targeted and expressed in inner nuclear layer (INL) of rd10 mice 8 wks after intravitreal injection of vmGluR6eMCO1. The absence of arrestin (green) suggests a complete loss of photoreceptors. FIG. 18B shows PKCα stain (green) in rod bipolar cells expressing mCherry (red, intrinsic) in rd10 mice 8 wks after intravitreal injection of vmGluR6eMCO1. FIG. 18C shows mGluR6 stain (green) in ON bipolar cells expressing mCherry (red) in rd10 mice 8 wks after intravitreal injection of vmGluR6eMCO1. FIG.

18D shows mCherry (green-immunostained) expression in rd10 retina 8 wks following intravitreal delivery of vmGluR6eMCO1 to rd10 mice. FIG. 18E shows that GFAP (green) in rd10 mice 18 wks after intravitreal injection of vmGluR6eMCO1 as reported in photoreceptor degenerated retina. FIG. 18F shows no CD45 (green) expression suggesting no immune cells in rd10 mice 8 wks after intravitreal injection of vmGluR6eMCO1.

The invention provides a method of improving or restoring vision, comprising administering to a subject any one of the compositions described herein. Compositions of methods of the invented eMCO1 may be delivered and packaged in the plasmid or viral vectors that include: (i) MCO Plasmid, (ii) rAAV-MCO, (iii) pAAV-MCO and (iv) Lenti Virus-MCO. Invention delivery is improvised by use of optimized formulation of AAA together with this invention molecule-MCO (naked plasmid or virus) to transiently permeabilize inner limiting membrane of retina.

Optogenetic Modulation by Multi-Characteristic Opsins for Vision Restoration and Other Applications Thereof

TABLE 01

Amino acid and DNA sequences of Multi-Characteristics Opsin-1 (MCO1)

Amino acid sequence:
MDYGGALSAVGRELLFVTNPVVVNGSVLVPEDQCYCAGWIESRGTNGAQT
ASNVLQWLAAGFSILLLMFYAYQTWKSTCGWEEIYVCAIEMVKVILEFFF
EFKNPSMLYLATGHRVQWLRYAEWLLTCPVISIHLSNLTGLSNDYSRRTM
GLLVSDIGTIVWGATSAMATGYVKVIFFCLGLCYGANTFFHAAKAYIEGY
HTVPKGRCRQVVTGMAWLFFVSWGMFPILFILGPEGFGVLSVYGSTVGHT
IIDLMSKNCWGLLGHYLRVLIHEHILIHGDIRKTTKLNIGGTEIEVETLV
EDESEAGSVNKGTGKMAELISSATRSLFAAGGINPWPNPYHHEDMGCGGM
TPTGECFSTEWWCDPSYGLSDAGYGYCFVEATGGYLVVGVEKKQAWLHSR
GTPGEKIGAQVCQWIAFSIAIALLTFYGFSAWKATCGWEEVYVCCVEVLF
VTLEIPKEFSSPATVYLSTGNHAYCLRYFEWLLSCPVILIRLSNLSGLKN
DYSKRTMGLIVSCVGMIVFGMAAGLATDWLKWLLYIVSCIYGGYMYFQAA
KCYVEANHSVPKGHCRMVVKLMAYAYFASWGSYPILWAVGPEGLLKLSPY
ANSIGHSICEHAKEFWTFLAHHLRIKIHEHILIHGDIRKTTKMEIGGEEV
EVEEFVEEEDEDTV (SEQ ID NO: 1)

DNA sequence:
ATGGATTATGGCGGCGCGCTGAGCGCGGTGGGCCGCGAACTGCTGTTTGT
GACCAACCCGGTGGTGGTGAACGGCAGCGTGCTGGTGCCGGAAGATCAGT
GCTATTGCGCGGGCTGGATTGAAAGCCGCGGCACCAACGGCGCGCAGACC
GCGAGCAACGTGCTGCAGTGGCTGGCGGCCGGGCTTTAGCATTCTGCTGCT
GATGTTTTATGCGTATCAGACCTGGAAAAGCACCTGCGGCTGGGAAGAAA
TTTATGTGTGCGCGATTGAAATGGTGAAAGTGATTCTGGAATTTTTTTTT
GAATTTAAAAACCCGAGCATGCTGTATCTGGCGACCGGCCATCGCGTGCA
GTGGCTGCGCTATGCGGAATGGCTGCTGACCTGCCCGGTGATTAGCATTC
ATCTGAGCAACCTGACCGGCCTGAGCAACGATTATAGCCGCCGCACCATG
GGCCTGCTGGTGAGCGATATTGGCACCATTGTGTGGGGCGCGACCAGCGC
GATGGCGACCGGCTATGTGAAAGTGATTTTTTTTGCCTGGGCCTGTGCT
ATGGCGCGAACACCTTTTTTCATGCGGCGAAAGCGTATATTGAAGGCTAT
CATACCGTGCCGAAAGGCCGCTGCCGCCAGGTGGTGACCGGCATGGCGTG
GCTGTTTTTTGTGAGCTGGGGCATGTTTCCGATTCTGTTTATTCTGGGCC
CGGAAGGCTTTGGCGTGCTGAGCGTGTATGGCAGCACCGTGGGCCATACC
ATTATTGATCTGATGAGCAAAAACTGCTGGGGCCTGCTGGGCCATTATCT
GCGCGTGCTGATTCATGAACATATTCTGATTCATGGCGATATTCGCAAAA
CCACCAAACTGAACATTGGCGGCACCGAAATTGAAGTGGAAACCCTGGTG
GAAGATGAATCGGAAGCGGGCTCGGTGAACAAAGGCACCGGCAAAATGGC
TGAGCTGATCAGCAGCGCCACCAGATCTCTGTTTGCCGCCGGAGGCATCA
ACCCTTGGCCTAACCCCTACCACCACGAGGACATGGGCTGTGGAGGAATG
ACACCTACAGGCGAGTGCTTCAGCACCGAGTGGTGGTGTGACCCTTCTTA
CGGACTGAGCGACGCCGGATACGGATATTGCTTCGTGGAGGCCACAGGCG
GCTACCTGGTCGTGGGAGTGGAGAAGAAGCAGGCTTGGCTGCACAGCAGA
GGCACACCAGGAGAAAGATCGGCGCCCAGGTCTGCCAGTGGATTGCTTT
CAGCATCGCCATCGCCCTGCTGACATTCTACGGCTTCAGCGCCTGGAAGG
CCACTTGCGGTTGGGAGGAGGTCTACGTCTGTTGCGTCGAGGTGCTGTTC
GTGACCCTGGAGATCTTCAAGGAGTTCAGCAGCCCCGCCACAGTGTACCT
GTCTACCGGCAACCACGCCTATTGCCTGCGCTACTTCGAGTGGCTGCTGT
CTTGCCCCGTGATCCTGATCAGACTGAGCAACCTGAGCGGCCTGAAGAAC
GACTACAGCAAGCGGACCATGGGCCTGATCGTGTCTTGCGTGGGAATGAT
CGTGTTCGGCATGGCCGCAGGACTGGCTACCGATTGGCTCAAGTGGCTGC
TGTATATCGTGTCTTGCATCTACGGCGGCTACATGTACTTCCAGGCCGCC
AAGTGCTACGTGGAAGCCAACCACAGCGTGCCTAAAGGCCATTGCCGCAT TABLE 01-continued Amino acid and DNA sequences of Multi-Characteristics Opsin-1 (MCO1)

GGTCGTGAAGCTGATGGCCTACGCTTACTTCGCCTCTTGGGGCAGCTACC
CAATCCTCTGGGCAGTGGGACCAGAAGGACTGCTGAAGCTGAGCCCTTAC
GCCAACAGCATCGGCCACAGCATCTGCGAGATCATCGCCAAGGAGTTTTG
GACCTTCCTGGCCCACCACCTGAGGATCAAGATCCACGAGCACATCCTGA
TCCACGGCGACATCCGGAAGACCACCAAGATGGAGATCGGAGGCGAGGAG
GTGGAAGTGGAAGAGTTCGTGGAGGAGGAGGACGAGGACACAGTG
(SEQ ID NO: 2)

TABLE 02

Amino acid and DNA sequences of Multi-Characteristics Opsin-2 (MCO2). It contains mutation (S 142 L) and deletion of 7 amino acid residues (VNKGTGK) after 308 of MCO1 sequence (TABLE 01).

Amino acid sequence:
MDYGGALSAVGRELLFVTNPVVVNGSVLVPEDQCYCAGWIESRGTNGAQT
ASNVLQWLAAGFSILLLMFYAYQTWKSTCGWEEIYVCAIEMVKVILEFFF
EFKNPSMLYLATGHRVQWLRYAEWLLTCPVILIHLSNLTGLSNDYSRRTM
GLLVSDIGTIVWGATSAMATGYVKVIFFCLGLCYGANTFFHAAKAYIEGY
HTVPKGRCRQVVTGMAWLFFVSWGMFPILFILGPEGFGVLSVYGSTVGHT
IIDLMSKNCWGLLGHYLRVLIHEHILIHGDIRKTTKLNIGGTEIEVETLV
EDESEAGSMAELISSATRSLFAAGGINPWPNPYHHEDMGCGGMTPTGECF
STEWWCDPSYGLSDAGYGYCFVEATGGYLVVGVEKKQAWLHSRGTPGEKI
GAQVCQWIAFSIAIALLTFYGFSAWKATCGWEEVYVCCVEVLFVTLEIFK
EFSSPATVYLSTGNHAYCLRYFEWLLSCPVILIRLSNLSGLKNDYSKRTM
GLIVSCVGMIVFGMAAGLATDWLKWLLYIVSCIYGGYMYFQAAKCYVEAN
HSVPKGHCRMVVKLMAYAYFASWGSYPILWAVGPEGLLKLSPYANSIGHS
ICEITAKEFWTFLAHHLRIKIHEHILIHGDIRKTTKMEIGGEEVEVEEFV
EEEDEDTV (SEQ ID NO: 3)

Nucleotide sequence:
ATGGACTATGGCGGAGCATTGAGTGCAGTTGGGCGAGAATTGCTGTTCGT
GACGAATCCCGTTGTTGTAAACGGAAGTGTACTGGTGCCAGAAGACCAAT
GTTATTGCGCGGGCTGGATAGAGTCGCGCGGAACGAATGGAGCACAGACA
GCGTCCAACGTACTGCAATGGCTCGCCGCTGGTTTCTCTATCCTGTTGTT
GATGTTCTACGCATATCAAACGTGGAAAAGCACCTGCGGGTGGGAGGAAA
TATATGTGTGTGCCATCGAGATGGTAAAAGTAATTTTAGAGTTTTTTTT
GAATTCAAGAACCCCTCAATGTTGTACCTTGCTACGGGGCATAGAGTTCA
ATGGCTTCGGTATGCGGAATGGCTCTTGACATGTCCAGTAATACTAATTC
ATCTTAGTAACTTAACGGGACTCTCTAACGACTATTCACGGCGTACCATG
GGACTACTGGTGTCAGACATTGGGACGATAGTATGGGGAGCGACGAGCGC
AATGGCTACAGGCTACGTAAAGGTTATCTTTTTCTGCCTCGGGCTTTGTT
ACGGCGGAATACCTTCTTTCATGCCGCAAAGGCCTACATAGAGGGTTAC
CATACCGTACCGAAAGGGCGGTGCCGGCAAGTCGTCACAGGAATGGCTTG
GCTCTTCTTTGTGAGTTGGGGAATGTTCCCTATCCTATTTATCTTAGGGC
CTGAGGGTTTCGGCGTGCTTAGTGTTTACGGCAGTACGGTCGGTCACACG
ATCATCGACCTGATGTCAAAGAATTGCTGGGGCTTGCTTGGTCATTATTT
GCGTGTGTTAATCCACGAACATATTCTGATTCATGGTGACATCCGAAAAA
CTACCAAACTCAATATTGGCGGCACAGAGATAGAGGTTGAAACGTTGGTC
GAGGACGAGTCTGAAGCGGGGTCAATGGCGGAACTAATTTCATCTGCAAC
ACGGTCGCTATTTGCTGCCGGGGGGATAAATCCCTGGCCCAACCCGTATC
ACCACGAAGATATGGGATGCGGAGGGATGACTCCCACAGGAGAGTGTTTT
TCGACCGAATGGTGGTGTGACCCCTCGTACGGGTTATCAGATGCAGGCTA
TGGTTATTGTTTCGTGGAGGCCACGGGTGGTTATTTAGTCGTAGGGGTAG
AGAAGAAACAGGCATGGCTTCATTCCCGGGGAAACCCCGGGAGAAAATT
GGAGCTCAGGTATGCCAGTGGATAGCGTTTTCTATCGCGATAGCTCTCCT
GACTTTTTATGGATTTTCGGCTTGGAAGGCCACGTGCGGATGGGAAGAGG
TATACGTATGTTGCGTCGAAGTGCTTTTCGTAACTCTGGAAATATTTAAA
GAATTCTCAAGTCCGGCCACAGTTTATTTGAGCACTGGCAACCACGCCTA
TTGTTTGCGGTATTTTGAGTGGCTATTATCTTGCCCTGTTATTCTTATAC
GGTTATCAAACCTATCGGGTCTGAAGAATGATTATTCAAGAGAACCATG
GGCCTAATTGTCAGTTGCGTCGGGATGATCGTGTTCGGGATGGCCGCGGG
TCTTGCAACGGACTGGCTTAAGTGGCTATTATACATCGTCAGCTGCATTT
ACGGTGGTTACATGTACTTTCAAGCGGCTAAGTGCTATGTGGAGGCGAAC
CATTCAGTCCCGAAAGGCCACTGTCGCATGGTGGTTAAGTTAATGGCGTA
TGCGTACTTCGCTTCGTGGGGTTCATATCCAATCCTGTGGGCGGTCGGAC
CTGAAGGTCTCCTGAAACTGAGCCCCTATGCGAACTCCATAGGACATTCC
ATCTGTGAGATCATCGCCAAGGAATTCTGGACCTTCTTAGCTCACCATTT

TABLE 02-continued

Amino acid and DNA sequences of Multi-Characteristics Opsin-2 (MCO2). It contains mutation (S 142 L) and deletion of 7 amino acid residues (VNKGTGK) after 308 of MCO1 sequence (TABLE 01).

GCGGATTAAGATCCATGAACACATTCTCATTCACGGTGATATTAGGAAAA
CTACCAAGATGGAGATAGGTGGAGAAGAGGTGGAGGTAGAAGAGTTTGTA
GAAGAGGAGGACGAGGACACTGTAGTATCAAAGGGGGAAGAAGACAAT
(SEQ ID NO: 4)

TABLE 03

Amino acid and DNA sequences of Multi-Characteristics Opsin-1T (MCO1T). It contains additional trans-membrane sequence (TPARWVWISLYYAAFYVVMTGLFALCIYVLMQTI) after 315 amino acid residues of MCO1 (TABLE 01).

Amino acid sequence:
MDYGGALSAVGRELLFVTNPVVVNGSVLVPEDQCYCAGWIESRGTNGAQT
ASNVLQWLAAGFSILLLMFYAYQTWKSTCGWEEIYVCAIEMVKVILEFFF
EFKNPSMLYLATGHRVQWLRYAEWLLTCPVISIHLSNLTGLSNDYSRRTM
GLLVSDIGTIVWGATSAMATGYVKVIFFCLGLCYGANTFFHAAKAYIEGY
HTVPKGRCRQVVTGMAWLFFVSWGMFPILFILGPEGFGVLSVYGSTVGHT
IIDLMSKNCWGLLGHYLRVLIHEHILIHGDIRKTTKLNIGGTEIEVETLV
EDESEAGSVNKGTGKTPARWVWISLYYAAFYVVMTGLFALCIYVLMQTIM
AELISSATRSLFAAGGINPWPNPYHHEDMGCGGMTPTGECFSTEWWCDPS
YGLSDAGYGYCFVEATGGYLVVGVEKKQAWLHSRGTPGEKIGAQVCQWIA
FSIAIALLTFYGFSAWKATCGWEEVYVCCVEVLFVTLEIFKEFSSPATVY
LSTGNHAYCLRYFEWLLSCPVILIRLSNLSGLKNDYSKRTMGLIVSCVGM
IVFGMAAGLATDWLKWLLYIVSCIYGGYMYFQAAKCYVEANHSVPKGHCR
MVVKLMAYAYFASWGSYPILWAVGPEGLLKLSPYANSIGHSICEIIAKEF
WTFLAHHLRIKIHEHILIHGDIRKTTKMEIGGEEVEVEEFVEEEDEDTV
(SEQ ID NO: 5)

Nucleotide sequence
ATGGATTACGGAGGAGCACTGAGCGCTGTTGGCCGCGAGTTGCTATTTGT
GACCAACCCCGTCGTGGTCAATGGCAGCGTCCTTGTGCCTGAGGATCAAT
GTTATTGCGCTGGGTGGATTGAATCCCGAGGTACAAATGGTGCCCAGACG
GCAAGCAACGTTTTGCAATGGCTAGCAGCTGGGTTTTCAATTCTACTTTT
AATGTTTTACGCTTATCAAACCTGGAAGAGTACATGTGGCTGGGAGGAAA
TTTATGCTCGCGTATTGAAATGGTTAAAGTAATTTTGGAATTTTTTTTT
GAATTTAAGAATCCATCAATGTTGTATCTTGCCACAGGTCACAGGGTCCA
ATGGCTCCGATACGCGAATGGCTTCTAACTTGCCCTGTTATTCCATTC
ACCTAAGCAATCTGACTGGCCTTTCGAATGACTATAGCAGACGCACCATG
GGACTGTTAGTTAGTGACATAGGGACTATAGTTTGGGGTGCCACTAGCGC
CATGGCGACCGGTTATGTTAAAGTAATTTTTTTCTGCCTTGGGTTGTGTT
ATGGCGCTAACACTTTTTTCCACGCTGCTAAAGCATATATAGAAGGGTAC
CATACGGTGCCCAAAGGAAGATGTCGCCAAGTAGTTACAGGGATGGCGTG
GCTGTTCTTTGTGAGCTGGGGGATGTTCCCTATACTGTTTATCCTTGGTC
CAGAGGGTTTTGGAGTCCTAAGCGTGTACGGCAGTACTGTTGGGCATACT
ATAATAGATTTGATGAGCAAAAACTGCTGGGGGCTTCTCGGGCATTATTT
ACGAGTTCTTATTCACGAACATATTTTAATTCATGGGGATATCAGAAAAA
CAACGAAACTAAATATAGGAGGCACGGAAATAGAGGTTGAAACGCTCGTC
GAAGACGAATCAGAAGCCGGCTCCGTGAATAAGGGAACTGGTAAAACTCC
TGCTCGCTGGGTATGGATATCGCTTTACTACGCAGCATTTTACGTAGTTA
TGACTGGGCTTTTTGCTTTGTGCATATACGTGCTAATGCAGACGATTATG
GCTGAGCTAATTTCATCTGCAACTAGATCCCTTTTCGCGGCAGGAGGGAT
CAACCCCTGGCCCAATCCATATCATCATGAAGATATGGGCTGTGGCATCA
TGACCCCAACTGGTGAGTGCTTTTCTACCGAAATGGTGGTGTGATCCGAGT
TACGGTCTGTCAGATGCTGGGTATGGTTATTGCTTTGTGAAGCCACGGG
GGGATACCTTGTCGTCGGAGTAGAGAAAAAACAGGCCTGGCTCCATTCCC
GGGGGACCCCAGGAGAGAAGATAGGGGCCCAAGTTTGCCAGTGGATCGCA
TTTAGTATTGCGATCGCATTACTGACATTCTATGGTTTCTCAGCGTGGAA
GGCAACCTGCGGCTGGGAGGAGGTTTACGTATGCTGTGTTGAGGTACTGT
TCGTAACCCTTGAGATTTTCAAAGAGTTTTCTTCCGGCGACGGTCTAT
CTCAGTACCGGTAACCATGCATATTGTTTACGTTATTTCGAATGGTTGCT
TTCTTGCCCAGTGATTTTGATACGCTTGAGTAATTTATCTGGCCTAAAGA
ACGACTATAGCAAGCGAACCATGGGACTTATTGTATCTTGTGTTGGCATG
ATAGTTTTTGGTATGGCAGCCGGGCTCGCCACTGACTGGCTGAAGTGGTT
GCTCTATATAGTGAGCTGTATTTATGGTGGCTACATGTACTTTCAGGCGG
CCAAGTGTTACGTTGAAGCAAACCATTCGGTACCTAAAGGACATTGCCGT
ATGGTAGTTAAGCTGATGGCGTATGCGTACTTCGCGAGCTGGGCAGCTA
CCCCATTCTGTGGGCGGTGGGACCAGAGGGGTTACTTAAGTTGTCGCCCT
ATGCTAATTCAATAGGCCATAGCATCTGTGAGATTATCGCGAAGGAATTT
TGGACTTTCCTAGCACATCACCTTCGAATTAAAATACACGAACACATACT

TABLE 03-continued

Amino acid and DNA sequences of Multi-Characteristics Opsin-1T (MCO1T). It contains additional trans-membrane sequence (TPARWVWISLYYAAFYVVMTGLFALCIYVLMQTI) after 315 amino acid residues of MCO1 (TABLE 01).

CATTCACGGGGACATACGCAAGACAACCAAGATGGAAATCGGAGGTGAGG
AAGTGGAAGTAGAGGAGTTTGTAGAGGAGGAAGATGAGGACACGGTT
(SEQ ID NO: 6)

TABLE 04

Amino acid and DNA sequences of Multi-Characteristics Opsin-2T (MCO2T). It contains additional trans-membrane sequence (TPARWVWISLYYAAFYVVMTGLFALCIYVLMQTI) after 308 amino acid residues of MCO2 (TABLE 02).

Amino acid sequence:
MDYGGALSAVGRELLFVTNPVVVNGSVLVPEDQCYCAGWIESRGTNGAQT
ASNVLQWLAAGFSILLLMFYAYQTWKSTCGWEEIYVCAIEMVKVILEFFF
EFKNPSMLYLATGHRVQWLRYAEWLLTCPVIHLSNLTGLSNDYSRRTM
GLLVSDIGTIVWGATSAMATGYVKVIFFCLGLCYGANTFFHAAKAYIEGY
HTVPKGRCRQVVTGMAWLFFVSWGMFPILFILGPEGFGVLSVYGSTVGHT
IIDLMSKNCWGLLGHYLRVLIHEHILIHGDIRKTTKLNIGGTEIEVETLV
EDESEAGSPARWVWISLYYAAFYVVMTGLFALCIYVLMQTIMAELISSAT
RSLFAAGGINPWPNPYHHEDMGCGGMTPTGECFSTEWWCDPSYGLSDAGY
GYCFVEATGGYLVVGVEKKQAWLHSRGTPGEKIGAQVCQWIAFSIAIALL
TFYGFSAWKATCGWEEVYVCCVEVLFVTLEIFKEFSSPATVYLSTGNHAY
CLRYFEWLLSCPVILIRLSNLSGLKNDYSKRTMGLIVSCVGMIVFGMAAG
LATDWLKWLLYIVSCIYGGYMYFQAAKCYVEANHSVPKGHCRMVVKLMAY
AYFASWGSYPILWAVGPEGLLKLSPYANSIGHSICEIIAKEFWTFLAHHL
RIKIHEHILIHGDIRKTTKMEIGGEEVEVEEFVEEEDEDTV (SEQ ID
NO: 7)

Nucleotide Sequence:
ATGGACTATGGAGGAGCACTGTCAGCCGTTGGGAGAGAGTTGTTGTTTGT
TACCAATCCTGTAGTAGTCAATGGCAGTGTGCTTGTACCAGAGGATCAAT
GCTACTGTGCCGGGTGGATAGAGTCCCGGGAACCAACGGGGCACAACT
GCGAGTAACGTTCTGCAATGGCTAGCAGCAGGCTTTAGCATACTGCTACT
AATGTTCTATGCTTACCAAACATGGAAGTCGACTTGCGGGTGGGAGGAGA
TATACGTCTGCGCAATTGAAATGGTCAAGGTTATTCTCGAGTTCTTCTTC
GAATTCAAAAACCCATCAATGTTATACTTAGCGACAGGACATCGAGTCCA
GTGGTTACGTTACGCCGAGTGGCTCCTGAGTGCCCGGTAATTTTAATCC
ACCTCTCTAATTTGACCGGACTTTCCAATGATTACAGTCGAAGAACTATG
GGGCTATTAGTCTCTGACATCGGGACTATTGTCGGGGTGCGACTAGCGC
TATGGCTACCGGGTATGTAAAAGTCATCTTCTTCTGTTTAGGACTGTGCT
ACGGCGCGAACATACATTCTTTCACGCTGCGAAAGCTTATATGAAGGCTAT
CACACGTGTACCTAAAGGTCGGTGTAGGCAGGTCGTCACCGGTATGGCGTG
GTTGTTCTTCGTATCATGGGGAATGTTTCCAATCTTGTTTATACTAGGTC
CCGAAGGATTTGGAGTGTTGTCCGTTTACGGATCAACAGTAGGCCACACT
ATTATCGATTTGATGTCTAAAAACTGCTGGGGGCTTTAGGTCACTATCT
AAGGGTGCTCATTCATGACACATATTAATCCATGGCGATATCAGAAAGA
CGACGAAACTGAATATTGGAGGCACTGAGATCGAAGTAGAGACGCTTGTC
GAAGACGAATCCGAAGCTGGTAGCCCCGCACGCTGGGTCTGGATATCTTT
GTACTATGCCGCCTTCTATGTTGTTATGACAGGACTCTTTGCTTTATGCA
TCTATGTCCTAATGCAAACTATTATGGCTGAACTTATATCATCGGCAACA
AGGAGTTTATTTGCGGCTGGGGGAATAAATCCGTGGCCCAACCCCTACCA
TCATGAAGATATGGGTTGCGGCGGCATGACCCCGACAGGGGAATGCTTCT
CGACGGAGTGGTGGTGTGATCCTTCTTATGGACGTAGTGATGCTGGGTAT
GGCTATTGTTCGTAGAGGCTACGGGGGGTACTTGGTCGTTGGAGTCGA
GAAAAAACAGGCATGGTTACATAGAGGGGACTCCTGGAGAGAAAATAG
GTGCCCAGGTTTGTCAATGGATTGCTTTCTCGATTGCAATAGCTCTGTTA
ACGTTCTATGGCTTCTCCGCGTGGAAGGCTACTTGTGGCTGGGAAGAGGT
ATATGTTTGTGTGTTGAAGTTCTATTTGTAACACTTGAGATATTTAAAG
AATTTTCTTCACCCGCAACGGTCTACTTAAGTACAGGCAATCATGCTAC
TGTCTAAGATACTTCGAATGGCTCTTATCATGTCCGGTGATCTTAATTCG
ACTCTCGAACCTCTCTGGACTCAAGAATGACTATAGTAAGGACTATGG
GACTCATTGTCGTCGGTGTTGGTATGATTGTGTTGGTATGGCGGCAGGG
CTGGCTACGGATGGCTAAAGTGGCTGCTATATATAGTGAGCTGTATCTA
TGGCGGTTACATGTATTTCCAGGCGGCCAAGTGTTATGTCGAGGCGAATC
ACTCGGTCCCCAAAGGTCATTGTCGGATGGTGGTCAAGCTTATGGCGTAC
GCATATTTCGCCAGCTGGGGATCGTACCCGATACTTTGGGCCGTTGGCCC

TABLE 04-continued

Amino acid and DNA sequences of Multi-Characteristics Opsin-2T (MCO2T). It contains additional trans-membrane sequence (TPARWVWISLYYAAFYVVMTGLFALCIYVLMQTI) after 308 amino acid residues of MCO2 (TABLE 02).

```
AGAAGGGCTACTAAAGTTGAGCCCGTACGCCAATTCAATTGGGCATAGTA
TCTGTGAGATAATTGCTAAGGAGTTTTGGACGTTTTTAGCTCACCATCTG
AGAATTAAGATTCATGAGCACATCTTAATTCACGGGGATATCCGCAAGAC
TACCAAGATGGAGATAGGTGGGGAGGAGGTGGAGGTAGAAGAGTTTGTAG
AAGAAGAGGATGAAGATACTGTA (SEQ ID NO: 8)
```

TABLE 05

DNA sequences of promoter (mGluR6) used upstream of MCO-sequences for targeting specific cells as an example.

```
CAGGGNNGATTGATTATTGACTAGTGATCTCCAGATGGCTAAACTTTTAA
ATCATGAATGAAGTAGATATTACCAAATTGCTTTTTCAGCATCCATTTAG
ATAATCATGTTTTTTGCCTTTAATCTGTTAATGTAGTGAATTACAGAAAT
ACATTTCCTAAATCATTACATCCCCCAAATCGTTAATCTGCTAAAGTACA
(SEQ ID NO: 9)
```

TABLE 06

DNA sequences of reporter-stabilizer (mCherry) used downstream of MCO-sequences for confirming expression in specific cells as an example.

```
ATGGCCATCATCAAGGAGTTCATGCGCTTCAAGGTGCACATGGAGGGCTC
CGGAACGGCCCGAGTTCGAGATCGAGGGCGAGGGCGAGGGCCGCCCCTAC
GAGGGCACCCAGACCGCCAAGCTGAAGGTGACCAAGGGTGGCCCCCTGCC
CTTCGCCTGGGACATCCTGTCCCCTCAGTTCATGTACGGCTCCAAGGCCT
ACGTGAAGCACCCCGCCGACATCCCCGACTACTTGAAGCTGTCCTTCCCC
GAGGGCTTCAAGTGGGAGCGCGTGATGAACTTCGAGGACGGCGGCGTGGT
GACCGTGACCCAGGACTCCTCCCTGCAGGACGGCGAGTTCATCTACAAGG
TGAAGCTGCGCGGCACCAACTTCCCCTCCGACGGCCCCGTAATGCAGAAG
AAGACCATGGGCTGGGAGGCCTCCTCCGAGCGGATGTACCCCGAGGACGG
CGCCCTGAAGGGCGAGATCAAGCAGAGGCTGAAGCTGAAGGACGGCGGCT
ACTACGACGCTGAGGTCAAGACCACCTACAAGGCCAAGAAGCCCGTGCAGC
TGCCCGGCGCCTACAACGTCAACATCAAGTTGGACATCACCTCCCACAAC
GAGGACTACACCATCGTGGAACAGTACGAACGCGCCGAGGGCCGCCACTC
CACCGGCGGCATGGACGAGCTGTACAAG TAA (SEQ ID NO: 10)
```

TABLE 07

Amino acid and DNA sequences of Enhanced Multi-Characteristics Opsin-1 (eMCO1). It contains MCO1 sequence (Table 01) and biomarker-stabilizer sequence (Table 06).

Amino acid sequence:
```
MDYGGALSAVGRELLFVTNPVVVNGSVLVPEDQCYCAGWIESRGTNGAQT
ASNVLQWLAAGFSILLLMFYAYQTWKSTCGWEEIYVCAIEMVKILEFFF
EFKNPSMLYLATGHRVQWLRYAEWLLTCPVICIHSNLTGLSNDYSRRTMG
LLVSDIGTIVWGATSAMATGYVKVIFFCLGLCYGANTFFHAAKAYIEGYH
TVPKGRCRQVVTGMAWLFFVSWGMFPILFILGPEGFGVLSVYGSTVGHTI
IDLMSKNCWGLLGHYLRVLIHEHILIHGDIRKTTKLNIGGTEIEVETLVE
DEAEAGAVNKGTGKMAELISSATRSLFAAGGINPWPNPYHHEDMGCGGMT
PTGECFSTEWWCDPSYGLSDAGYGYCFVEATGGYLVVGVEKKQAWLHSRG
TPGEKIGAQVCQWIAFSIAIALLTFYGFSAWKATCGWEEVYVCCVEVLFV
TLEIFKEFSSPATVYLSTGNHAYCLRYFEWLLSCPVILIRLSNLSGLKND
YSKRTMGLIVSCVGMIVFGMAAGLATDWLKWLLYIVSCIYGGYMYFQAAK
CYVEANHSVPKGHCRMVVKLMAYAYFASWGSYPILWAVGPEGLLKLSPYA
NSIGHSICDIIAKEFWTFLAHHLRIKIHEHILIHGDIRKTTKMEIGGEEV
EVEEFVEEEDEDTVVSKGEEDNMAIIKEFMRFKVHMEGSVNGHEFEIEGE
GEGRPYEGTQTAKLKVTKGGPLPFAWDILSPQFMYGSKAYVKHPADIPDY
LKLSFPEGFKWERVMNFEDGGVVTVTQDSSLQDGEFIYKVKLRGTNFPSD
GPVMQKKTMGWEASSERMYPEDGALKGEIKQRLKLKDGGHYDAEVKTTYK
AKKPVQLPGAYNVNIKLDITSHNEDYTIVEQYERAEGRHSTGGMDELYK
(SEQ ID NO: 11)
```

Nucleotide sequence:
```
ATGGATTATGGCGGCGCGCTGAGCGCGGTGGGCCGCGAACTGCTGTTTGT
GACCAACCCGGTGGTGGTGAACGGCAGCGTGCTGGTGCCGGAAGATCAGT
GCTATTGCGCGGGCTGGATTGAAAGCCGCGGCACCAACGGCGCGCAGACC
GCGAGCAACGTGCTGCAGTGGCTGGCGGCGGGCTTTAGCATTCTGCTGCT
GATGTTTTATGCGTATCAGACCTGGAAAAGCACCTGCGGCTGGGAAGAAA
TTTATGTGTGCGCGATTGAAATGGTGAAAGTGATTCTGGAATTTTTTTTT
GAATTTAAAAACCCGAGCATGCTGTATCTGGCGACCGGCCATCGCGTGCA
GTGGCTGCGCTATGCGGAATGGCTGCTGACCTGCCCGGTGATTTGCATTC
ATCTGAGCAACCTGACCGGCCTGAGCAACGATTATAGCCGCCGCACCATG
GGCCTGCTGGTGAGCGATATTGGCACCATTGTGTGGGGCGCGACCAGCGC
GATGGCGACCGGCTATGTGAAAGTGATTTTTTTTTGCCTGGGCCTGTGCT
ATGGCGCGAACACCTTTTTTCATGCGGCGAAAGCGTATATTGAAGGCTAT
CATACCGTGCCGAAAGGCCGCTGCCGCCAGGTGGTGACCGGCATGGCGTG
GCTGTTTTTTGTGAGCTGGGGCATGTTTCCGATTCTGTTTATTCTGGGCC
CGGAAGGCTTTGGCGTGCTGAGCGTGTATGGCAGCACCGTGGGCCATACC
ATTATTGATCTGATGAGCAAAAACTGCTGGGGCCTGCTGGGCCATTATCT
GCGCGTGCTGATTCATGAACATATTCTGATTCATGGCGATATTCGCAAAA
CCACCAAACTGAACATTGGCGGCACCGAAATTGAAGTGGAAACCCTGGTG
GAAGATGAAGCGGAAGCGGGCGCGGTGAACAAAGGCACCGGCAAAATGGC
TGAGCTGATCAGCAGCGCCACCAGATCTCTGTTTGCCGCCGGAGGCATCA
ACCCTTGGCCTAACCCCTACCACCACGAGGACATGGGCTGTGGAGGAATG
ACACCTACAGGCGAGTGCTTCAGCACCGAGTGGTGGTGTGACCCTTCTTA
CGGACTGAGCGACGCGGATACGGATATTGCTTCGTGGAGGCCACAGGCG
GCTACCTGGTCGTGGGAGTGGAGAAGAAGCAGGCTTGGCTGCACAGCAGA
GGCACACCAGGAGAAAAGATCGGCGCCCAGGTCTGCCAGTGGATTGCTTT
CAGCATCGCCATCGCCCTGCTGACATTCTACGGCTTCAGCGCCTGGAAGG
CCACTTGCGGTTGGGAGGAGGTCTACGTCTGTTGCGTCGAGGTGCTGTTC
GTGACCCTGGAGATCTTCAAGGAGTTCAGCAGCCCCGCCACAGTGTACCT
GTCTACCGGCAACCACGCCTATTGCCTGCGCTACTTCGAGTGGCTGCTGT
CTTGCCCCGTGATCCTGATCAGACTGAGCAACCTGAGCGGCCTGAAGAAC
GACTACAGCAAGCGGACCATGGGCCTGATCGTGTCTTGCGTGGGAATGAT
CGTGTTCGGCATGGCCGCAGGACTGGCTACCGATTGGCTCAAGTGGCTGC
TGTATATCGTGTCTTGCATCTACGGCGGCTACATGTACTTCCAGGCCGCC
AAGTGCTACGTGGAAGCCAACCACAGCGTGCCTAAAGGCCATTGCCGCAT
GGTCGTGAAGCTGATGGCCTACGCTTACTTCGCCTCTTGGGGCAGCTACC
CAATCCTCTGGGCAGTGGGACCAGAAGGACTGCTGAAGCTGAGCCCTTAC
GCCAACAGCATCGGCCACAGCATCTGCGACATCATCGCCAAGGAGTTTTG
GACCTTCCTGGCCCACCACCTGAGGATCAAGATCCACGAGCACATCCTGA
TCCACGGCGACATCCGGAAGACCACCAAGATGGAGATCGGAGGCGAGGAG
GTGGAAGTGGAAGAGTTCGTGGAGGAGGAGGACGAGGACACAGTGGTGAG
CAAGGGCGAGGAGGATAACATGGCCATCATCAAGGAGTTCATGCGCTTCA
AGGTGCACATGGAGGGCTCCGTGAACGGCCACGAGTTCGAGATCGAGGGC
GAGGGCGAGGGCCGCCCCTACGAGGGCACCCAGACCGCCAAGCTGAAGGT
GACCAAGGGTGGCCCCCTGCCCTTCGCCTGGGACATCCTGTCCCCTCAGT
TCATGTACGGCTCCAAGGCCTACGTGAAGCACCCCGCCGACATCCCCGAC
TACTTGAAGCTGTCCTTCCCCGAGGGCTTCAAGTGGGAGCGCGTGATGAA
CTTCGAGGACGGCGGCGTGGTGACCGTGACCCAGGACTCCTCCCTGCAGG
ACGGCGAGTTCATCTACAAGGTGAAGCTGCGCGGCACCAACTTCCCCTCC
GACGGCCCCGTAATGCAGAAGAAGACCATGGGCTGGGAGGCCTCCTCCGA
GCGGATGTACCCCGAGGACGGCGCCCTGAAGGGCGAGATCAAGCAGAGGC
TGAAGCTGAAGGACGGCGGCCACTACGACGCTGAGGTCAAGACCACCTAC
AAGGCCAAGAAGCCCGTGCAGCTGCCCGGCGCCTACAACGTCAACATCAA
GTTGGACATCACCTCCCACAACGAGGACTACACCATCGTGGAACAGTACG
AACGCGCCGAGGGCCGCCACTCCACCGGCGGCATGGACGAGCTGTACAAG
TAA (SEQ ID NO: 12)
```

TABLE 08

Comparison of stability of the MCO1 and eMCO1 based on secondary structure and folding using theoretical modeling by RaptorX.

| Protein | Alpha helix (%) | Beta sheet (%) | Random Coil (%) | Prediction of disordered region |
|---|---|---|---|---|
| MCO1 | 58 | 7 | 33 | 29(4%) positions predicted as disordered |
| eMCO1 | 46 | 17 | 36 | 15 (1%) position predicted as disordered |

The terms "a" and "an" are defined as one or more unless this disclosure explicitly requires otherwise. The term "substantially" is defined as largely but not necessarily wholly what is specified (and includes what is specified; e.g., substantially 90 degrees includes 90 degrees and substantially parallel includes parallel), as understood by a person of ordinary skill in the art. In any disclosed embodiment, the terms "substantially," "approximately," and "about" may be substituted with "within [a percentage] of" what is specified, where the percentage includes 0.1, 1, 5, and 10 percent.

Further, a molecule or method that is configured in a certain way is configured in at least that way, but it can also be configured in other ways than those specifically described.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, an apparatus that "comprises," "has," "includes" or "contains" one or more elements possesses those one or more elements, but is not limited to possessing only those elements. Likewise, a method that "comprises," "has," "includes" or "contains" one or more steps possesses those one or more steps, but is not limited to possessing only those one or more steps.

Any embodiment of any of the apparatuses, systems, and methods can consist of or consist essentially of—rather than comprise/include/contain/have—any of the described steps, elements, and/or features.

Thus, in any of the claims, the term "consisting of" or "consisting essentially of" can be substituted for any of the open-ended linking verbs recited above, in order to change the scope of a given claim from what it would otherwise be using the open-ended linking verb.

The feature or features of one embodiment may be applied to other embodiments, even though not described or illustrated, unless expressly prohibited by this disclosure or the nature of the embodiments. Below, the presently disclosed invention will be further described by way of examples, which are provided for illustrative purposes only and accordingly are not to be construed as limiting the scope of the invention.

Some references, which may include publications, patents, and patent applications, are cited and discussed in the description of this invention. The citation and/or discussion of such references is provided merely to clarify the description of the present invention and is not an admission that any such reference is "prior art" to the invention described herein. All references cited and discussed in this specification are incorporated herein by reference in their entireties and to the same extent as if each reference were individually incorporated by reference.

The specification and examples herein provide a complete description of the structure and use of illustrative embodiments. Although certain embodiments have been described with a certain degree of particularity, or with reference to one or more individual embodiments, those skilled in the art could make numerous alterations to the disclosed embodiments without departing from the scope of this invention. As such, the various illustrative embodiments of the devices are not intended to be limited to the particular forms disclosed. Rather, they include all modifications and alternatives falling within the scope of the claims, and embodiments other than the one shown may include some or all of the features of the depicted embodiment. For example, components may be omitted or combined as a unitary structure, and/or connections may be substituted. Further, where appropriate, aspects of any of the examples described above may be combined with aspects of any of the other examples described to form further examples having comparable or different properties and addressing the same or different problems. Similarly, it will be understood that the benefits and advantages described above may relate to one embodiment or may relate to several embodiments.

Furthermore, the claims are not intended to include, and should not be interpreted to include, means-plus- or step-plus-function limitations, unless such a limitation is explicitly recited in a given claim using the phrase(s) "means for" or "step for," respectively.

To the extent that any specific disclosure in the references or other literature may be considered to anticipate any generic aspect of the present invention, the disclosure of the present invention should be understood to include a proviso or provisos that exclude of disclaim any such species that were previously disclosed. The aspects of the present invention, which are not anticipated by the disclosure of such literature, are also nonobvious from the disclosure of these publications, due at least in part to the unexpectedly superior results disclosed herein.

For each of the claims, each dependent claim can depend both from the independent claim and from each of the prior dependent claims for each and every claim so long as the prior claim provides a proper antecedent basis for a claim term or element.

REFERENCES

The following references, to the extent that they provide exemplary procedural or other details supplementary to those set forth above, are specifically incorporated by reference.

1. Pan Z-H, Dizhoor A M. Restoration of visual responses by in vivo delivery of rhodopsin nucleic acids. Google Patents; 2013.
2. Barrett J M, Berlinguer-Palmini R, Degenaar P. Optogenetic approaches to retinal prosthesis. Visual Neurosci. 2014; 31(4-5):345-54.
3. Dichtl A, Jonas J B, Naumann G O. Retinal nerve fiber layer thickness in human eyes. Graefe's archive for clinical and experimental ophthalmology. 1999; 237(6):474-9.
4. Busskamp V, Picaud S, Sahel J A, Roska B. Optogenetic therapy for retinitis pigmentosa. Gene Ther. 2012; 19(2): 169-75.
5. Nagel G, Szellas T, Huhn W, Kateriya S, Adeishvili N, Berthold P, Ollig D, Hegemann P, Bamberg E. Channelrhodopsin-2, a directly light-gated cation-selective membrane channel Proc Nat Acad Sci. 2003; 100(24): 13940-5.
6. Boyden E S, Zhang F, Bamberg E, Nagel G, Deisseroth K. Millisecond-timescale, genetically targeted optical control of neural activity. Nat Neurosci. 2005; 8(9):1263-8.
7. Miller G. Shining New Light on Neural Circuits. Science. 2006; 314(5806):1674-6.
8. Zhang F, Aravanis A M, Adamantidis A, de Lecea L, Deisseroth K. Circuit-breakers: optical technologies for probing neural signals and systems. Nat Rev Neurosci. 2007; 8(8):577-81.
9. Zhang F, Wang L P, Boyden E S, Deisseroth K. Channelrhodopsin-2 and optical control of excitable cells. Nat Methods. 2006; 3(10):785-92.
10. Mohanty S K, Reinscheid R K, Liu X, Okamura N, Krasieva T B, Berns M W. In-Depth Activation of Channelrhodopsin 2-Sensitized Excitable Cells with High Spatial Resolution Using Two-Photon Excitation with a Near-Infrared Laser Microbeam. Biophys J. 2008; 95(8):3916-26.
11. Zhang F, Aravanis A M, Adamantidis A, de Lecea L, Deisseroth K. Circuit-breakers: optical technologies for probing neural signals and systems. Nat Rev Neurosci. 2007; 8(8):577-81.
12. Nagel G, Brauner M, Liewald J F, Adeishvili N, Bamberg E, Gottschalk A. Light activation of channelrhodopsin-2 in excitable cells of *Caenorhabditis elegans* triggers rapid behavioral responses. Curr Biol. 2005; 15(24):2279-84.
13. Schroll C, Riemensperger T, Bucher D, Ehmer J, Voller T, Erbguth K, Gerber B, Hendel T, Nagel G, Buchner E, Fiala A. Light-induced activation of distinct modulatory neurons triggers appetitive or aversive learning in *Drosophila* larvae. Current Biology. 2006; 16(17):1741-7.
14. Cao H, Gu L, Mohanty S K, Chiao J C. An Integrated mu LED Optrode for Optogenetic Stimulation and Electrical Recording. IEEE Trans Bio-Med Eng. 2013; 60(1):225-9.
15. Dhakal K, Gu L, Shivalingaiah S, Dennis T, Bobzean S, Perrotti L, Mohanty S. Non-scanning fiber-optic near-infrared beam led to two-photon optogenetic stimulation in vivo. Plos One. 2014; 9 (11), e111488.
16. Hartong D T, Berson E L, Dryja T P. Retinitis pigmentosa. Lancet. 2006; 368(9549):1795-809.
17. Sugawara T, Hagiwara A, Hiramatsu A, Ogata K, Mitamura Y, Yamamoto S. Relationship between peripheral visual field loss and vision-related quality of life in patients with retinitis pigmentosa. Eye (Lond). 2010; 24(4):535-9.
18. Daiger S P, Bowne S J, Sullivan L S. Perspective on genes and mutations causing retinitis pigmentosa. Arch Ophthalmol. 2007; 125 (2): 151-8.
19. Mezer E, Babul-Hirji R, Wise R, Chipman M, DaSilva L, Rowell M, Thackray R, Shuman C T, Levin A V. Attitudes Regarding Predictive Testing for Retinitis Pigmentosa. Ophthalmic Genetics. 2007; 28(1):9-15.
20. Flannery J G, Farber D B, Bird A C, Bok D. Degenerative changes in a retina affected with autosomal dominant retinitis pigmentosa. Invest Ophthalmol Vis Sci. 1989; 30(2):191-211.
21. Curcio C A, Medeiros N E, Millican C L. Photoreceptor loss in age-related macular degeneration. Invest Ophthalmol Vis Sci. 1996; 37(7):1236-49.
22. Hartong D T, Berson E L, Dryja T P. Retinitis pigmentosa. Lancet. 2006; 368(9549):1795-809.
23. Chader G J. Animal models in research on retinal degenerations: past progress and future hope. Vision Res. 2002; 42(4):393-9. PubMed PMID: 11853755.
24. Li Z Y, Jacobson S G, Milam A H. Autosomal dominant retinitis pigmentosa caused by the threonine-17-methionine rhodopsin mutation: retinal histopathology and immunocytochemistry. Exp Eye Res. 1994; 58(4):397-408.
25. Grover S, Fishman G A, Anderson R J, Alexander K R, Derlacki D J. Rate of visual field loss in retinitis pigmentosa. Ophthalmology. 1997; 104 (3):460-5.
26. Baumgartner W A. Etiology, pathogenesis, and experimental treatment of retinitis pigmentosa. Medical Hypotheses. 2000; 54(5):814-24.
27. Sahaboglu A, Paquet-Durand O, Dietter J, Dengler K, Bernhard-Kurz S, Ekstrom P A, Hitzmann B, Ueffing M, Paquet-Durand F. Retinitis pigmentosa: rapid neurodegeneration is governed by slow cell death mechanisms. Cell Death Dis. 2013; 4:e488.
28. Hamel C. Retinitis pigmentosa. Orphanet J Rare Dis. 2006; 1:40.
29. Xia Y, Peng X, Ren Q. Retinitis pigmentosa patients' attitudes toward participation in retinal prosthesis trials. Contemp Clin Trials. 2012; 33(4):628-32.
30. Yanai D, Weiland J D, Mahadevappa M, Greenberg R J, Fine I, Humayun M S. Visual performance using a retinal prosthesis in three subjects with retinitis pigmentosa. Am J Ophthalmol. 2007; 143(5):820-7.
31. Kusnyerik A, Greppmaier U, Wilke R, et al. Positioning of electronic subretinal implants in blind retinitis pigmentosa patients through multimodal assessment of retinal structures. Invest Ophthalmol Vis Sci. 2012; 53(7):3748-55.
32. Horsager A, Greenwald S H, Weiland J D, Humayun M S, Greenberg R J, McMahon M J, Boynton G M, Fine I. Predicting visual sensitivity in retinal prosthesis patients. Invest Ophthalmol Vis Sci. 2009; 50(4):1483-91.
33. de Balthasar C, Patel S, Roy A, Freda R, Greenwald S, Horsager A, Mahadevappa M, Yanai D, McMahon M J, Humayun M S, Greenberg R J, Weiland J D, Fine I. Factors affecting perceptual thresholds in epiretinal prostheses. Invest Ophthalmol Vis Sci. 2008; 49(6):2303-14.
34. Zrenner E, Bartz-Schmidt K U, Benav H, Besch D, Bruckmann A, Gabel V P, Gekeler F, Greppmaier U, Harscher A, Kibbel S, Koch J, Kusnyerik A, Peters T, Stingl K, Sachs H, Stett A, Szurman P, Wilhelm B, Wilke R. Subretinal electronic chips allow blind patients to read letters and combine them to words. Proc Biol Sci. 2011; 278(1711):1489-97.
35. Chow A Y, Pardue M T, Perlman J I, et al. Subretinal implantation of semiconductor-based photodiodes: durability of novel implant designs. J Rehabilit Res Develop. 2002; 39(3):313-21.
36. Zrenner E. Will Retinal Implants Restore Vision? Science. 2002; 295(5557):1022-5.
37. Eckmiller R. Learning Retina Implants with Epiretinal Contacts. Ophthal Res. 1997; 29(5):281-9.
38. Bi A D, Cui J J, Ma Y P, Olshevskaya E, Pu M L, Dizhoor A M, Pan Z H. Ectopic expression of a microbial-type rhodopsin restores visual responses in mice with photoreceptor degeneration. Neuron. 2006; 50(1):23-33.
39. Thyagarajan S, van Wyk M, Lehmann K, Lowel S, Feng G, Wassle H. Visual Function in Mice with Photoreceptor Degeneration and Transgenic Expression of Channelrhodopsin 2 in Ganglion Cells. J Neurosci. 2010; 30(26): 8745-58.
40. Bi A, Cui J, Ma Y P, Olshevskaya E, Pu M, Dizhoor A M, Pan Z H. Ectopic expression of a microbial-type rhodopsin restores visual responses in mice with photoreceptor degeneration. Neuron. 2006; 50(1):23-33.
41. Zhang Y, Ivanova E, Bi A, Pan Z-H. Ectopic Expression of Multiple Microbial Rhodopsins Restores O N and OFF Light Responses in Retinas with Photoreceptor Degeneration. J Neurosci. 2009; 29(29):9186-96.
42. Tomita H, Sugano E, Isago H, Hiroi T, Wang Z, Ohta E, Tamai M Channelrhodopsin-2 gene transduced into retinal ganglion cells restores functional vision in genetically blind rats. Experimental Eye Research. 2010; 90(3):429-36.
43. Tomita H, Sugano E, Fukazawa Y, et al. Visual Properties of Transgenic Rats Harboring the Channelrhodopsin-2 Gene Regulated by the Thy-1.2 Promoter. PLoS One. 2009; 4(11).
44. Lagali P S, Balya D, Awatramani G B, Munch T A, Kim D S, Busskamp V, Cepko C L, Roska B. Light-activated channels targeted to O N bipolar cells restore visual function in retinal degeneration. Nat Neurosci. 2008; 11(6):667-75.
45. Doroudchi M M, Greenberg K P, Liu J, et al. Virally delivered Channelrhodopsin-2 Safely and Effectively Restores Visual Function in Multiple Mouse Models of Blindness. Mol Ther. 2011; 19(7): 1220-9.
46. Koizumi A, Tanaka K F, Yamanaka A. The manipulation of neural and cellular activities by ectopic expression of melanopsin. Neurosci Res. 2013; 75(1):3-5.
47. Fehrentz T, Schonberger M, Trauner D. Optochemical genetics. Angew Chem Int Ed Engl. 2011; 50(51):12156-82.
48. Fernandez de Castro J P, Scott P A, Fransen J W, Demas J, DeMarco P J, Kaplan H J, McCall M A. Cone photoreceptors develop normally in the absence of functional rod photoreceptors in a transgenic swine model of retinitis pigmentosa. Invest Ophthalmol Vis Sci. 2014; 55(4): 2460-8.
49. Busskamp V, Duebel J, Balya D, Fradot M, Viney T J, Siegert S, Groner A C, Cabuy E, Forster V, Seeliger M, Biel M, Humphries P, Paques M, Mohand-Said S, Trono D, Deisseroth K, Sahel J A, Picaud S, Roska B. Genetic Reactivation of Cone Photoreceptors Restores Visual Responses in Retinitis Pigmentosa. Science. 2010; 329 (5990):413-7.
50. Degenaar P, Grossman N, Memon M A, Burrone J, Dawson M, Drakakis E, Neil M, Nikolic K. Optobionic vision-a new genetically enhanced light on retinal prosthesis. Journal of neural engineering. 2009; 6(3): 035007.
51. Batabyal S, Cervenka G, Birch D, Kim Y-t, Mohanty S. Broadband activation by white-opsin lowers intensity threshold for cellular stimulation. Sci Rep-Uk. 2015; 5: 17857.
52. Klapoetke N C, Murata Y, Kim S S, et al., Independent optical excitation of distinct neural populations. Nat Methods. 2014; 11(3):338-46.
53. Lin J Y, Knutsen P M, Muller A, Kleinfeld D, Tsien R Y. ReaChR: a red-shifted variant of channelrhodopsin enables deep transcranial optogenetic excitation. Nat Neurosci. 2013; 16(10): 1499-508.
54. Warren E J, Allen C N, Brown R L, Robinson D W. Intrinsic light responses of retinal ganglion cells projecting to the circadian system. Eur J Neurosci. 2003; 17(9): 1727-35.
55. Hodges H. Maze procedures: the radial-arm and water maze compared. Brain Res Cogn Brain Res. 1996; 3(3-4):167-81.
56. Wright W, Gajjeraman S, Batabyal S, Pradhan S, Bhattacharya S, Mahapatra V, Tripathy A, Mohanty S. Restoring vision in mice with retinal degeneration using multicharacteristic opsin. Neurophotonics. 2017; 4(4): 041412.
57. Prusky G T, Alam N M, Beekman S, Douglas R M. Rapid quantification of adult and developing mouse spatial vision using a virtual optomotor system. Invest Ophthalmol Vis Sci. 2004; 45(12):4611-6.
58. Douglas R M, Alam N M, Silver B D, McGill T J, Tschetter W W, Prusky G T. Independent visual threshold measurements in the two eyes of freely moving rats and mice using a virtual-reality optokinetic system. Vis Neurosci. 2005; 22(5):677-84.
59. Li S, Huang L. Nonviral gene therapy: promises and challenges. Gene Ther. 2000; 7(1):31-4.
60. Thomas C E, Ehrhardt A, Kay M A. Progress and problems with the use of viral vectors for gene therapy. Nat Rev Genet. 2003; 4(5):346-58.

The invention claimed is:

1. A recombinant, ambient-light activatable, enhanced Multi-Characteristic Opsin (eMCO1) chimeric protein having SEQ ID NO: 11, wherein the chimeric protein consists of SEQ ID NO: 1 and a stabilizer-biomarker sequence;
   wherein the stabilizer-biomarker sequence is the translated sequence of SEQ ID NO: 10;
   wherein SEQ ID NO: 1 comprises 14 trans-membrane domains;
   wherein SEQ ID NO:1 comprises S132C, 5304A, 5308A and E610D mutations;
   wherein the stabilizer-biomarker is connected downstream with the 14 trans-membrane domains.

2. The eMCO1 chimeric protein of claim 1, further comprising
   a deletion of 7 amino acid residues from 309 to 315 in SEQ ID NO: 11; and
   a S132L mutation in the trans-membrane domain 2 of SEQ ID NO: 11
   wherein the resulted mutated sequence is represented by SEQ ID NO: 3.

3. The eMCO1 chimeric protein of claim 2, further comprising E473A, D603A, R469A of SEQ ID NO: 3.

4. The eMCO1 chimeric protein of claim 2, further comprising an insertion of trans-membrane sequence (SEQ ID NO: 14) after amino acid residue 315 in eMCO1, and wherein the resulted sequence is represented by SEQ ID NO: 5.

5. The eMCO1 chimeric protein of claim 1, further comprising one or more of a single or combination of mutations,
   wherein the mutation is selected from at least one of:
   E to A substitution at an amino acid residue corresponding to amino acid 123;
   D to A substitution at an amino acid residue corresponding to amino acid 253;
   R to A substitution at an amino acid residue corresponding to amino acid 120;
   Q to A, substitution at an amino acid residue corresponding to amino acid 56;
   K to A substitution at an amino acid residue corresponding to amino acid 93;
   E to A substitution at an amino acid residue corresponding to amino acid 90;
   E to Q substitution at an amino acid residue corresponding to amino acid 90;
   E to A substitution at an amino acid residue corresponding to amino acid 97;
   E to A substitution at an amino acid residue corresponding to amino acid 101;
   N to D substitution at an amino acid residue corresponding to amino acid 258;
   E to T substitution at an amino acid residue corresponding to amino acid 83;
   E to T substitution at an amino acid residue corresponding to amino acid 123; or
   S to D substitution at an amino acid residue corresponding to amino acid 63 of the eMCO1 chimeric protein sequence.

6. The eMCO1 chimeric protein of claim 1, wherein a light emitted from the stabilizer-biomarker stabilizes eMCO1 expression in a membrane with higher percentage of beta sheets and lower percentage of disordered structure and is less prone to cleavage that a non-modified eMCO1;
   wherein the stabilizer-biomarker molecule enhances a photo-induced current in cells expressing eMCO1 by better orientation-stabilization of eMCO1 across a membrane;
   wherein the stabilizer-biomarker molecule enhances a photo-induced current in cells expressing eMCO1 by light emitted or re-emitted from the stabilizer-biomarker molecule;
   wherein a promoter is used upstream to eMCO1 to target specific cells;
   wherein the promoter-eMCO1 gene is packaged in a vector;
   wherein cells can be transfected with the promoter-eMCO1 gene using chemical, viral, or physical transfection;
   wherein an examination of eMCO1 containing stabilizer-biomarker expression in the retina by fundoscopy is an indicator to determine efficacy of gene delivery to a targeted tissue(s); and
   wherein light emitted or re-emitted by the stabilizer-biomarker is used to determine a presence of eMCO1 expression; or
   wherein a loss of expression requires re-delivery of the promoter-eMCO1 gene to re-photosensitize or functionalize target cells.

* * * * *

SEQUENCE LISTING

```
<160> NUMBER OF SEQ ID NOS: 14

<210> SEQ ID NO 1
<211> LENGTH: 665
<212> TYPE: PRT
<213> ORGANISM: Artificial Sequence
<220> FEATURE:
<223> OTHER INFORMATION: Synthetic peptide

<400> SEQUENCE: 1

Met Asp Tyr Gly Gly Ala Leu Ser Ala Val Gly Arg Glu Leu Leu Phe
1               5                   10                  15

Val Thr Asn Pro Val Val Asn Gly Ser Val Leu Val Pro Glu Asp
            20                  25                  30

Gln Cys Tyr Cys Ala Gly Trp Ile Glu Ser Arg Gly Thr Asn Gly Ala
        35                  40                  45

Gln Thr Ala Ser Asn Val Leu Gln Trp Leu Ala Ala Gly Phe Ser Ile
    50                  55                  60

Leu Leu Leu Met Phe Tyr Ala Tyr Gln Thr Trp Lys Ser Thr Cys Gly
65                  70                  75                  80

Trp Glu Glu Ile Tyr Val Cys Ala Ile Glu Met Val Lys Val Ile Leu
                85                  90                  95

Glu Phe Phe Phe Glu Phe Lys Asn Pro Ser Met Leu Tyr Leu Ala Thr
            100                 105                 110

Gly His Arg Val Gln Trp Leu Arg Tyr Ala Glu Trp Leu Leu Thr Cys
        115                 120                 125

Pro Val Ile Ser Ile His Leu Ser Asn Leu Thr Gly Leu Ser Asn Asp
```

```
               130                 135                 140
Tyr Ser Arg Arg Thr Met Gly Leu Leu Val Ser Asp Ile Gly Thr Ile
145                 150                 155                 160

Val Trp Gly Ala Thr Ser Ala Met Ala Thr Gly Tyr Val Lys Val Ile
                165                 170                 175

Phe Phe Cys Leu Gly Leu Cys Tyr Gly Ala Asn Thr Phe Phe His Ala
                180                 185                 190

Ala Lys Ala Tyr Ile Glu Gly Tyr His Thr Val Pro Lys Gly Arg Cys
                195                 200                 205

Arg Gln Val Val Thr Gly Met Ala Trp Leu Phe Phe Val Ser Trp Gly
                210                 215                 220

Met Phe Pro Ile Leu Phe Ile Leu Gly Pro Glu Gly Phe Gly Val Leu
225                 230                 235                 240

Ser Val Tyr Gly Ser Thr Val Gly His Thr Ile Ile Asp Leu Met Ser
                245                 250                 255

Lys Asn Cys Trp Gly Leu Leu Gly His Tyr Leu Arg Val Leu Ile His
                260                 265                 270

Glu His Ile Leu Ile His Gly Asp Ile Arg Lys Thr Thr Lys Leu Asn
                275                 280                 285

Ile Gly Gly Thr Glu Ile Glu Val Glu Thr Leu Val Glu Asp Glu Ser
                290                 295                 300

Glu Ala Gly Ser Val Asn Lys Gly Thr Gly Lys Met Ala Glu Leu Ile
305                 310                 315                 320

Ser Ser Ala Thr Arg Ser Leu Phe Ala Ala Gly Gly Ile Asn Pro Trp
                325                 330                 335

Pro Asn Pro Tyr His His Glu Asp Met Gly Cys Gly Gly Met Thr Pro
                340                 345                 350

Thr Gly Glu Cys Phe Ser Thr Glu Trp Trp Cys Asp Pro Ser Tyr Gly
                355                 360                 365

Leu Ser Asp Ala Gly Tyr Gly Tyr Cys Phe Val Glu Ala Thr Gly Gly
                370                 375                 380

Tyr Leu Val Val Gly Val Glu Lys Lys Gln Ala Trp Leu His Ser Arg
385                 390                 395                 400

Gly Thr Pro Gly Glu Lys Ile Gly Ala Gln Val Cys Gln Trp Ile Ala
                405                 410                 415

Phe Ser Ile Ala Ile Ala Leu Leu Thr Phe Tyr Gly Phe Ser Ala Trp
                420                 425                 430

Lys Ala Thr Cys Gly Trp Glu Glu Val Tyr Val Cys Cys Val Glu Val
                435                 440                 445

Leu Phe Val Thr Leu Glu Ile Phe Lys Glu Phe Ser Ser Pro Ala Thr
                450                 455                 460

Val Tyr Leu Ser Thr Gly Asn His Ala Tyr Cys Leu Arg Tyr Phe Glu
465                 470                 475                 480

Trp Leu Leu Ser Cys Pro Val Ile Leu Ile Arg Leu Ser Asn Leu Ser
                485                 490                 495

Gly Leu Lys Asn Asp Tyr Ser Lys Arg Thr Met Gly Leu Ile Val Ser
                500                 505                 510

Cys Val Gly Met Ile Val Phe Gly Met Ala Ala Gly Leu Ala Thr Asp
                515                 520                 525

Trp Leu Lys Trp Leu Leu Tyr Ile Val Ser Cys Ile Tyr Gly Gly Tyr
                530                 535                 540

Met Tyr Phe Gln Ala Ala Lys Cys Tyr Val Glu Ala Asn His Ser Val
545                 550                 555                 560
```

```
Pro Lys Gly His Cys Arg Met Val Val Lys Leu Met Ala Tyr Ala Tyr
            565                 570                 575

Phe Ala Ser Trp Gly Ser Tyr Pro Ile Leu Trp Ala Val Gly Pro Glu
            580                 585                 590

Gly Leu Leu Lys Leu Ser Pro Tyr Ala Asn Ser Ile Gly His Ser Ile
            595                 600                 605

Cys Glu Ile Ile Ala Lys Glu Phe Trp Thr Phe Leu Ala His His Leu
            610                 615                 620

Arg Ile Lys Ile His Glu His Ile Leu Ile His Gly Asp Ile Arg Lys
625                 630                 635                 640

Thr Thr Lys Met Glu Ile Gly Gly Glu Glu Val Glu Val Glu Glu Phe
            645                 650                 655

Val Glu Glu Glu Asp Glu Asp Thr Val
            660                 665

<210> SEQ ID NO 2
<211> LENGTH: 1995
<212> TYPE: DNA
<213> ORGANISM: Artificial Sequence
<220> FEATURE:
<223> OTHER INFORMATION: Synthetic primer

<400> SEQUENCE: 2
atggattatg gcggcgcgct gagcgcggtg ggccgcgaac tgctgtttgt gaccaacccg      60
gtggtggtga acggcagcgt gctggtgccg aagatcagt gctattgcgc gggctggatt     120
gaaagccgcg gcaccaacgg cgcgcagacc gcgagcaacg tgctgcagtg gctggcggcg     180
ggctttagca ttctgctgct gatgttttat gcgtatcaga cctggaaaag cacctgcggc     240
tgggaagaaa tttatgtgtg cgcgattgaa atggtgaaag tgattctgga attttttttt     300
gaatttaaaa acccgagcat gctgtatctg gcgaccggcc atcgcgtgca gtggctgcgc     360
tatgcggaat ggctgctgac ctgcccggtg attagcattc atctgagcaa cctgaccggc     420
ctgagcaacg attatagccg ccgcaccatg ggcctgctgg tgagcgatat tggcaccatt     480
gtgtggggcg cgaccagcgc gatggcgacc ggctatgtga agtgattttt ttttgcctg      540 ggcctgtgct atggcgcgaa cacctttttt catgcggcga aagcgtatat tgaaggctat     600
cataccgtgc cgaaaggccg ctgccgccag gtggtgaccg gcatggcgtg gctgtttttt     660
gtgagctggg gcatgtttcc gattctgttt attctgggcc cggaaggctt tggcgtgctg     720
agcgtgtatg gcagcaccgt gggccatacc attattgatc tgatgagcaa aaactgctgg     780
ggcctgctgg gccattatct gcgcgtgctg attcatgaac atattctgat tcatggcgat     840
attcgcaaaa ccaccaaact gaacattggc ggcaccgaaa ttgaagtgga acccctggtg     900
gaagatgaat cggaagcggg ctcggtgaac aaaggcaccg gcaaaatggc tgagctgatc     960
agcagcgcca ccagatctct gtttgccgcc ggaggcatca acccttggcc taaccctac    1020 cacaccgagg acatgggctg tggaggaatg acacctacag gcgagtgctt cagcaccgag    1080
tggtggtgtg acccttctta cggactgagc gacgccggat acggatattg cttcgtggag    1140
gccacaggcg gctacctggt cgtgggagtg gagaagaagc aggcttggct gcacagcaga    1200
ggcacaccag agaaaagat cggcgcccag gtctgccagt ggattgcttt cagcatcgcc    1260
atcgccctgc tgacattcta cggcttcagc gcctggaagg ccacttgcgg ttgggaggag    1320
gtctacgtct gttgcgtcga ggtgctgttc gtgaccctgg agatcttcaa ggagttcagc    1380
agccccgcca cagtgtacct gtctaccggc aaccacgcct attgcctgcg ctacttcgag    1440
```

```
tggctgctgt cttgccccgt gatcctgatc agactgagca acctgagcgg cctgaagaac    1500
gactacagca agcggaccat gggcctgatc gtgtcttgcg tgggaatgat cgtgttcggc    1560
atggccgcag gactggctac cgattggctc aagtggctgc tgtatatcgt gtcttgcatc    1620
tacgccggct acatgtactt ccaggccgcc aagtgctacg tggaagccaa ccacagcgtg    1680
cctaaaggcc attgccgcat ggtcgtgaag ctgatggcct acgcttactt cgcctcttgg    1740
ggcagctacc caatcctctg gcagtgggga ccagaaggac tgctgaagct gagcccttac    1800
gccaacagca tcggccacag catctgcgag atcatcgcca aggagttttg daccttcctg    1860
gcccaccacc tgaggatcaa gatccacgag cacatcctga tccacggcga catccggaag    1920
accaccaaga tggagatcgg aggcgaggag gtggaagtgg aagagttcgt ggaggaggag    1980
gacgaggaca cagtg                                                     1995
```

<210> SEQ ID NO 3
<211> LENGTH: 658
<212> TYPE: PRT
<213> ORGANISM: Artificial Sequence
<220> FEATURE:
<223> OTHER INFORMATION: Synthetic peptide

<400> SEQUENCE: 3

```
Met Asp Tyr Gly Gly Ala Leu Ser Ala Val Gly Arg Glu Leu Leu Phe
1               5                   10                  15

Val Thr Asn Pro Val Val Asn Gly Ser Val Leu Val Pro Glu Asp
            20                  25                  30

Gln Cys Tyr Cys Ala Gly Trp Ile Glu Ser Arg Gly Thr Asn Gly Ala
        35                  40                  45

Gln Thr Ala Ser Asn Val Leu Gln Trp Leu Ala Ala Gly Phe Ser Ile
    50                  55                  60

Leu Leu Leu Met Phe Tyr Ala Tyr Gln Thr Trp Lys Ser Thr Cys Gly
65                  70                  75                  80

Trp Glu Glu Ile Tyr Val Cys Ala Ile Glu Met Val Lys Val Ile Leu
                85                  90                  95

Glu Phe Phe Phe Glu Phe Lys Asn Pro Ser Met Leu Tyr Leu Ala Thr
            100                 105                 110

Gly His Arg Val Gln Trp Leu Arg Tyr Ala Glu Trp Leu Leu Thr Cys
        115                 120                 125

Pro Val Ile Leu Ile His Leu Ser Asn Leu Thr Gly Leu Ser Asn Asp
    130                 135                 140

Tyr Ser Arg Arg Thr Met Gly Leu Leu Val Ser Asp Ile Gly Thr Ile
145                 150                 155                 160

Val Trp Gly Ala Thr Ser Ala Met Ala Thr Gly Tyr Val Lys Val Ile
                165                 170                 175

Phe Phe Cys Leu Gly Leu Cys Tyr Gly Ala Asn Thr Phe Phe His Ala
            180                 185                 190

Ala Lys Ala Tyr Ile Glu Gly Tyr His Thr Val Pro Lys Gly Arg Cys
        195                 200                 205

Arg Gln Val Val Thr Gly Met Ala Trp Leu Phe Phe Val Ser Trp Gly
    210                 215                 220

Met Phe Pro Ile Leu Phe Ile Leu Gly Pro Glu Gly Phe Gly Val Leu
225                 230                 235                 240

Ser Val Tyr Gly Ser Thr Val Gly His Thr Ile Ile Asp Leu Met Ser
                245                 250                 255
```

```
Lys Asn Cys Trp Gly Leu Leu Gly His Tyr Leu Arg Val Leu Ile His
                260                 265                 270

Glu His Ile Leu Ile His Gly Asp Ile Arg Lys Thr Thr Lys Leu Asn
            275                 280                 285

Ile Gly Gly Thr Glu Ile Glu Val Glu Thr Leu Val Glu Asp Glu Ser
        290                 295                 300

Glu Ala Gly Ser Met Ala Glu Leu Ile Ser Ser Ala Thr Arg Ser Leu
305                 310                 315                 320

Phe Ala Ala Gly Gly Ile Asn Pro Trp Pro Asn Pro Tyr His His Glu
                325                 330                 335

Asp Met Gly Cys Gly Gly Met Thr Pro Thr Gly Glu Cys Phe Ser Thr
            340                 345                 350

Glu Trp Trp Cys Asp Pro Ser Tyr Gly Leu Ser Asp Ala Gly Tyr Gly
        355                 360                 365

Tyr Cys Phe Val Glu Ala Thr Gly Gly Tyr Leu Val Val Gly Val Glu
    370                 375                 380

Lys Lys Gln Ala Trp Leu His Ser Arg Gly Thr Pro Gly Glu Lys Ile
385                 390                 395                 400

Gly Ala Gln Val Cys Gln Trp Ile Ala Phe Ser Ile Ala Ile Ala Leu
                405                 410                 415

Leu Thr Phe Tyr Gly Phe Ser Ala Trp Lys Ala Thr Cys Gly Trp Glu
            420                 425                 430

Glu Val Tyr Val Cys Cys Val Glu Val Leu Phe Val Thr Leu Glu Ile
        435                 440                 445

Phe Lys Glu Phe Ser Ser Pro Ala Thr Val Tyr Leu Ser Thr Gly Asn
450                 455                 460

His Ala Tyr Cys Leu Arg Tyr Phe Glu Trp Leu Leu Ser Cys Pro Val
465                 470                 475                 480

Ile Leu Ile Arg Leu Ser Asn Leu Ser Gly Leu Lys Asn Asp Tyr Ser
                485                 490                 495

Lys Arg Thr Met Gly Leu Ile Val Ser Cys Val Gly Met Ile Val Phe
            500                 505                 510

Gly Met Ala Ala Gly Leu Ala Thr Asp Trp Leu Lys Trp Leu Leu Tyr
        515                 520                 525

Ile Val Ser Cys Ile Tyr Gly Gly Tyr Met Tyr Phe Gln Ala Ala Lys
    530                 535                 540

Cys Tyr Val Glu Ala Asn His Ser Val Pro Lys Gly His Cys Arg Met
545                 550                 555                 560

Val Val Lys Leu Met Ala Tyr Ala Tyr Phe Ala Ser Trp Gly Ser Tyr
                565                 570                 575

Pro Ile Leu Trp Ala Val Gly Pro Glu Gly Leu Leu Lys Leu Ser Pro
            580                 585                 590

Tyr Ala Asn Ser Ile Gly His Ser Ile Cys Glu Ile Ala Lys Glu
        595                 600                 605

Phe Trp Thr Phe Leu Ala His Leu Arg Ile Lys Ile His Glu His
    610                 615                 620

Ile Leu Ile His Gly Asp Ile Arg Lys Thr Thr Lys Met Glu Ile Gly
625                 630                 635                 640

Gly Glu Glu Val Glu Val Glu Glu Phe Val Glu Glu Asp Glu Asp
                645                 650                 655

Thr Val

<210> SEQ ID NO 4
```

<211> LENGTH: 1998
<212> TYPE: DNA
<213> ORGANISM: Artificial Sequence
<220> FEATURE:
<223> OTHER INFORMATION: Synthetic primer

<400> SEQUENCE: 4

| | | | | | |
|---|---|---|---|---|---|
| atggactatg | gcggagcatt | gagtgcagtt | gggcgagaat | tgctgttcgt | gacgaatccc | 60 |
| gttgttgtaa | acggaagtgt | actggtgcca | gaagaccaat | gttattgcgc | gggctggata | 120 |
| gagtcgcgcg | gaacgaatgg | agcacagaca | gcgtccaacg | tactgcaatg | gctcgccgct | 180 |
| ggtttctcta | tcctgttgtt | gatgttctac | gcatatcaaa | cgtggaaaag | cacctgcggg | 240 |
| tgggaggaaa | tatatgtgtg | tgccatcgag | atggtaaaag | taattttaga | gttttttttt | 300 |
| gaattcaaga | cccctcaat | gttgtaccct | gctacggggc | atagagttca | atggcttcgg | 360 |
| tatgcggaat | ggctcttgac | atgtccagta | atactaattc | atcttagtaa | cttaacggga | 420 |
| ctctctaacg | actattcacg | gcgtaccatg | ggactactgg | tgtcagacat | gggacgata | 480 |
| gtatgggag | cgacgagcgc | aatggctaca | ggctacgtaa | aggttatctt | tttctgcctc | 540 |
| gggctttgtt | acggcgcgaa | taccttcttt | catgccgcaa | aggcctacat | agagggttac | 600 |
| cataccgtac | cgaaagggcg | gtgccggcaa | gtcgtcacag | gaatggcttg | gctcttcttt | 660 |
| gtgagttggg | gaatgttccc | tatcctattt | atcttagggc | ctgagggttt | cggcgtgctt | 720 |
| agtgtttacg | gcagtacggt | cggtcacacg | atcatcgacc | tgatgtcaaa | gaattgctgg | 780 |
| ggcttgcttg | gtcattattt | gcgtgtgtta | atccacgaac | atattctgat | tcatggtgac | 840 |
| atccgaaaaa | ctaccaaact | caatattggc | ggcacagaga | tagaggttga | aacgttggtc | 900 |
| gaggacgagt | ctgaagcggg | gtcaatggcg | gaactaattt | catctgcaac | acggtcgcta | 960 |
| tttgctgccg | gggggataaa | tccctggccc | aacccgtatc | accacgaaga | tatgggatgc | 1020 |
| ggagggatga | ctcccacagg | agagtgtttt | tcgaccgaat | ggtggtgtga | cccctcgtac | 1080 |
| gggttatcag | atgcaggcta | tggttattgt | ttcgtggagg | ccacgggtgg | ttatttagtc | 1140 |
| gtaggggtag | agaagaaaca | ggcatggctt | cattcccggg | gaaccccgg | ggagaaaatt | 1200 |
| ggagctcagg | tatgccagtg | gatagcgttt | tctatcgcga | tagctctcct | gacttttat | 1260 |
| ggattttcgg | cttggaaggc | cacgtgcgga | tgggaagagg | tatacgtatg | ttgcgtcgaa | 1320 |
| gtgcttttcg | taactctgga | aatatttaaa | gaattctcaa | gtccggccac | agtttatttg | 1380 |
| agcactggca | accacgccta | ttgtttgcgg | tattttgagt | ggctattatc | ttgccctgtt | 1440 |
| attcttatac | ggttatcaaa | cctatcgggt | ctgaagaatg | attattccaa | gagaaccatg | 1500 |
| ggcctaattg | tcagttgcgt | cgggatgatc | gtgttcggga | tggccgcggg | tcttgcaacg | 1560 |
| gactggctta | agtggctatt | atacatcgtc | agctgcattt | acggtggtta | catgtacttt | 1620 |
| caagcggcta | agtgctatgt | ggaggcgaac | cattcagtcc | cgaaaggcca | ctgtcgcatg | 1680 |
| gtggttaagt | taatgcgta | tgcgtacttc | gcttcgtggg | gttcatatcc | aatcctgtgg | 1740 |
| gcggtcggac | ctgaaggtct | cctgaaactg | agccccatg | cgaactccat | aggacattcc | 1800 |
| atctgtgaga | tcatcgccaa | ggaattctgg | accttcttag | ctcaccattt | gcggattaag | 1860 |
| atccatgaac | acattctcat | tcacggtgat | attaggaaaa | ctaccaagat | ggagataggt | 1920 |
| ggagaagagg | tggaggtaga | agagtttgta | gaagaggagg | acgaggacac | tgtagtatca | 1980 |
| aaggggggaag | aagacaat | | | | | 1998 |

<210> SEQ ID NO 5
<211> LENGTH: 699

```
<212> TYPE: PRT
<213> ORGANISM: Artificial Sequence
<220> FEATURE:
<223> OTHER INFORMATION: Synthetic peptide

<400> SEQUENCE: 5

Met Asp Tyr Gly Gly Ala Leu Ser Ala Val Gly Arg Glu Leu Leu Phe
1               5                   10                  15

Val Thr Asn Pro Val Val Asn Gly Ser Val Leu Val Pro Glu Asp
            20                  25                  30

Gln Cys Tyr Cys Ala Gly Trp Ile Glu Ser Arg Gly Thr Asn Gly Ala
                35                  40                  45

Gln Thr Ala Ser Asn Val Leu Gln Trp Leu Ala Ala Gly Phe Ser Ile
        50                  55                  60

Leu Leu Leu Met Phe Tyr Ala Tyr Gln Thr Trp Lys Ser Thr Cys Gly
65                  70                  75                  80

Trp Glu Glu Ile Tyr Val Cys Ala Ile Glu Met Val Lys Val Ile Leu
                85                  90                  95

Glu Phe Phe Phe Glu Phe Lys Asn Pro Ser Met Leu Tyr Leu Ala Thr
            100                 105                 110

Gly His Arg Val Gln Trp Leu Arg Tyr Ala Glu Trp Leu Leu Thr Cys
                115                 120                 125

Pro Val Ile Ser Ile His Leu Ser Asn Leu Thr Gly Leu Ser Asn Asp
130                 135                 140

Tyr Ser Arg Arg Thr Met Gly Leu Leu Val Ser Asp Ile Gly Thr Ile
145                 150                 155                 160

Val Trp Gly Ala Thr Ser Ala Met Ala Thr Gly Tyr Val Lys Val Ile
                165                 170                 175

Phe Phe Cys Leu Gly Leu Cys Tyr Gly Ala Asn Thr Phe Phe His Ala
            180                 185                 190

Ala Lys Ala Tyr Ile Glu Gly Tyr His Thr Val Pro Lys Gly Arg Cys
        195                 200                 205

Arg Gln Val Val Thr Gly Met Ala Trp Leu Phe Phe Val Ser Trp Gly
210                 215                 220

Met Phe Pro Ile Leu Phe Ile Leu Gly Pro Glu Gly Phe Gly Val Leu
225                 230                 235                 240

Ser Val Tyr Gly Ser Thr Val Gly His Thr Ile Ile Asp Leu Met Ser
                245                 250                 255

Lys Asn Cys Trp Gly Leu Leu Gly His Tyr Leu Arg Val Leu Ile His
            260                 265                 270

Glu His Ile Leu Ile His Gly Asp Ile Arg Lys Thr Thr Lys Leu Asn
        275                 280                 285

Ile Gly Gly Thr Glu Ile Glu Val Glu Thr Leu Val Glu Asp Glu Ser
290                 295                 300

Glu Ala Gly Ser Val Asn Lys Gly Thr Gly Lys Thr Pro Ala Arg Trp
305                 310                 315                 320

Val Trp Ile Ser Leu Tyr Tyr Ala Ala Phe Tyr Val Val Met Thr Gly
                325                 330                 335

Leu Phe Ala Leu Cys Ile Tyr Val Leu Met Gln Thr Ile Met Ala Glu
            340                 345                 350

Leu Ile Ser Ser Ala Thr Arg Ser Leu Phe Ala Ala Gly Gly Ile Asn
        355                 360                 365

Pro Trp Pro Asn Pro Tyr His His Glu Asp Met Gly Cys Gly Gly Met
370                 375                 380
```

-continued

```
Thr Pro Thr Gly Glu Cys Phe Ser Thr Glu Trp Trp Cys Asp Pro Ser
385                 390                 395                 400

Tyr Gly Leu Ser Asp Ala Gly Tyr Gly Tyr Cys Phe Val Glu Ala Thr
            405                 410                 415

Gly Gly Tyr Leu Val Gly Val Glu Lys Lys Gln Ala Trp Leu His
        420                 425                 430

Ser Arg Gly Thr Pro Gly Glu Lys Ile Gly Ala Gln Val Cys Gln Trp
        435                 440                 445

Ile Ala Phe Ser Ile Ala Ile Ala Leu Leu Thr Phe Tyr Gly Phe Ser
    450                 455                 460

Ala Trp Lys Ala Thr Cys Gly Trp Glu Val Tyr Val Cys Val
465                 470                 475                 480

Glu Val Leu Phe Val Thr Leu Glu Ile Phe Lys Glu Phe Ser Ser Pro
            485                 490                 495

Ala Thr Val Tyr Leu Ser Thr Gly Asn His Ala Tyr Cys Leu Arg Tyr
        500                 505                 510

Phe Glu Trp Leu Leu Ser Cys Pro Val Ile Leu Ile Arg Leu Ser Asn
    515                 520                 525

Leu Ser Gly Leu Lys Asn Asp Tyr Ser Lys Arg Thr Met Gly Leu Ile
530                 535                 540

Val Ser Cys Val Gly Met Ile Val Phe Gly Met Ala Ala Gly Leu Ala
545                 550                 555                 560

Thr Asp Trp Leu Lys Trp Leu Leu Tyr Ile Val Ser Cys Ile Tyr Gly
            565                 570                 575

Gly Tyr Met Tyr Phe Gln Ala Ala Lys Cys Tyr Val Glu Ala Asn His
        580                 585                 590

Ser Val Pro Lys Gly His Cys Arg Met Val Val Lys Leu Met Ala Tyr
    595                 600                 605

Ala Tyr Phe Ala Ser Trp Gly Ser Tyr Pro Ile Leu Trp Ala Val Gly
610                 615                 620

Pro Glu Gly Leu Leu Lys Leu Ser Pro Tyr Ala Asn Ser Ile Gly His
625                 630                 635                 640

Ser Ile Cys Glu Ile Ile Ala Lys Glu Phe Trp Thr Phe Leu Ala His
            645                 650                 655

His Leu Arg Ile Lys Ile His Glu His Ile Leu Ile His Gly Asp Ile
        660                 665                 670

Arg Lys Thr Thr Lys Met Glu Ile Gly Gly Glu Val Glu Val Glu
    675                 680                 685

Glu Phe Val Glu Glu Glu Asp Glu Asp Thr Val
690                 695
```

<210> SEQ ID NO 6
<211> LENGTH: 2097
<212> TYPE: DNA
<213> ORGANISM: Artificial Sequence
<220> FEATURE:
<223> OTHER INFORMATION: Synthetic primer

<400> SEQUENCE: 6

```
atggattacg gaggagcact gagcgctgtt ggccgcgagt tgctatttgt gaccaacccc     60
gtcgtggtca atggcagcgt ccttgtgcct gaggatcaat gttattgcgc tgggtggatt    120
gaatcccgag gtacaaatgg tgcccagacg gcaagcaacg ttttgcaatg gctagcagct    180
gggttttcaa ttctactttt aatgttttac gctatcaaa cctggaagag tacatgtggc    240
tgggaggaaa tttatgtctg cgctattgaa atggttaaag taattttgga atttttttt     300
```

-continued

```
gaatttaaga atccatcaat gttgtatctt gccacaggtc acagggtcca atggctccga    360
tacgcggaat ggcttctaac ttgccctgtt atttccattc acctaagcaa tctgactggc    420
ctttcgaatg actatagcag acgcaccatg ggactgttag ttagtgacat agggactata    480
gtttggggtg ccactagcgc catggcgacc ggttatgtta agtaattttt tttctgcctt    540
gggttgtgtt atggcgctaa cacttttttc cacgctgcta agcatatat agaagggtac    600 catacggtgc ccaaaggaag atgtcgccaa gtagttacag ggatggcgtg gctgttcttt    660
gtgagctggg ggatgttccc tatactgttt atccttggtc cagagggttt ggagtccta    720 agcgtgtacg gcagtactgt tgggcatact ataatagatt tgatgagcaa aaactgctgg    780
gggcttctcg ggcattattt acgagttctt attcacgaac atattttaat tcatggggat    840
atcagaaaaa caacgaaact aaatatagga ggcacgaaaa tagaggttga aacgctcgtc    900
gaagacgaat cagaggccgg ctccgtgaat aagggaactg gtaaaactcc tgctcgctgg    960
gtatggatat cgctttacta cgcagcattt tacgtagtta tgactgggct ttttgctttg   1020
tgcatatacg tgctaatgca gacgattatg gctgagctaa tttcatctgc aactagatcc   1080
cttttcgcgg caggagggat caaccccctgg cccaatccat atcatcatga agatatgggc   1140
tgtggcggta tgaccccaac tggtgagtgc ttttctaccg aatggtggtg tgatccgagt   1200
tacggtctgt cagatgctgg gtatggttat tgctttgtcg aagccacggg gggataccttt  1260 gtcgtcggag tagagaaaaa acaggcctgg ctccattccc gggggacccc aggagagaag   1320
ataggggccc aagtttgcca gtggatcgca tttagtattg cgatcgcatt actgacattc   1380
tatggtttct cagcgtggaa ggcaacctgc ggctgggagg aggtttacgt atgctgtgtt   1440
gaggtactgt tcgtaaccct tgagattttc aaagagtttt cttctccggc gacggtctat   1500
ctcagtaccg gtaaccatgc atattgttta cgttatttcg aatggttgct tcttgccca    1560 gtgattttga tacgcttgag taatttatct ggcctaaaga acgactatag caagcgaacc    1620
atgggactta ttgtatcttg tgttggcatg atagtttttg gtatggcagc cgggctcgcc    1680
actgactggc tgaagtggtt gctctatata gtgagctgta tttatggtgg ctacatgtac    1740
tttcaggcgg ccaagtgtta cgttgaagca aaccattcgg tacctaaagg acattgccgt    1800
atggtagtta agctgatggc gtatgcgtac ttcgcgagct ggggcagcta ccccattctg    1860
tgggcggtgg gaccagaggg gttacttaag ttgtcgccct atgctaattc aataggccat    1920
agcatctgtg agattatcgc gaaggaattt tggactttcc tagcacatca ccttcgaatt    1980
aaaatacacg aacacatact cattcacggg gacatacgca agacaaccaa gatgaaaatc    2040
ggaggtgagg aagtggaagt agaggagttt gtagaggagg aagatgagga cacggtt     2097
```

<210> SEQ ID NO 7
<211> LENGTH: 691
<212> TYPE: PRT
<213> ORGANISM: Artificial Sequence
<220> FEATURE:
<223> OTHER INFORMATION: Synthetic peptide

<400> SEQUENCE: 7

```
Met Asp Tyr Gly Gly Ala Leu Ser Ala Val Gly Arg Glu Leu Leu Phe
1               5                   10                  15

Val Thr Asn Pro Val Val Asn Gly Ser Val Leu Val Pro Glu Asp
            20                  25                  30

Gln Cys Tyr Cys Ala Gly Trp Ile Glu Ser Arg Gly Thr Asn Gly Ala
        35                  40                  45
```

```
Gln Thr Ala Ser Asn Val Leu Gln Trp Leu Ala Ala Gly Phe Ser Ile
    50                  55                  60
Leu Leu Leu Met Phe Tyr Ala Tyr Gln Thr Trp Lys Ser Thr Cys Gly
65                  70                  75                  80
Trp Glu Glu Ile Tyr Val Cys Ala Ile Glu Met Val Lys Val Ile Leu
                85                  90                  95
Glu Phe Phe Phe Glu Phe Lys Asn Pro Ser Met Leu Tyr Leu Ala Thr
            100                 105                 110
Gly His Arg Val Gln Trp Leu Arg Tyr Ala Glu Trp Leu Leu Thr Cys
            115                 120                 125
Pro Val Ile Leu Ile His Leu Ser Asn Leu Thr Gly Leu Ser Asn Asp
    130                 135                 140
Tyr Ser Arg Arg Thr Met Gly Leu Leu Val Ser Asp Ile Gly Thr Ile
145                 150                 155                 160
Val Trp Gly Ala Thr Ser Ala Met Ala Thr Gly Tyr Val Lys Val Ile
                165                 170                 175
Phe Phe Cys Leu Gly Leu Cys Tyr Gly Ala Asn Thr Phe Phe His Ala
            180                 185                 190
Ala Lys Ala Tyr Ile Glu Gly Tyr His Thr Val Pro Lys Gly Arg Cys
            195                 200                 205
Arg Gln Val Val Thr Gly Met Ala Trp Leu Phe Phe Val Ser Trp Gly
    210                 215                 220
Met Phe Pro Ile Leu Phe Ile Leu Gly Pro Glu Gly Phe Gly Val Leu
225                 230                 235                 240
Ser Val Tyr Gly Ser Thr Val Gly His Thr Ile Ile Asp Leu Met Ser
                245                 250                 255
Lys Asn Cys Trp Gly Leu Leu Gly His Tyr Leu Arg Val Leu Ile His
            260                 265                 270
Glu His Ile Leu Ile His Gly Asp Ile Arg Lys Thr Thr Lys Leu Asn
            275                 280                 285
Ile Gly Gly Thr Glu Ile Glu Val Glu Thr Leu Val Glu Asp Glu Ser
    290                 295                 300
Glu Ala Gly Ser Pro Ala Arg Trp Val Trp Ile Ser Leu Tyr Tyr Ala
305                 310                 315                 320
Ala Phe Tyr Val Val Met Thr Gly Leu Phe Ala Leu Cys Ile Tyr Val
                325                 330                 335
Leu Met Gln Thr Ile Met Ala Glu Leu Ile Ser Ser Ala Thr Arg Ser
            340                 345                 350
Leu Phe Ala Ala Gly Gly Ile Asn Pro Trp Pro Asn Pro Tyr His His
            355                 360                 365
Glu Asp Met Gly Cys Gly Gly Met Thr Pro Thr Gly Glu Cys Phe Ser
    370                 375                 380
Thr Glu Trp Trp Cys Asp Pro Ser Tyr Gly Leu Ser Asp Ala Gly Tyr
385                 390                 395                 400
Gly Tyr Cys Phe Val Glu Ala Thr Gly Gly Tyr Leu Val Val Gly Val
                405                 410                 415
Glu Lys Lys Gln Ala Trp Leu His Ser Arg Gly Thr Pro Gly Glu Lys
            420                 425                 430
Ile Gly Ala Gln Val Cys Gln Trp Ile Ala Phe Ser Ile Ala Ile Ala
            435                 440                 445
Leu Leu Thr Phe Tyr Gly Phe Ser Ala Trp Lys Ala Thr Cys Gly Trp
    450                 455                 460
```

```
Glu Glu Val Tyr Val Cys Cys Val Glu Val Leu Phe Val Thr Leu Glu
465                 470                 475                 480

Ile Phe Lys Glu Phe Ser Ser Pro Ala Thr Val Tyr Leu Ser Thr Gly
            485                 490                 495

Asn His Ala Tyr Cys Leu Arg Tyr Phe Glu Trp Leu Leu Ser Cys Pro
        500                 505                 510

Val Ile Leu Ile Arg Leu Ser Asn Leu Ser Gly Leu Lys Asn Asp Tyr
    515                 520                 525

Ser Lys Arg Thr Met Gly Leu Ile Val Ser Cys Val Gly Met Ile Val
530                 535                 540

Phe Gly Met Ala Ala Gly Leu Ala Thr Asp Trp Leu Lys Trp Leu Leu
545                 550                 555                 560

Tyr Ile Val Ser Cys Ile Tyr Gly Gly Tyr Met Tyr Phe Gln Ala Ala
                565                 570                 575

Lys Cys Tyr Val Glu Ala Asn His Ser Val Pro Lys Gly His Cys Arg
            580                 585                 590

Met Val Val Lys Leu Met Ala Tyr Ala Tyr Phe Ala Ser Trp Gly Ser
            595                 600                 605

Tyr Pro Ile Leu Trp Ala Val Gly Pro Glu Gly Leu Leu Lys Leu Ser
610                 615                 620

Pro Tyr Ala Asn Ser Ile Gly His Ser Ile Cys Glu Ile Ile Ala Lys
625                 630                 635                 640

Glu Phe Trp Thr Phe Leu Ala His His Leu Arg Ile Lys Ile His Glu
                645                 650                 655

His Ile Leu Ile His Gly Asp Ile Arg Lys Thr Thr Lys Met Glu Ile
            660                 665                 670

Gly Gly Glu Glu Val Glu Val Glu Glu Phe Val Glu Glu Glu Asp Glu
            675                 680                 685

Asp Thr Val
        690

<210> SEQ ID NO 8
<211> LENGTH: 2073
<212> TYPE: DNA
<213> ORGANISM: Artificial Sequence
<220> FEATURE:
<223> OTHER INFORMATION: Synthetic primer

<400> SEQUENCE: 8
atggactatg gaggagcact gtcagccgtt gggagagagt tgttgtttgt taccaatcct      60
gtagtagtca atggcagtgt gcttgtacca gaggatcaat gctactgtgc cgggtggata     120
gagtcccggg gaaccaacgg ggcacaaact gcgagtaacg ttctgcaatg ctagcagca     180 ggctttagca tactgctact aatgttctat gcttaccaaa catggaagtc gacttgcggg     240
tgggaggaga tatacgtctg cgcaattgaa atggtcaagg ttattctcga gttcttcttc     300
gaattcaaaa acccatcaat gttatactta gcgacaggac atcgagtcca gtggttacgt     360
tacgccgagt ggctcctgac gtgcccggta atttaatcc acctctctaa tttgaccgga     420
ctttccaatg attacagtcg aagaactatg gggctattag tctctgacat cgggactatt     480
gtctggggtg cgactagcgc tatggctacc gggtatgtaa aagtcatctt cttctgttta     540
ggactgtgct acggcgcgaa tacattcttt cacgctgcga aagcttatat tgaaggctat     600
cacactgtac ctaaaggtcg gtgtaggcag gtcgtcaccg gtatggcgtg ttgttcttc     660 gtatcatggg gaatgtttcc aatcttgttt atactaggtc ccgaaggatt tggagtgttg     720
```

```
tccgtttacg gatcaacagt aggccacact attatcgatt tgatgtctaa aaactgctgg    780
gggcttttag gtcactatct aagggtgctc attcatgagc acatattaat ccatggcgat    840
atcagaaaga cgacgaaact gaatattgga ggcactgaga tcgaagtaga gacgcttgtc    900
gaagacgaat ccgaagctgg tagccccgca cgctgggtct ggatatcttt gtactatgcc    960
gccttctatg ttgttatgac aggactcttt gctttatgca tctatgtcct aatgcaaact   1020
attatggctg aacttatatc atcggcaaca aggagtttat ttgcggctgg gggaataaat   1080
ccgtggccca accctacca tcatgaagat atgggttgcg gcggcatgac cccgacaggg    1140
gaatgcttct cgacggagtg gtggtgtgat ccttcttatg gactgagtga tgctgggtat   1200
ggctattgct tcgtagaggc tacgggggg tacttggtcg ttggagtcga aaaaaacag     1260 gcatggttac atagcagggg gactcctgga gagaaaatag gtgcccaggt ttgtcaatgg   1320
attgctttct cgattgcaat agctctgtta acgttctatg ggttctccgc gtggaaggct   1380
acttgtggct gggaagaggt atatgttgt tgtgttgaag ttctatttgt aacacttgag    1440
atatttaaag aattttcttc acccgcaacg gtctacttaa gtacaggcaa tcatgcatac   1500
tgtctaagat acttcgaatg gctcttatca tgtccggtga tcttaattcg actctcgaac   1560
ctctctggac tcaagaatga ctatagtaag aggactatgg gactcattgt gtcgtgcgtt   1620
ggtatgattg tgtttggtat ggcggcaggg ctggctacgg actggctaaa gtggctgcta   1680
tatatagtga gctgtatcta tggcggttac atgtatttcc aggcggccaa gtgttatgtc   1740
gaggcgaatc actcggtccc caaaggtcat tgtcggatgg tggtcaagct tatggcgtac   1800
gcatatttcg ccagctgggg atcgtacccg atactttggg ccgttggccc agaagggcta   1860
ctaaagttga gcccgtacgc caattcaatt gggcatagta tctgtgagat aattgctaag   1920
gagttttgga cgttttttagc tcaccatctg agaattaaga ttcatgagca catcttaatt   1980
cacggggata tccgcaagac taccaagatg gagataggtg gggaggaggt ggaggtagaa   2040
gagtttgtag aagaagagga tgaagatact gta                                2073

<210> SEQ ID NO 9
<211> LENGTH: 200
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (6)..(7)
<223> OTHER INFORMATION: n is a, c, g, or t

<400> SEQUENCE: 9
cagggnngat tgattattga ctagtgatct ccagatggct aaacttttaa atcatgaatg     60
aagtagatat taccaaattg cttttttcagc atccatttag ataatcatgt tttttgcctt    120
taatctgtta atgtagtgaa ttacagaaat acatttccta aatcattaca tcccccaaat    180
cgttaatctg ctaaagtaca                                                200

<210> SEQ ID NO 10
<211> LENGTH: 681
<212> TYPE: DNA
<213> ORGANISM: Artificial Sequence
<220> FEATURE:
<223> OTHER INFORMATION: Synthetic primer

<400> SEQUENCE: 10
atggccatca tcaaggagtt catgcgcttc aaggtgcaca tggagggctc cggaacggcc     60
```

```
cgagttcgag atcgagggcg agggcgaggg ccgcccctac gagggcaccc agaccgccaa    120
gctgaaggtg accaagggtg gccccctgcc cttcgcctgg gacatcctgt ccctcagtt    180 catgtacggc tccaaggcct acgtgaagca ccccgccgac atccccgact acttgaagct    240
gtccttcccc gagggcttca gtgggagcg cgtgatgaac ttcgaggacg gcggcgtggt    300
gaccgtgacc caggactcct ccctgcagga cggcgagttc atctacaagg tgaagctgcg    360
cggcaccaac ttcccctccg acggcccccgt aatgcagaag aagaccatgg gctgggaggc    420
ctcctccgag cggatgtacc ccgaggacgg cgccctgaag ggcgagatca agcagaggct    480
gaagctgaag gacggcggcc actacacgct gaggtcaaga ccacctacaa ggccaagaag    540
cccgtgcagc tgcccggcgc ctacaacgtc aacatcaagt ggacatcac ctcccacaac    600 gaggactaca ccatcgtgga acagtacgaa cgcgccgagg ccgccactc caccggcggc    660 atggacgagc tgtacaagta a                                              681
```

```
<210> SEQ ID NO 11
<211> LENGTH: 900
<212> TYPE: PRT
<213> ORGANISM: Artificial Sequence
<220> FEATURE:
<223> OTHER INFORMATION: Synthetic peptide

<400> SEQUENCE: 11

Met Asp Tyr Gly Gly Ala Leu Ser Ala Val Gly Arg Glu Leu Leu Phe
1               5                   10                  15

Val Thr Asn Pro Val Val Asn Gly Ser Val Leu Val Pro Glu Asp
            20                  25                  30

Gln Cys Tyr Cys Ala Gly Trp Ile Glu Ser Arg Gly Thr Asn Gly Ala
        35                  40                  45

Gln Thr Ala Ser Asn Val Leu Gln Trp Leu Ala Ala Gly Phe Ser Ile
    50                  55                  60

Leu Leu Leu Met Phe Tyr Ala Tyr Gln Thr Trp Lys Ser Thr Cys Gly
65                  70                  75                  80

Trp Glu Glu Ile Tyr Val Cys Ala Ile Glu Met Val Lys Val Ile Leu
                85                  90                  95

Glu Phe Phe Phe Glu Phe Lys Asn Pro Ser Met Leu Tyr Leu Ala Thr
            100                 105                 110

Gly His Arg Val Gln Trp Leu Arg Tyr Ala Glu Trp Leu Leu Thr Cys
        115                 120                 125

Pro Val Ile Cys Ile His Leu Ser Asn Leu Thr Gly Leu Ser Asn Asp
    130                 135                 140

Tyr Ser Arg Arg Thr Met Gly Leu Leu Val Ser Asp Ile Gly Thr Ile
145                 150                 155                 160

Val Trp Gly Ala Thr Ser Ala Met Ala Thr Gly Tyr Val Lys Val Ile
                165                 170                 175

Phe Phe Cys Leu Gly Leu Cys Tyr Gly Ala Asn Thr Phe Phe His Ala
            180                 185                 190

Ala Lys Ala Tyr Ile Glu Gly Tyr His Thr Val Pro Lys Gly Arg Cys
        195                 200                 205

Arg Gln Val Val Thr Gly Met Ala Trp Leu Phe Phe Val Ser Trp Gly
    210                 215                 220

Met Phe Pro Ile Leu Phe Ile Leu Gly Pro Glu Gly Phe Gly Val Leu
225                 230                 235                 240

Ser Val Tyr Gly Ser Thr Val Gly His Thr Ile Ile Asp Leu Met Ser
```

```
            245                 250                 255
Lys Asn Cys Trp Gly Leu Leu Gly His Tyr Leu Arg Val Leu Ile His
            260                 265                 270

Glu His Ile Leu Ile His Gly Asp Ile Arg Lys Thr Thr Lys Leu Asn
            275                 280                 285

Ile Gly Gly Thr Glu Ile Glu Val Glu Thr Leu Val Glu Asp Glu Ala
            290                 295                 300

Glu Ala Gly Ala Val Asn Lys Gly Thr Gly Lys Met Ala Glu Leu Ile
305                 310                 315                 320

Ser Ser Ala Thr Arg Ser Leu Phe Ala Ala Gly Gly Ile Asn Pro Trp
            325                 330                 335

Pro Asn Pro Tyr His His Glu Asp Met Gly Cys Gly Gly Met Thr Pro
            340                 345                 350

Thr Gly Glu Cys Phe Ser Thr Glu Trp Trp Cys Asp Pro Ser Tyr Gly
            355                 360                 365

Leu Ser Asp Ala Gly Tyr Gly Tyr Cys Phe Val Glu Ala Thr Gly Gly
            370                 375                 380

Tyr Leu Val Val Gly Val Glu Lys Lys Gln Ala Trp Leu His Ser Arg
385                 390                 395                 400

Gly Thr Pro Gly Glu Lys Ile Gly Ala Gln Val Cys Gln Trp Ile Ala
            405                 410                 415

Phe Ser Ile Ala Ile Ala Leu Leu Thr Phe Tyr Gly Phe Ser Ala Trp
            420                 425                 430

Lys Ala Thr Cys Gly Trp Glu Glu Val Tyr Val Cys Cys Val Glu Val
            435                 440                 445

Leu Phe Val Thr Leu Glu Ile Phe Lys Glu Phe Ser Ser Pro Ala Thr
450                 455                 460

Val Tyr Leu Ser Thr Gly Asn His Ala Tyr Cys Leu Arg Tyr Phe Glu
465                 470                 475                 480

Trp Leu Leu Ser Cys Pro Val Ile Leu Ile Arg Leu Ser Asn Leu Ser
            485                 490                 495

Gly Leu Lys Asn Asp Tyr Ser Lys Arg Thr Met Gly Leu Ile Val Ser
            500                 505                 510

Cys Val Gly Met Ile Val Phe Gly Met Ala Ala Gly Leu Ala Thr Asp
            515                 520                 525

Trp Leu Lys Trp Leu Leu Tyr Ile Val Ser Cys Ile Tyr Gly Gly Tyr
            530                 535                 540

Met Tyr Phe Gln Ala Ala Lys Cys Tyr Val Glu Ala Asn His Ser Val
545                 550                 555                 560

Pro Lys Gly His Cys Arg Met Val Val Lys Leu Met Ala Tyr Ala Tyr
            565                 570                 575

Phe Ala Ser Trp Gly Ser Tyr Pro Ile Leu Trp Ala Val Gly Pro Glu
            580                 585                 590

Gly Leu Leu Lys Leu Ser Pro Tyr Ala Asn Ser Ile Gly His Ser Ile
            595                 600                 605

Cys Asp Ile Ile Ala Lys Glu Phe Trp Thr Phe Leu Ala His His Leu
            610                 615                 620

Arg Ile Lys Ile His Glu His Ile Leu Ile His Gly Asp Ile Arg Lys
625                 630                 635                 640

Thr Thr Lys Met Glu Ile Gly Gly Glu Glu Val Glu Val Glu Glu Phe
            645                 650                 655

Val Glu Glu Glu Asp Glu Asp Thr Val Val Ser Lys Gly Glu Glu Asp
            660                 665                 670
```

```
Asn Met Ala Ile Ile Lys Glu Phe Met Arg Phe Lys Val His Met Glu
            675                 680                 685
Gly Ser Val Asn Gly His Glu Phe Glu Ile Glu Gly Glu Gly Glu Gly
        690                 695                 700
Arg Pro Tyr Glu Gly Thr Gln Thr Ala Lys Leu Lys Val Thr Lys Gly
705                 710                 715                 720
Gly Pro Leu Pro Phe Ala Trp Asp Ile Leu Ser Pro Gln Phe Met Tyr
                725                 730                 735
Gly Ser Lys Ala Tyr Val Lys His Pro Ala Asp Ile Pro Asp Tyr Leu
            740                 745                 750
Lys Leu Ser Phe Pro Glu Gly Phe Lys Trp Glu Arg Val Met Asn Phe
        755                 760                 765
Glu Asp Gly Gly Val Val Thr Val Thr Gln Asp Ser Ser Leu Gln Asp
770                 775                 780
Gly Glu Phe Ile Tyr Lys Val Lys Leu Arg Gly Thr Asn Phe Pro Ser
785                 790                 795                 800
Asp Gly Pro Val Met Gln Lys Lys Thr Met Gly Trp Glu Ala Ser Ser
                805                 810                 815
Glu Arg Met Tyr Pro Glu Asp Gly Ala Leu Lys Gly Glu Ile Lys Gln
            820                 825                 830
Arg Leu Lys Leu Lys Asp Gly Gly His Tyr Asp Ala Glu Val Lys Thr
        835                 840                 845
Thr Tyr Lys Ala Lys Lys Pro Val Gln Leu Pro Gly Ala Tyr Asn Val
850                 855                 860
Asn Ile Lys Leu Asp Ile Thr Ser His Asn Glu Asp Tyr Thr Ile Val
865                 870                 875                 880
Glu Gln Tyr Glu Arg Ala Glu Gly Arg His Ser Thr Gly Gly Met Asp
                885                 890                 895
Glu Leu Tyr Lys
            900

<210> SEQ ID NO 12
<211> LENGTH: 2703
<212> TYPE: DNA
<213> ORGANISM: Artificial Sequence
<220> FEATURE:
<223> OTHER INFORMATION: Synthetic primer

<400> SEQUENCE: 12
atggattatg gcggcgcgct gagcgcggtg ggccgcgaac tgctgtttgt gaccaacccg      60
gtggtggtga acggcagcgt gctggtgccg aagatcagt gctattgcgc gggctggatt     120
gaaagccgcg gcaccaacgg cgcgcagacc gcgagcaacg tgctgcagtg gctggcggcg     180
ggctttagca ttctgctgct gatgttttat gcgtatcaga cctggaaaag cacctgcggc     240
tgggaagaaa tttatgtgtg cgcgattgaa atggtgaaag tgattctgga atttttttt     300 gaatttaaaa acccgagcat gctgtatctg gcgaccggcc atcgcgtgca gtggctgcgc     360
tatgcggaat ggctgctgac ctgcccggtg atttgcattc atctgagcaa cctgaccggc     420
ctgagcaacg attatagccg ccgcaccatg ggcctgctgg tgagcgatat ggcaccatt     480 gtgtggggcg cgaccagcgc gatggcgacc ggctatgtga aagtgatttt ttttttgcctg     540 ggcctgtgct atggcgcgaa caccttttt catgcggcga aagcgtatat tgaaggctat     600
cataccgtgc gaaaggccg ctgccgccag gtggtgaccg gcatggcgtg gctgtttttt     660
gtgagctggg gcatgttttcc gattctgttt attctgggcc cggaaggctt tggcgtgctg     720
```

```
agcgtgtatg gcagcaccgt gggccatacc attattgatc tgatgagcaa aaactgctgg     780
ggcctgctgg gccattatct gcgcgtgctg attcatgaac atattctgat tcatggcgat     840
attcgcaaaa ccaccaaact gaacattggc ggcaccgaaa ttgaagtgga aaccctggtg     900
gaagatgaag cggaagcggg cgcggtgaac aaaggcaccg gcaaaatggc tgagctgatc     960
agcagcgcca ccagatctct gtttgccgcc ggaggcatca acccttggcc taacccctac    1020
caccacgagg acatgggctg tggaggaatg acacctacag gcgagtgctt cagcaccgag    1080
tggtggtgtg acccttctta cggactgagc gacgccggat acggatattg cttcgtggag    1140
gccacaggcg gctacctggt cgtgggagtg agaagaagc aggcttggct gcacagcaga     1200
ggcacaccag gagaaaagat cggcgcccag gtctgccagt ggattgcttt cagcatcgcc    1260
atcgccctgc tgacattcta cggcttcagc gcctggaagg ccacttgcgg ttgggaggag    1320
gtctacgtct gttgcgtcga ggtgctgttc gtgaccctgg agatcttcaa ggagttcagc    1380
agccccgcca cagtgtacct gtctaccggc aaccacgcct attgcctgcg ctacttcgag    1440
tggctgctgt cttgccccgt gatcctgatc agactgagca acctgagcgg cctgaagaac    1500
gactacagca gcggaccat gggcctgatc gtgtcttgcg tgggaatgat cgtgttcggc      1560
atggccgcag gactggctac cgattggctc aagtggctgc tgtatatcgt gtcttgcatc    1620 tacgcggct acatgtactt ccaggccgcc aagtgctacg tggaagccaa ccacagcgtg     1680
cctaaaggcc attgccgcat ggtcgtgaag ctgatggcct acgcttactt cgcctcttgg    1740
ggcagctacc caatcctctg gcagtgggac cagaaggac tgctgaagct gagcccttac     1800
gccaacagca tcggccacag catctgcgac atcatcgcca aggagttttg gaccttcctg    1860
gcccaccacc tgaggatcaa gatccacgag cacatcctga tccacggcga catccggaag    1920
accaccaaga tggagatcgg aggcgaggag gtggaagtgg aagagttcgt ggaggaggag    1980
gacgaggaca cagtggtgag caagggcgag gaggataaca tggccatcat caaggagttc    2040
atgcgcttca aggtgcacat ggagggctcc gtgaacggcc acgagttcga gatcgagggc    2100
gagggcgagg gccgccccta cgagggcacc cagaccgcca agctgaaggt gaccaagggt    2160
ggccccctgc ccttcgcctg gacatcctg tcccctcagt tcatgtacgg ctccaaggcc     2220
tacgtgaagc accccgccga catcccgac tacttgaagc tgtccttccc cgagggcttc     2280
aagtgggagc gcgtgatgaa cttcgaggac ggcggcgtgg tgaccgtgac ccaggactcc    2340
tccctgcagg acggcgagtt catctacaag gtgaagctgc gcggcaccaa cttcccctcc    2400 gacggcccc taatgcagaa gaagaccatg ggctgggagg cctcctccga gcggatgtac     2460
cccgaggacg gcgccctgaa gggcgagatc aagcagaggc tgaagctgaa ggacggcggc    2520
cactacgacg ctgaggtcaa gaccacctac aaggccaaga gcccgtgca gctgcccggc     2580 gcctacaacg tcaacatcaa gttggacatc acctcccaca cgaggacta ccatcgtg       2640 gaacagtacg aacgcgccga gggccgccac tccaccggcg gcatggacga gctgtacaag    2700
taa                                                                  2703
```

<210> SEQ ID NO 13
<211> LENGTH: 7
<212> TYPE: PRT
<213> ORGANISM: Artificial Sequence
<220> FEATURE:
<223> OTHER INFORMATION: Synthetic peptide

<400> SEQUENCE: 13

```
<210> SEQ ID NO 14
<211> LENGTH: 34
<212> TYPE: PRT
<213> ORGANISM: Artificial Sequence
<220> FEATURE:
<223> OTHER INFORMATION: Synthetic peptide

<400> SEQUENCE: 14

Thr Pro Ala Arg Trp Val Trp Ile Ser Leu Tyr Tyr Ala Ala Phe Tyr
1               5                   10                  15

Val Val Met Thr Gly Leu Phe Ala Leu Cys Ile Tyr Val Leu Met Gln
            20                  25                  30

Thr Ile
```